United States Patent
Lau et al.

(10) Patent No.: US 10,308,700 B2
(45) Date of Patent: *Jun. 4, 2019

(54) GLP-1 DERIVATIVES

(71) Applicant: Novo Nordisk A/S, Bagsvaerd (DK)

(72) Inventors: Jesper Lau, Farum (DK); Paw Bloch, Jyllinge (DK); Jacob Kofoed, Vaerloese (DK); Patrick William Garibay, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 220 days.

This patent is subject to a terminal disclaimer.

(21) Appl. No.: 15/404,808

(22) Filed: Jan. 12, 2017

(65) Prior Publication Data

US 2017/0145069 A1    May 25, 2017

Related U.S. Application Data

(63) Continuation of application No. 14/343,152, filed as application No. PCT/EP2012/067364 on Sep. 6, 2012, now Pat. No. 9,758,560.

(60) Provisional application No. 61/532,323, filed on Sep. 8, 2011.

(30) Foreign Application Priority Data

Sep. 6, 2011 (EP) .................... 11180265

(51) Int. Cl.
A61K 38/00 (2006.01)
A61K 38/26 (2006.01)
C07K 14/605 (2006.01)

(52) U.S. Cl.
CPC ............ C07K 14/605 (2013.01); A61K 38/26 (2013.01); A61K 38/00 (2013.01)

(58) Field of Classification Search
CPC ....... A61K 38/00; A61K 38/26; C07K 14/605
See application file for complete search history.

(56) References Cited

U.S. PATENT DOCUMENTS

| | | | |
|---|---|---|---|
| 5,525,491 | A | 6/1996 | Huston et al. |
| 5,662,907 | A | 9/1997 | Kubo et al. |
| 5,663,907 | A | 9/1997 | Frayer et al. |
| 7,271,149 | B2 | 9/2007 | Glaesner et al. |
| 2007/0135338 | A1 | 6/2007 | O'Neil et al. |
| 2010/0292133 | A1 | 11/2010 | Spetzler et al. |
| 2011/0082079 | A1 | 4/2011 | Spetzler et al. |
| 2015/0133374 | A1 | 5/2015 | Kofoed et al. |
| 2015/0152157 | A1 | 6/2015 | Kofoed et al. |
| 2018/0244742 | A1 | 8/2018 | Kofoed et al. |

FOREIGN PATENT DOCUMENTS

| | | |
|---|---|---|
| CN | 1232470 A | 10/1999 |
| JP | H06-508985 A | 10/1994 |
| JP | 2000-500505 A | 1/2000 |
| WO | 9413313 A1 | 6/1994 |
| WO | 96/29342 | 9/1996 |
| WO | 99/43706 A1 | 9/1999 |
| WO | 9946283 A1 | 9/1999 |
| WO | 2011/080102 A2 | 7/2011 |
| WO | 2011/080103 A1 | 7/2011 |
| WO | 2013/167454 A1 | 11/2013 |
| WO | 2013/167455 A1 | 11/2013 |

OTHER PUBLICATIONS

Chae, Su Young et al.,The fatty acid conjugated exendin-4 analogs for type 2 antidiabetic therapeutics, "Journal of Controlled Release", Jan. 2010, vol. 144, No. 1, pp. 10-16.
Garcia Bustos J et al.A biological price of antibiotic resistance: Major changes in the peptidoglycan structure of penicillin-resistant pneumococci, "Proceedings of the National Academy of Sciences," Year 1990, vol. 87, No. 14, pp. 5415-5419.
Knudsen Lotte B. et al.Potent Derivatives of Glucagon-like Peptide-1 with Pharmacokinetic Properties Suitable for Once Daily Administration, "Journal of Medicinal Chemistry", Year 2000 vol. 43, No. 9, pp. 1664-1669.
Tomasik et al "GLP-1 as aa Satiety Factor in Children with Eating Disorders" Horm. Metab. Res. 2002 vol. 34 pp. 77-80.
Critical Illness—Common Definition, lia.org (Jul. 2003), 8 Pages, also available at http://www.lia.org.sg/files/document_holder/industry_Guidelines_-_Health/CommonDefnCl1July03.pdf (last visited Apr. 29, 2016).
Butler et al "GLP-1-Based Therapy for Diabetes: What You Do Not Know Can Hurt You." Diabetes Care Feb. 2010 vol. 33 No. 2 pp. 453-455.

*Primary Examiner* — Randall L Beane
(74) *Attorney, Agent, or Firm* — Jianjie Hu

(57) ABSTRACT

The invention relates to a derivative of a GLP-1 peptide, which peptide has two Lys residues, namely a first and a second Lys residue, and a maximum of eight amino acid changes as compared to GLP-1(7-37) (SEQ ID NO: 3), which derivative comprises two protracting moieties attached to the epsilon amino group of said first and second Lys residue, respectively, via a linker, wherein the protracting moiety is selected from Chem. 15: HOOC—$(CH_2)_x$—CO—*, and Chem. 16: HOOC—$C_6H_4$—O—$(CH_2)_y$—CO—*, in which x is an integer in the range of 10-16, and y is an integer in the range of 8-12; and the linker comprises a first linker element *—NH—CH($CH_2$OH)—CO—*. A preferred linker is gGlu-Ser-Ser-Gly-Ser-Ser-Gly (SEQ ID NO: 2). The derivative of the invention has a very good potency, and a very good binding to the GLP-1 receptor. The invention also relates to the pharmaceutical use of the derivative, for example in the treatment and/or prevention of all forms of diabetes and related diseases.

16 Claims, No Drawings
Specification includes a Sequence Listing.

SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Peptide linker

<400> SEQUENCE: 1

Ser Ser Gly Ser Ser Gly
1               5

```
<210> SEQ ID NO 2
<211> LENGTH: 7
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu

<400> SEQUENCE: 2

Glu Ser Ser Gly Ser Ser Gly
1               5

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 12
<212> TYPE: PRT
<213> ORGANISM: Artificial Sequence
<220> FEATURE:
<223> OTHER INFORMATION: Peptide linker

<400> SEQUENCE: 4

Ser Ser Gly Ser Ser Gly Ser Ser Gly Ser Ser Gly
1               5                   10

<210> SEQ ID NO 5
<211> LENGTH: 18
<212> TYPE: PRT
<213> ORGANISM: Artificial sequence
<220> FEATURE:
<223> OTHER INFORMATION: Peptide linker

<400> SEQUENCE: 5

Ser Ser Gly Ser Ser Gly Ser Ser Gly Ser Ser Gly Ser Ser Gly Ser
1               5                   10                  15

Ser Gly

<210> SEQ ID NO 6
<211> LENGTH: 7
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu

<400> SEQUENCE: 6

Glu Ser Ser Ala Ser Ser Ala
1               5

<210> SEQ ID NO 7
```

```
<211> LENGTH: 13
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu

<400> SEQUENCE: 7

Glu Ser Ser Gly Ser Ser Gly Ser Ser Gly Ser Ser Gly
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu

<400> SEQUENCE: 8

Glu Ser Ser Ser Ser Ser Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu
<220> FEATURE:
<221> NAME/KEY: MISC_FEATURE
<222> LOCATION: (8)..(8)
<223> OTHER INFORMATION: Lys is epsilon-Lys

<400> SEQUENCE: 9

Glu Ser Ser Gly Ser Ser Gly Lys
1               5

<210> SEQ ID NO 10
<211> LENGTH: 14
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu
<220> FEATURE:
<221> NAME/KEY: MISC_FEATURE
<222> LOCATION: (14)..(14)
<223> OTHER INFORMATION: Lys is epsilon-Lys

<400> SEQUENCE: 10

Glu Ser Ser Gly Ser Ser Gly Ser Gly Ser Gly Lys
1               5                   10

<210> SEQ ID NO 11
<211> LENGTH: 20
<212> TYPE: PRT
<213> ORGANISM: Artificial Sequence
```

```
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu
<220> FEATURE:
<221> NAME/KEY: MISC_FEATURE
<222> LOCATION: (20)..(20)
<223> OTHER INFORMATION: Lys is epsilon-Lys

<400> SEQUENCE: 11

Glu Ser Ser Gly Ser Ser Gly Ser Ser Gly Ser Ser Gly Ser Ser Gly
1               5                   10                  15

Ser Ser Gly Lys
            20

<210> SEQ ID NO 12
<211> LENGTH: 8
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (8)..(8)
<223> OTHER INFORMATION: Lys is epsilon-Lys

<400> SEQUENCE: 12

Glu Ser Ser Ser Ser Ser Ser Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (1)..(1)
<223> OTHER INFORMATION: Glu is gamma-Glu
<220> FEATURE:
<221> NAME/KEY: MISC_FEATURE
<222> LOCATION: (5)..(5)
<223> OTHER INFORMATION: Lys is epsilon-Lys

<400> SEQUENCE: 13

Glu Ser Gly Ser Lys
1               5
```

GLP-1 DERIVATIVES

CROSS-REFERENCE TO RELATED APPLICATIONS

This application is a continuation of U.S. application Ser. No. 14/343,152, filed Apr. 30, 2014 (pending), which is a 35 U.S.C. § 371 National Stage application of International Application PCT/EP2012/067364 (WO 2013/037690), filed Sep. 6, 2012, which claimed priority of European Patent Applications 11180265.8, filed Sep. 6, 2011; this application claims priority under 35 U.S.C. § 119 of U.S. Provisional Applications 61/532,323, filed Sep. 8, 2011; the contents of which are incorporated herein by reference.

TECHNICAL FIELD

The invention relates to GLP-1 derivatives, more in particular to GLP-1 peptides that are acylated via a linker comprising *—NH—CH(CH$_2$OH)—CO—*. The invention also relates to the pharmaceutical use of these derivatives.

SEQUENCE LISTING

The instant application contains a Sequence Listing which has been submitted in ASCII format via EFS-Web and is hereby incorporated by reference in its entirety. Said ASCII copy, created on Aug. 16, 2012 (modified on Dec. 16, 2016), from U.S. application Ser. No. 14/343,152, is named "8382US02_SL_ST25" and is 4 KB in size.

BACKGROUND

U.S. Pat. No. 5,525,491 A discloses serine-rich peptide linkers for linking two or more protein domains to form a fused protein.

U.S. Pat. No. 7,271,149 B2 discloses glycine-rich peptide linkers for GLP-1 fusion proteins.

US 2007/0135338 A1 discloses GLP-1 CH1 deleted mimetibody polypeptides incorporating a linker sequence that contains serine and glycine.

US 2010/0292133 A1 and US 2011/0082079 A1 disclose GLP-1 derivatives incorporating as a linker an amino acid except Cys, or a dipeptide such as Gly-Lys.

SUMMARY

The invention relates to derivatives of GLP-1(7-37) (SEQ ID NO: 3) or analogues thereof.

In these derivatives, albumin binding side chains are covalently attached to two or more Lys residues of the GLP-1 peptide, namely to the epsilon amino group of Lys, each via a linker comprising *—NH—CH(CH$_2$OH)—CO—*, a di-radical of the amino acid serine.

More in particular, the invention relates to a derivative of a GLP-1 peptide, which has two Lys residues, namely a first and a second Lys residue and a maximum of eight amino acid changes as compared to GLP-1(7-37) (SEQ ID NO: 3), which derivative comprises two protracting moieties attached to the epsilon amino group of said first and second Lys residue, respectively, via a linker, wherein the protracting moiety is selected from Chem. 15: HOOC—(CH$_2$)$_x$—CO—*, and Chem. 16: HOOC—C$_6$H$_4$—O—(CH$_2$)$_y$—CO—*, in which x is an integer in the range of 10-16, and y is an integer in the range of 8-12; and the linker comprises a first linker element:

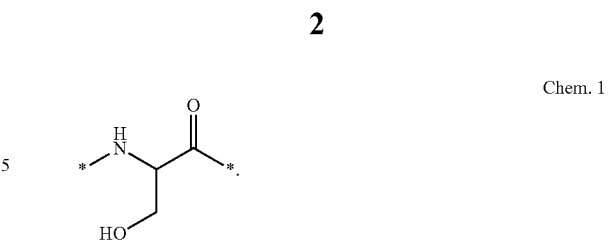

Chem. 1

The invention also relates to a GLP-1 peptide comprising the following amino acid changes as compared to GLP-1 (7-37) (SEQ ID NO: 3): (8Aib, 34H, 37K); or (7Imp, 8Aib, 34R, 37K).

The invention also relates to a GLP-1 peptide having the following amino acid changes as compared to GLP-1(7-37) (SEQ ID NO: 3): (8Aib, 34H, 37K); (7Imp, 8Aib, 34R, 37K); or (7Imp, 8Aib, 18K, 34Q).

The invention also relates to such peptide or derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The derivatives of the invention are biologically active. In particular, they are full GLP-1 receptor agonists as is reflected by their ability to bind to the GLP-1 receptor at a relatively low concentration combined with the capacity to activate the receptor. Also, or alternatively, they have a protracted pharmacokinetic profile. Also, or alternatively, they have a high oral bioavailability. Also, or alternatively, they have a high aqueous solubility and/or dissolution rate.

These properties are of importance in the development of next generation GLP-1 compounds for subcutaneous, intravenous, and/or oral administration.

DESCRIPTION

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

The invention relates to a derivative of a GLP-1 peptide, which peptide has only two Lys residues, namely a first and a second Lys residue, and a maximum of eight amino acid changes as compared to GLP-1(7-37) (SEQ ID NO: 3), which derivative comprises two protracting moieties attached to the epsilon amino group of said first and second Lys residue, respectively, via a linker, wherein the protracting moiety is selected from Chem. 15: HOOC—(CH$_2$)$_x$—CO—*, and Chem. 16: HOOC—C$_6$H$_4$—O—(CH$_2$)$_y$—CO—*, in which x is an integer in the range of 10-16, and y is an integer in the range of 8-12; and the linker comprises a first linker element, Chem. 1:

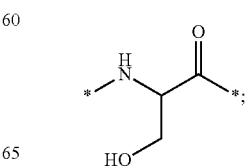

or a pharmaceutically acceptable salt, amide, or ester thereof.

In a particular embodiment, Chem. 1 represents a diradical of the amino acid serine (Ser).

In a further particular embodiment, the linker further comprises a second or a third linker element, Chem. 2 or Chem. 3, respectively:

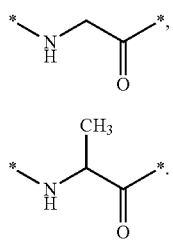

Chem. 2

Chem. 3

Chem. 2 represents a diradical of the amino acid glycine (Gly), and Chem. 3 a diradical of the amino acid alanine (Ala).

In a still further particular embodiment, the linker further comprises a fourth linker element, Chem. 5:

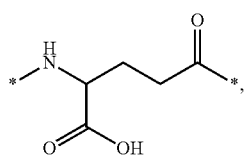

Chem. 5 wherein Chem. 5 represents a diradical of the amino acid gamma glutamic acid (in brief, gamma-Glu, or gGlu).

In a still further embodiment the linker further comprises a fifth linker element, Chem. 12: *—NH—$(CH_2)_4$—CH$(NH_2)$—CO—*, which represents a diradical of the amino acid epsilon-Lys, in brief eps-Lys.

The following are non-limiting examples of linkers for use in the derivative of the invention, wherein Glu refers to gamma-Glu, and Lys to epsilon-Lys:

Glu-Ser-Ser-Gly-Ser-Ser-Gly (SEQ ID NO: 2); Glu-Ser-Ser-Ala-Ser-Ser-Ala (SEQ ID NO: 6); Glu-Ser-Ser-Gly-Ser-Ser-Gly-Ser-Ser-Gly-Ser-Ser-Gly (SEQ ID NO: 7); Glu-Ser-Ser-Ser-Ser-Ser-Ser (SEQ ID NO: 8); Glu-Ser-Ser-Gly-Ser-Ser-Gly-Lys (SEQ ID NO: 9); Glu-Ser-Ser-Gly-Ser-Ser-Gly-Ser-Ser-Gly-Ser-Ser-Gly-Lys (SEQ ID NO: 10); Glu-Ser-Ser-Gly-Ser-Ser-Gly-Ser-Ser-Gly-Ser-Ser-Gly-Ser-Ser-Gly-Lys (SEQ ID NO: 11); Glu-Ser-Ser-Ser-Ser-Ser-Lys (SEQ ID NO: 12); and Glu-Ser-Gly-Ser-Lys (SEQ ID NO: 13).

Thus, for example, SEQ ID NO: 9 refers to the following sequence (and may alternatively be written as follows): gGlu-Ser-Ser-Gly-Ser-Ser-Gly-eps-Lys. The same applies vice versa to the other sequences herein, i.e. to each of SEQ ID NO: 2 and 6-13.

GLP-1 Peptides and Analogues

The term "GLP-1 peptide" as used herein refers to human Glucagon-Like Peptide-1 (GLP-1(7-37)), the sequence of which is included in the sequence listing as SEQ ID NO: 3, or an analogue thereof, a GLP-1 analogue.

The peptide having the sequence of SEQ ID NO: 3 may also be designated native GLP-1. The term "GLP-1 analogue" or "analogue of GLP-1" as used herein refers to a peptide, or a compound, which is a variant of native human GLP-1 (SEQ ID NO: 3).

In the sequence listing, the first amino acid residue of SEQ ID NO: 3 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

A GLP-1 analogue of the derivative of the invention comprises at least two Lys residues. For example, it may comprise a first lysine residue at a position corresponding to position 18 of GLP-1(7-37). If the amino acid sequence of this analogue is otherwise identical to that of native GLP-1, such analogue may be designated $K^{18}$-GLP-1(7-37). This designation accordingly represents the amino acid sequence of native GLP-1 where serine at position 18 has been substituted with lysine. As an added remark, this analogue comprises a second Lys residue at position 26, and a third Lys residue at position 34 (viz. the native lysines of GLP-1(7-37)).

As another example, the analogue comprising a first Lys residue at position 18 may also comprise a lysine in one or more other positions, for example one additional Lys residue at position 31. Such analogue would be designated $K^{18}$, $K^{31}$-GLP-1(7-37), provided that, except for the $K^{18}$- and the $K^{31}$-substitutions, its amino acid sequence would be identical to that of native GLP-1.

The GLP-1 analogue forming part of the derivative of the invention comprises, preferably has, a maximum of eight amino acid changes when compared with native GLP-1 (SEQ ID NO: 3)—in other words, it is a GLP-1 peptide in which a number of amino acid residues have been changed when compared to native GLP-1(7-37) (SEQ ID NO: 3). These changes may represent, independently, one or more amino acid substitutions, additions, and/or deletions.

The following are non-limiting examples of appropriate analogue nomenclature.

For example, the analogue [Aib8,Lys18,Glu22,Val25,Arg26,Lys31,Arg34]-GLP-1-(7-37) designates a GLP-1(7-37) peptide which, when compared to native GLP-1, is changed by the following substitutions: Substitution of alanine at position 8 with Aib (α-aminoisobutyric acid), of serine at position 18 with lysine, of glycine at position 22 with glutamic acid, of alanine at position 25 with valine, of lysine at position 26 with arginine, of tryptophan at position 31 with lysine, and of lysine at position 34 with arginine. This analogue may also be briefly designated (8Aib, 18K, 22E, 25V, 26R, 31K, 34R), where reference to GLP-1(7-37) is implied.

As another example, the analogue [Arg34,Lys37,Glu38]-GLP-1(7-37) designates a GLP-1(7-37) peptide, which, when compared to native GLP-1, is changed by substitution of lysine at position 34 with arginine, substitution of glycine at position 37 with lysine, and addition of glutamic acid to the C-terminus. This analogue may also be briefly designated (34R, 37K, 38E), where reference to GLP-1(7-37) is implied.

As a still further example, an analogue comprising Aib⁸ refers to a GLP-1(7-37) peptide, which, when compared to native GLP-1, comprises a substitution of alanine at position 8 with α-aminoisobutyric acid (Aib). This analogue may comprise further changes as compared to SEQ ID NO: 3.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a GLP-1 sequence by reference to native GLP-1 (7-37) (SEQ ID NO: 3). Equivalent or corresponding positions are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −10 (minus 10) and the penalties for additional residues in a gap at −0.5 (minus 0.5).

An example of such alignment is inserted hereinbelow, in which Sequence_1 is SEQ ID NO: 3, and Sequence_2 is the analogue (34R, 37K, 38E) thereof:

```
# 1: Sequence_1

2: Sequence_2

Matrix: EBLOSUM62

Gap_penalty: 10.0

Extend_penalty: 0.5

Length: 32

Identity: 29/32 (90.6%)

Similarity: 30/32 (93.8%)

Gaps: 1/32 (3.1%)

Score: 150.0

#=======================================

Sequence_1  1 HAEGTFTSDVSSYLEGQAAKEFIAWLVKGRG-  31
              ||||||||||||||||||||||||||||| ||.
Sequence_2  1 HAEGTFTSDVSSYLEGQAAKEFIAWLVRGRKE  32
```

In case of non-natural amino acids such as Imp and/or Aib being included in the sequence, they may, for alignment purposes, be replaced with X. If desired, X can later be manually corrected.

The term "peptide", as e.g. used in the context of linkers as well as GLP-1 analogues of the derivatives of the invention, refers to a compound which comprises a series of amino acids interconnected by amide (or peptide) bonds. The peptide linkers comprise at least three amino acids. The GLP-1 peptides comprise at least 10, preferably at least 15, more preferably at least 20, even more preferably at least 25, or most preferably at least 27 amino acids.

In particular embodiments, the GLP-1 peptide is composed of at least 28, at least 29, at least 30, at least 31, or at least 32 amino acids.

In a still further particular embodiment the peptide consists of amino acids interconnected by peptide bonds.

Amino acids are molecules containing an amine group and a carboxylic acid group, and, optionally, one or more additional groups, often referred to as the amino acid side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, abbreviated Imp).

In what follows, each amino acid of the GLP-1 peptide for which the optical isomer is not stated is to be understood to mean the L-isomer (unless otherwise specified).

The amino acid elements of the linker (except Gly) may exist in either of two optical isomeric forms. Thus, each of Chem. 1 (Ser), Chem. 5 (gGlu), Chem. 7 (Ala), and/or Chem. 12 (eps-Lys) may represent the D-form, the L-form, or a mixture thereof (D/L). In a particular embodiment, each of these is the L-isomer. In another particular embodiment, each of these is the D-isomer. In a further particular embodiment, each of these is a mixture of the D- and L-isomers. In still further particular embodiments i) at least one, preferably each, Ser residue of the linker is in the L-form; ii) at least one, preferably each, Ala residue of the linker is in the L-form, iii) at least one, preferably each, gGlu residue of the linker is in the L-form; and/or iii) at least one, preferably each, eps-Lys residue of the linker is in the L-form.

As it is well known, the L- and D-convention refers to the optical activity of the isomer of glyceraldehyde from which the amino acid in question can be synthesised. Alternatively, the (S) and (R) nomenclature may be used to define the stereochemistry. For the present purposes, the L-designation corresponds to the (S) designation, and the D-designation to the (R) designation.

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using one or more of the assays described in Examples 32-33 herein. The GLP-1 receptor binding assay described in Example 34 herein may also be used as a measure of GLP-1 activity.

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole may be referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion in between the protracting moiety and the point of attachment to the peptide, which portion may be referred to as a linker, a linker moiety, a spacer, or the like.

In particular embodiments, the protracting moiety is lipophilic, and/or negatively charged at physiological pH (7.4).

The albumin binding moiety, the protracting moiety, or the linker may be covalently attached to a lysine residue of the GLP-1 peptide by acylation.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative which has two protracting moieties attached to a first and a second K residue (e.g., to $K^{18}$ and $K^{31}$) via a linker may be referred to as a derivative which has been acylated twice, double-acylated, or dual acylated at the epsilon-amino groups of the first and second lysine residues, e.g. at position 18 and 31, respectively, of the GLP-1 peptide.

For the present purposes, the terms "albumin binding moiety", "protracting moiety", and "linker" include the molecule itself as well as radicals thereof. Whether or not one or the other form is meant is clear from the context in which the term is used. In a preferred embodiment, these terms refer to radicals. The radicals are preferably suitable for forming one or more amide bonds, i.e. with one or two unshared electrons (*) in connection with a carbonyl group and/or an amino group. Examples of such radicals are Chem. 1-Chem. 12, as well as Chem. 15-16, the structures of which are shown in the following.

In one aspect of the invention, each of the two protracting moieties comprises, or consists of, a protracting moiety independently selected from Chem. 15 and Chem. 16:

               Chem. 15:

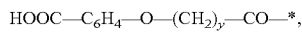
               Chem. 16:

in which x is an integer in the range of 10-16, and y is an integer in the range of 8-12.

In one embodiment, *—$(CH_2)_x$—* refers to straight alkylene.

In another embodiment, *—$(CH_2)_y$—* refers to straight alkylene.

The nomenclature is as is usual in the art, for example in the above formulas *—COOH refers to carboxy, *—$C_6H_4$—* to phenylene, and *—CO—* to carbonyl (O=C<**). In a particular embodiment, the aromatic phenoxy radical is, independently, para.

In a particular embodiment, the two albumin binding moieties (i.e. the entire side chains) are similar, preferably substantially identical, or, most preferably, identical.

In another particular embodiment, the two protracting moieties are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

The similarity of two linkers of the invention may also be determined using a peptide alignment programs known in the art, such as "align", as referred to above.

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b) or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

Reference is made to WO 2011/080103 which on p. 15 incorporates an example of a similarity calculation in which a specific side chain is compared with a methyl ester thereof.

In particular embodiments, two linkers of the invention are at least 90% identical, preferably at least 94% identical, more preferably at least 96% identical, even more preferably at least 98% identical, or most preferably at least 99% identical.

In alternative embodiments, the two linkers are at least 50% identical, preferably at least 60% identical, more preferably at least 70% identical, or most preferably at least 80% identical, wherein the program "align" is used with the settings as described above.

In case of two identical side chains (albumin binding moieties) the derivative may be designated symmetrical.

In a particular embodiment, the linker used in the derivative of the invention comprises the amino acids Ser and Gly. In one embodiment the linker comprises the tri-peptide motif Ser-Ser-Gly. The motif may be repeated, e.g. twice. Thus, in another embodiment, the linker comprises the hexa-peptide motif Ser-Ser-Gly-Ser-Ser-Gly (SEQ ID NO: 1).

The linker may further comprise gGlu, i.e. for example the hepta-peptide motif of gGlu-Ser-Ser-Gly-Ser-Ser-Gly (SEQ ID NO: 2).

In a particular embodiment, gGlu has the structure of Chem. 5:

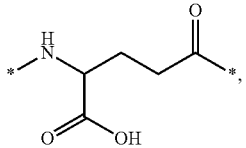

Chem. 5

This linker element may also be referred to as gamma-Glu, or briefly gGlu, due to the fact that it is the gamma carboxy group of the amino acid glutamic acid which is here used for connection to the N-terminus of, e.g., the Ser linker element, or to the epsilon-amino group of lysine, etc., whatever is the case.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118.

Pharmaceutically Acceptable Salt, Amide, or Ester

The peptides and derivatives of the invention may be in the form of a pharmaceutically acceptable salt, amide, or ester.

Salts are e.g. formed by a chemical reaction between a base and an acid, e.g.: $2\ NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a first aspect, the derivatives of the invention have a very good potency. Also, or alternatively, in a second aspect, they bind very well to the GLP-1 receptor at a low concentration of albumin. Preferably they are full GLP-1 receptor agonists as is reflected by their ability to bind strongly to the GLP-1 receptor combined with the capacity to activate the receptor. Also, or alternatively, in a third aspect they have a protracted pharmacokinetic profile. Also, or alternatively, in a fourth aspect they have a high oral bioavailability. Also, or alternatively, in a fifth aspect they have a high aqueous solubility and/or dissolution rate.

Biological Activity (Potency)

According to the first aspect, the derivatives of the invention are biologically active, or potent. In fact, the derivatives of the invention have a surprisingly good potency. This is so in particular when compared with the respective comparative compound hitherto considered best-in-class. The comparative compounds are discussed in the experimental part, in the section headed "Comparative compounds".

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, purified plasma membranes from a stable transfected cell line expressing the human GLP-1 receptor may be stimulated with the GLP-1 analogue or derivative in question, and the potency of cAMP production measured, e.g. based on competition between endogenously formed cAMP and exogenously added biotin-labelled cAMP, which may be captured using a specific antibody, e.g. as described in Example 32.

Also, or alternatively, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 33.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivative of the invention has an in vitro potency in the AlphaScreen membrane-based assay corresponding to an $EC_{50}$ at or below 500 pM, more preferably below 400 pM, even more preferably below 300 pM, or most preferably below 200 pM.

In a further particular embodiment, the derivative of the invention has an in vitro potency in the CRE-luciferase whole-cell assay corresponding to an $EC_{50}$ at or below 100 pM, preferably below 75 pM, more preferably below 50 pM, even more preferably below 25 pM, or most preferably below 10 pM.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect, as well as the body weight lowering effect may be determined in such mice in vivo, e.g. as described in Example 53 of WO 2011/080103.

Receptor Binding/low Albumin

According to the second aspect, the derivatives of the invention bind very well to the GLP-1 receptor at a low concentration of albumin. This may be determined as described in Example 34.

Generally, the binding to the GLP-1 receptor at low albumin concentration should be as good as possible, corresponding to a low half maximal inhibitory concentration ($IC_{50}$) value.

As an example, in a particular embodiment of a derivative of the invention, the GLP-1 receptor binding affinity ($IC_{50}$) in the presence of 0.001% HSA (low albumin) is below 50 nM, preferably below 20 nM, still more preferably below 10 nM, even more preferably below 5.0 nM, or most preferably below 1.0 nM.

GLP-1 Receptor Agonists

A receptor agonist may be defined as a structural analogue that binds to a receptor and elicits a response typical of the natural ligand. A full agonist may be defined as one that elicits a response of the same magnitude as the natural ligand (see e.g. "Principles of Biochemistry", AL Lehninger, DL Nelson, MM Cox, Second Edition, Worth Publishers, 1993, page 763).

In a particular embodiment, the derivative of the invention is a full GLP-1 receptor agonist. A full GLP-1 receptor agonist may, e.g., be defined as a structural analogue of GLP-1(7-37) (SEQ ID NO: 3) that (i) binds to the GLP-1 receptor with an $IC_{50}$ value equal to or less than 50 nM in a receptor binding affinity assay (such as the one of Example 34 herein); and (ii) activates the receptor with an $EC_{50}$ value equal to or less than 100 pM in a reporter gene assay (such as the one of Example 33 herein), and/or an $EC_{50}$ value equal to or less than 500 pM in a cAMP assay (such as the one of Example 32 herein).

Protraction—Half Life in vivo in Minipigs According to the third aspect, the derivatives of the invention are protracted. In a particular embodiment, protraction may be determined as terminal half-life ($T_{1/2}$) in vivo in minipigs after i.v. administration, as described in Example 54 of WO 2011/080103.

In a particular embodiment, the derivative of the invention has a terminal half-life ($T_{1/2}$) after i.v. administration in minipigs of at least 8 hours, preferably at least 16 hours, more preferably at least 24 hours, even more preferably at least 32 hours, or most preferably at least 40 hours.

In still further particular embodiments, the derivative of the invention has a terminal half-life ($T_{1/2}$) after i.v. administration in minipigs of at least 50 hours, preferably at least 55 hours, more preferably at least 60 hours, even more preferably at least 65 hours, or most preferably at least 70 hours.

In still further particular embodiments, the derivative of the invention has a terminal half-life ($T_{1/2}$) after i.v. administration in minipigs of at least 75 hours, preferably at least 80 hours, or most preferably at least 85 hours.

The protracted derivatives of the invention preferably also have a very good potency, as defined in particular embodiments and additional particular embodiments included hereinbelow.

The protracted derivatives of the invention preferably also have a very good binding to the GLP-1 receptor, as defined in particular embodiments and additional particular embodiments included hereinbelow.

Oral Bioavailability

According to the fourth aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of (with) an improved oral bioavailability. Such derivatives could be suitable candidates for oral administration, as long as mainly their potency is generally satisfactory, and/or as long as their half-life is also generally satisfactory.

Generally, the term bioavailability refers to the fraction of an administered dose of an active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to degradation and/or incomplete absorption and first-pass metabolism).

Knowledge about bioavailability is important when calculating dosages for non-intravenous routes of administration.

A plasma API concentration vs time plot is made after both oral and intravenous administration. The absolute bioavailability (F) is the (AUC-oral divided by dose), divided by (AUC-intravenous divided by dose).

In a particular embodiment, the derivative of the invention has an absolute oral bioavailability which is higher than that of liraglutide, and/or that of semaglutide, preferably at least 10% higher, more preferably at least 20% higher, even more preferably at least 30% higher, or most preferably at least 40% higher. In additional particular embodiments, it has an absolute oral bioavailability which is at least 1.5 times that of liraglutide, and/or that of semaglutide, preferably at least 2.0 times, more preferably at least 3.0 times, even more preferably at least 4.0 times, or most preferably at least 5.0 times that of liraglutide, and/or that of semaglutide.

Before testing oral bioavailability the derivatives of the invention may suitably be formulated as is known in the art of oral formulations of insulinotropic compounds, e.g. using any one or more of the formulations described in WO 2008/145728.

Oral bioavailability may, e.g., be estimated in a rat gut injection and/or oral gavage study, in a formulation with SNAC, as described in Example 40 of PCT/EP2012/056642.

Water Solubility

High concentration delivery via the oral route is difficult to achieve for several peptide pharmaceuticals. This may at least partly be due to low solubility. In a fifth aspect, the derivatives of the invention have a high aqueous solubility and/or dissolution rate. This is one of several properties of importance for obtaining a pharmaceutically effective oral product. In a particular embodiment, the derivatives of this invention have a higher aqueous solubility compared to closest prior art. Also, or alternatively, they have a faster dissolution in aqueous buffers. The absolute solubility of a peptide can be measured using different methods known in the art, see for example J. Pharm. Sci., 2008, 4155-66. For measuring dissolution and/or solubility of peptides in milligram scale one can, for example, use the instruments from Pion Instruments (www.pion-inc.com) such as the μDISS Profiler™, which is a versatile instrument for measuring concentration in real time with fiber UV spectroscopy.

Additional particular embodiments of the derivatives of the invention are described in the sections headed "particular embodiments" and "additional particular embodiments" before the experimental section.

Production Processes

The production of peptides like GLP-1(7-37) and GLP-1 analogues is well known in the art.

The GLP-1 moiety of the derivatives of the invention, viz. $K^{18}$-GLP-1(7-37) or an analogue thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical compositions comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. formulations comprising water. A liquid formulation may be a solution, or a suspension. An aqueous formulation typically comprises at least 50% w/w water, or at least 60%, 70%, 80%, or even at least 90% w/w of water.

Alternatively a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the peptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogues) may be added to inhibit oxidation of methionine residues to methionine sulfoxide when the peptide is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01 mg-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. In a particular embodiment the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may further be compounded in a drug carrier or drug delivery system, e.g. in order to improve stability, bioavailability, and/or solubility. A composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atherosclerosis; mild chronic heart failure; angina pectoris; cardiac bypass reocclusion; intermittent claudication (atherosclerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

Particular Embodiments

1. A derivative of a GLP-1 peptide,
   which peptide has two Lys residues, namely a first and a second Lys residue, and a maximum of eight amino acid changes as compared to GLP-1(7-37) (SEQ ID NO: 3),
   which derivative has two protracting moieties attached to the epsilon amino group of said first and second Lys residue, respectively, via a linker, wherein
   the protracting moiety is selected from Chem. 15, and Chem. 16:

  Chem. 15:

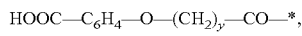  Chem. 16:

in which x is an integer in the range of 10-16, and y is an integer in the range of 8-12; and
   the linker comprises a first linker element, Chem. 1:

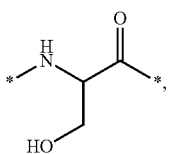

Chem. 1 or a pharmaceutically acceptable salt, amide, or ester of said derivative.

2. The derivative of embodiment 1, wherein the linker comprises two times Chem. 1.
3. The derivative of embodiment 1, wherein the linker comprises four times Chem. 1.
4. The derivative of embodiment 1, wherein the linker comprises six times Chem. 1.
5. The derivative of embodiment 1, wherein the linker comprises eight times Chem. 1.
6. The derivative of embodiment 1, wherein the linker comprises twelve times Chem. 1.
7. The derivative of any of embodiments 1-3, or 5-6, wherein the linker further comprises a second linker element, Chem. 2:

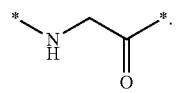

8. The derivative of embodiment 7, wherein the linker comprises a combination of first and second linker elements as follows, Chem. 3:

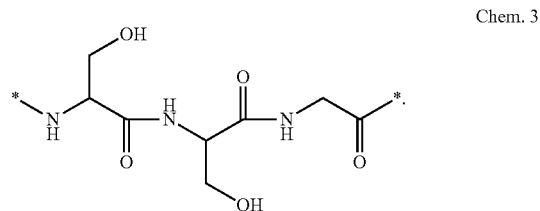

Chem. 3

9. The derivative of any of embodiments 7-8, wherein the linker comprises a combination of first and second linker elements as follows, Chem. 4:

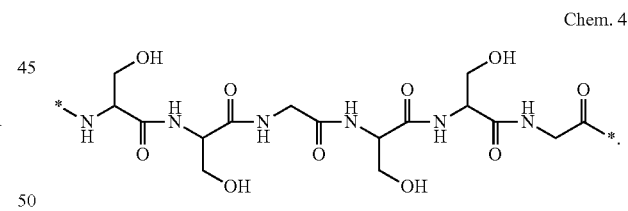

Chem. 4

10. The derivative of any of embodiments 7-9, wherein the linker comprises a combination of first and second linker elements as follows, Chem. 10:

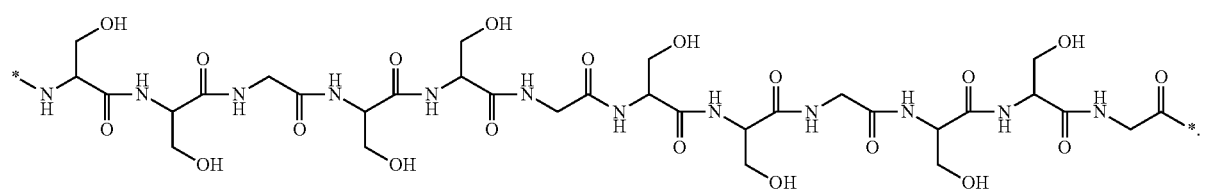

Chem. 10

11. The derivative of any of embodiments 7-10, wherein the linker comprises a combination of first and second linker elements as follows, Chem. 11:

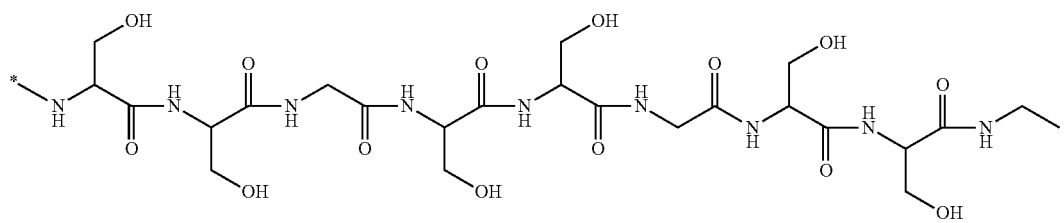

Chem. 11

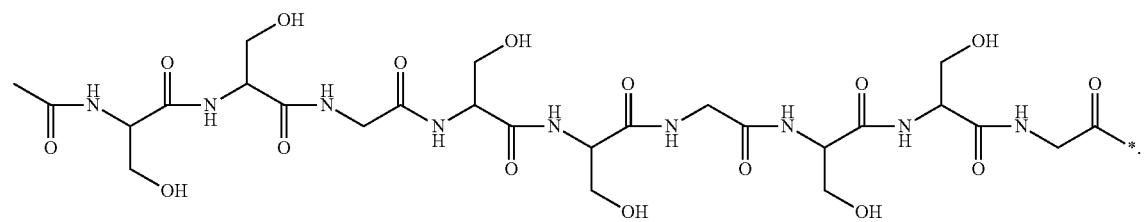

12. The derivative of embodiment 7, wherein the linker comprises a combination of first and second linker elements as follows, Chem. 8:

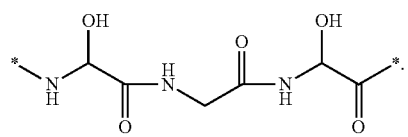

Chem. 8

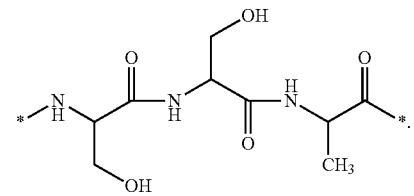

Chem. 9

13. The derivative of any of embodiments 1-3, wherein the linker further comprises a third linker element, Chem. 7:

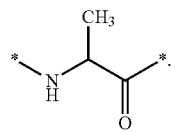

15. The derivative of any of embodiments 1-14, wherein the linker further comprises a fourth linker element, Chem. 5:

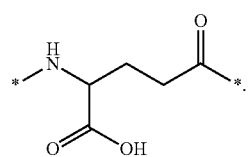

Chem. 5

14. The derivative of embodiment 13, wherein the linker comprises a combination of first and third linker elements as follows, Chem. 9:

16. The derivative of embodiment 15 where Chem. 5 is connected at its *—NH end to the carbonyl group of the protracting moiety.

17. The derivative of any of embodiments 1-3, 7-9, or 15-16, wherein the linker comprises Chem. 6:

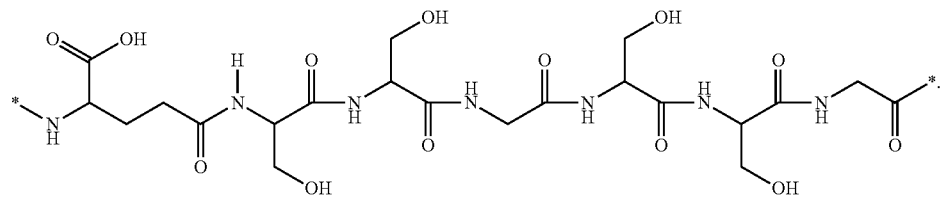

Chem. 6

18. The derivative of any of embodiments 1-12, or 15-17, wherein the linker further comprises a fifth linker element, Chem. 12:

$$*-NH-(CH_2)_4-CH(NH_2)-CO-*.$$ Chem. 12:

19. The derivative of embodiment 18 where Chem. 12 is connected at its CO—* end to the epsilon amino group of the first or the second Lys residue of the GLP-1 peptide.
20. The derivative of any of embodiments 1-3, or 13-16, which comprises one time Chem. 5 and two times Chem. 9.
21. The derivative of any of embodiments 1-5, 7-10, or 15-16, which comprises one time Chem. 5 and four times Chem. 3.
22. The derivative of any of embodiments 1-4, or 15-16, which comprises one time Chem. 5 and six times Chem. 1.
23. The derivative of any of embodiments 1-3, 7-9, 15-16, or 18-19, which comprises one time Chem. 5, two times Chem. 3, and one time Chem. 12.
24. The derivative of any of embodiments 1-5, 7-10, 15-16, or 18-19, which comprises one time Chem. 5, four times Chem. 3, and one time Chem. 12.
25. The derivative of any of embodiments 1-11, 15-16, or 18-19, which comprises one time Chem. 5, six times Chem. 3, and one time Chem. 12.
26. The derivative of any of embodiments 1-4, 15-16, or 18-19, which comprises one time Chem. 5, six times Chem. 1, and one time Chem. 12.
27. The derivative of any of embodiments 1-2, 7, 12, 15-16, or 18-19, which comprises one time Chem. 5, one time Chem. 8, and one time Chem. 12.
28. The derivative of any of embodiments 1-3, 7-9, or 15-17, wherein the linker consists of Chem. 6, connected at its *—NH end to the carbonyl group of the protracting moiety via an amide bond, and at its CO—* end to the epsilon amino group of the first or the second Lys residue of the GLP-1 peptide via an amide bond.
29. The derivative of any of embodiments 1-3, 13-16, or 20, wherein the linker consists of "Chem. 5—Chem. 9—Chem. 9", wherein the linker elements Chem. 5, Chem. 9, and Chem. 9 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
30. The derivative of any of embodiments 1-5, 7-10, 15-16, or 21, wherein the linker consists of "Chem. 5—Chem. 3—Chem. 3—Chem. 3—Chem. 3", wherein the linker elements Chem. 5, Chem. 3, Chem. 3, Chem. 3, and Chem. 3 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
31. The derivative of any of embodiments 1-4, or 15-16, or 22, wherein the linker consists of "Chem. 5—Chem. 1—Chem. 1—Chem. 1—Chem. 1—Chem. 1—Chem. 1", wherein the linker elements Chem. 5, Chem. 1, Chem. 1, Chem. 1, Chem. 1, Chem. 1, and Chem. 1 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
32. The derivative of any of embodiments 1-3, 7-9, 15-16, 18-19, or 23, wherein the linker consists of "Chem. 5—Chem. 3—Chem. 3—Chem. 12", wherein the linker elements Chem. 5, Chem. 3, Chem. 3, and Chem. 12 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
33. The derivative of any of embodiments 1-5, 7-10, 15-16, 18-19 or 24, wherein the linker consists of "Chem. 5—Chem. 3—Chem. 3—Chem. 3—Chem. 3—Chem. 12", wherein the linker elements Chem. 5, Chem. 3, Chem. 3, Chem. 3, Chem. 3, and Chem. 12 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
34. The derivative of any of embodiments 1-11, 15-16, 18-19, or 25, wherein the linker consists of "Chem. 5—Chem. 3—Chem. 3—Chem. 3—Chem. 3—Chem. 3—Chem. 3—Chem. 12", wherein the linker elements Chem. 5, Chem. 3, Chem. 3, Chem. 3, Chem. 3, Chem. 3, Chem. 3, and Chem. 12 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
35. The derivative of any of embodiments 1-4, 15-16, 18-19, or 26, wherein the linker consists of "Chem. 5—Chem. 1—Chem. 1—Chem. 1—Chem. 1—Chem. 1—Chem. 1—Chem. 12", wherein the linker elements Chem. 5, Chem. 1, Chem. 1, Chem. 1, Chem. 1, Chem. 1, Chem. 1, and Chem. 12 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
36. The derivative of any of embodiments 1-2, 7, 12, 15-16, 18-19, or 27, wherein the linker consists of "Chem. 5—Chem. 8—Chem. 12", wherein the linker elements Chem. 5, Chem. 8, and Chem. 12 are interconnected via amide bonds, in the sequence indicated (i.e. with the *—NH end to the left and the CO—* end to the right), and wherein the linker is furthermore connected at the *—NH end to the carbonyl group of the protracting moiety via an amide bond, and at the CO—* end to the epsilon amino group of the first or the second Lys residue of the GLP-1 peptide.
37. The derivative of any of embodiments 1-36, wherein Chem. 1 is Ser.
38. The derivative of any of embodiments 1-37, wherein Chem. 2 is Gly.
39. The derivative of any of embodiments 1-38, wherein Chem. 3 is Ser-Ser-Gly.

40. The derivative of any of embodiments 1-39, wherein Chem. 4 is Ser-Ser-Gly-Ser-Ser-Gly (SEQ ID NO: 1).
41. The derivative of any of embodiments 1-40, wherein Chem. 5 is gGlu.
42. The derivative of any of embodiments 1-41, wherein Chem. 6 is gGlu-Ser-Ser-Gly-Ser-Ser-Gly (SEQ ID NO: 2).
43. The derivative of any of embodiments 1-42, wherein Chem. 7 is Ala.
44. The derivative of any of embodiments 1-43, wherein Chem. 8 is Ser-Gly-Ser.
45. The derivative of any of embodiments 1-44, wherein Chem. 9 is Ser-Ser-Ala.
46. The derivative of any of embodiments 1-45, wherein Chem. 10 is Ser-Ser-Gly-Ser-Ser-Gly-Ser-Ser-Gly-Ser-Ser-Gly (SEQ ID NO: 4).
47. The derivative of any of embodiments 1-46, wherein Chem. 11 is Ser-Ser-Gly-Ser-Ser-Gly-Ser-Ser-Gly-Ser-Ser-Gly-Ser-Ser-Gly-Ser-Ser-Gly (SEQ ID NO: 5).
48. The derivative of any of embodiments 1-47, wherein Chem. 12 is eps-Lys.
49. The derivative of any of embodiments 1-3, 7-9, 15-17, or 28, wherein the linker is gGlu-Ser-Ser-Gly-Ser-Ser-Gly (SEQ ID NO: 2).
50. The derivative of any of embodiments 1-3, 13-16, 20, or 29, wherein the linker is gGlu-Ser-Ser-Ala-Ser-Ser-Ala (SEQ ID NO: 6).
51. The derivative of any of embodiments 1-5, 7-10, 15-16, 21, or 30, wherein the linker is gGlu-Ser-Ser-Gly-Ser-Ser-Gly-Ser-Ser-Gly-Ser-Ser-Gly (SEQ ID NO: 7).
52. The derivative of any of embodiments 1-4, or 15-16, 22, or 31, wherein the linker is gGlu-Ser-Ser-Ser-Ser-Ser-Ser (SEQ ID NO: 8).
53. The derivative of any of embodiments 1-3, 7-9, 15-16, 18-19, 23, or 32, wherein the linker is gGlu-Ser-Ser-Gly-Ser-Ser-Gly-eps-Lys (SEQ ID NO: 9).
54. The derivative of any of embodiments 1-5, 7-10, 15-16, 18-19, 24, or 33, wherein the linker is gGlu-Ser-Ser-Gly-Ser-Ser-Gly-Ser-Ser-Gly-Ser-Ser-Gly-eps-Lys (SEQ ID NO: 10).
55. The derivative of any of embodiments 1-11, 15-16, 18-19, 25, or 34, wherein the linker is gGlu-Ser-Ser-Gly-Ser-Ser-Gly-Ser-Ser-Gly-Ser-Ser-Gly-Ser-Ser-Gly-Ser-Ser-Gly-eps-Lys (SEQ ID NO: 11).
56. The derivative of any of embodiments 1-4, 15-16, 18-19, 26, or 35, wherein the linker is gGlu-Ser-Ser-Ser-Ser-Ser-Ser-eps-Lys (SEQ ID NO: 12).
57. The derivative of any of embodiments 1-2, 7, 12, 15-16, 18-19, 27, or 36, wherein the linker is gGlu-Ser-Gly-Ser-eps-Lys (SEQ ID NO: 13).
58. The derivative of any of embodiments 1-57, wherein the GLP-1 peptide is GLP-1(7-37) (SEQ ID NO: 3) or an analogue thereof.
59. The derivative of embodiment 58, wherein the analogue has a maximum of 8 amino acid changes as compared to GLP-1(7-37) (SEQ ID NO: 3).
60. The derivative of any of embodiments 58-59, wherein the analogue has a maximum of 7 amino acid changes as compared to GLP-1(7-37) (SEQ ID NO: 3).
61. The derivative of any of embodiments 58-60, wherein the analogue has a maximum of 6 amino acid changes as compared to GLP-1(7-37) (SEQ ID NO: 3).
62. The derivative of any of embodiments 58-61, wherein the analogue has a maximum of 5 amino acid changes as compared to GLP-1(7-37) (SEQ ID NO: 3).
63. The derivative of any of embodiments 58-62, wherein the analogue has a maximum of 4 amino acid changes as compared to GLP-1(7-37) (SEQ ID NO: 3).
64. The derivative of any of embodiments 58-63, wherein the analogue has a maximum of 3 amino acid changes as compared to GLP-1(7-37) (SEQ ID NO: 3).
65. The derivative of any of embodiments 58-64, wherein the analogue has 7 amino acid changes as compared to GLP-1(7-37) (SEQ ID NO: 3).
66. The derivative of any of embodiments 58-65, wherein the analogue has 4 amino acid changes as compared to GLP-1(7-37) (SEQ ID NO: 3).
67. The derivative of any of embodiments 58-66, wherein the analogue has 3 amino acid changes as compared to GLP-1(7-37) (SEQ ID NO: 3).
68. The derivative of any of embodiments 58-67, wherein the analogue has a minimum of 3 amino acid changes as compared to GLP-1 (7-37) (SEQ ID NO: 3).
69. The derivative of any of embodiments 58-68, wherein the analogue has a minimum of 4 amino acid changes as compared to GLP-1 (7-37) (SEQ ID NO: 3).
70. The derivative of any of embodiments 58-69, wherein the analogue has a minimum of 5 amino acid changes as compared to GLP-1 (7-37) (SEQ ID NO: 3).
71. The derivative of any of embodiments 58-70, wherein the analogue has a minimum of 6 amino acid changes as compared to GLP-1 (7-37) (SEQ ID NO: 3).
72. The derivative of any of embodiments 58-71, wherein the analogue has a minimum of 7 amino acid changes as compared to GLP-1 (7-37) (SEQ ID NO: 3).
73. The derivative of any of embodiments 1-72, wherein the amino acid changes are, independently, selected from substitutions, deletions, and additions.
74. The derivative of any of embodiments 1-73, wherein the amino acid changes are, independently, selected from substitutions and additions.
75. The derivative of any of embodiments 1-74, wherein the amino acid changes are substitutions.
76. The derivative of any of embodiments 1-75, wherein the GLP-1 peptide comprises a GLP-1 peptide of Formula I:

Formula I: $Xaa_7$-$Xaa_8$-Glu-Gly-Thr-Phe-Thr-Ser-Asp-$Xaa_{11}$-Ser-$Xaa_{16}$-$Xaa_{18}$-$Xaa_{20}$-Glu-$Xaa_{22}$-$Xaa_{23}$-Ala-$Xaa_{25}$-$Xaa_{28}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein $Xaa_7$ is L-histidine, imidazopropionyl, α-hydroxy-histidine, D-histidine, desamino-histidine, 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{16}$ is Val or Leu;
$Xaa_{18}$ is Ser or Lys;
$Xaa_{19}$ is Tyr or Gln;
$Xaa_{20}$ is Leu or Met;
$Xaa_{22}$ is Gly, Glu, Lys, or Aib;
$Xaa_{23}$ is Gln, Glu, or Arg;
$Xaa_{25}$ is Ala or Val;
$Xaa_{26}$ is Val, His, Lys, or Arg;
$Xaa_{27}$ is Glu, Leu, or Lys;
$Xaa_{30}$ is Ala, Glu, Lys, or Arg;
$Xaa_{31}$ is Trp, Lys, or His;
$Xaa_{33}$ is Val or Lys;

Xaa₃₄ is Lys, Glu, Asn, Gly, Gln, His, Arg, or absent;
Xaa₃₅ is Gly, Aib, or absent;
Xaa₃₆ is Arg, Gly, Lys, or absent;
Xaa₃₇ is Gly, Ala, Glu, Pro, Lys, Arg, or absent; and
Xaa₃₈ is Ser, Gly, Ala, Glu, Pro, Lys, Arg, or absent.

77. The derivative of any of embodiments 1-76, wherein the GLP-1 peptide is a GLP-1 peptide of Formula I.
78. The derivative of any of embodiments 76-77, wherein the peptide of Formula I is an analogue of GLP-1(7-37) (SEQ ID NO: 3).
79. The derivative of any of embodiments 76-78, wherein if Xaa₃₇ is absent, then Xaa₃₈ is also absent.
80. The derivative of any of embodiments 76-79, wherein if Xaa₃₆ is absent, then Xaa₃₇, and Xaa₃₈ are also absent.
81. The derivative of any of embodiments 76-80, wherein if Xaa₃₅ is absent, then Xaa₃₆, Xaa₃₇, and Xaa₃₈ are also absent.
82. The derivative of any of embodiments 76-81, wherein if Xaa₃₄ is absent, then Xaa₃₅, Xaa₃₆, Xaa₃₇, and Xaa₃₈ are also absent.
83. The derivative of any of embodiments 76-82, wherein Xaa₇ is L-histidine or imidazopropionyl; Xaa₈ is Ala or Aib; Xaa₁₆ is Val; Xaa₁₈ is Ser or Lys; Xaa₁₉ is Tyr; Xaa₂₀ is Leu; Xaa₂₂ is Gly or Glu; Xaa₂₃ is Gln; Xaa₂₅ is Ala or Val; Xaa₂₆ is Lys or Arg; Xaa₂₇ is Glu; Xaa₃₀ is Ala; Xaa₃₁ is Trp, Lys, or His; Xaa₃₃ is Val; Xaa₃₄ is Lys, Gln, His, or Arg; Xaa₃₅ is Gly; Xaa₃₆ is Arg; Xaa₃₇ is Gly or Lys; and Xaa₃₈ is Glu, Lys, or absent.
84. The derivative of any of embodiments 1-83, wherein the GLP-1 peptide comprises His⁷.
85. The derivative of any of embodiments 1-83, wherein the GLP-1 peptide comprises Imp⁷.
86. The derivative of any of embodiments 1-85, wherein the GLP-1 peptide comprises Ala⁸.
87. The derivative of any of embodiments 1-85, wherein the GLP-1 peptide comprises Aib⁸.
88. The derivative of any of embodiments 1-87, wherein the GLP-1 peptide comprises Val¹⁶.
89. The derivative of any of embodiments 1-88, wherein the GLP-1 peptide comprises Ser¹⁸.
90. The derivative of any of embodiments 1-88, wherein the GLP-1 peptide comprises Lys¹⁸.
91. The derivative of any of embodiments 1-90, wherein the GLP-1 peptide comprises Tyr¹⁹.
92. The derivative of any of embodiments 1-91, wherein the GLP-1 peptide comprises Leu²⁰.
93. The derivative of any of embodiments 1-92, wherein the GLP-1 peptide comprises Gly²².
94. The derivative of any of embodiments 1-92, wherein the GLP-1 peptide comprises Gln²².
95. The derivative of any of embodiments 1-94, wherein the GLP-1 peptide comprises Gln²³.
96. The derivative of any of embodiments 1-95, wherein the GLP-1 peptide comprises Ala²⁵.
97. The derivative of any of embodiments 1-95, wherein the GLP-1 peptide comprises Val²⁵.
98. The derivative of any of embodiments 1-97, wherein the GLP-1 peptide comprises Lys²⁶.
99. The derivative of any of embodiments 1-97, wherein the GLP-1 peptide comprises Arg²⁸.
100. The derivative of any of embodiments 1-99, wherein the GLP-1 peptide comprises Glu²⁷.
101. The derivative of any of embodiments 1-100, wherein the GLP-1 peptide comprises Ala³⁰.
102. The derivative of any of embodiments 1-101, wherein the GLP-1 peptide comprises His³¹.
103. The derivative of any of embodiments 1-101, wherein the GLP-1 peptide comprises Trp³¹.
104. The derivative of any of embodiments 1-101, wherein the GLP-1 peptide comprises Lys³¹.
105. The derivative of any of embodiments 1-104, wherein the GLP-1 peptide comprises Val³³.
106. The derivative of any of embodiments 1-105, wherein the GLP-1 peptide comprises Gln³⁴.
107. The derivative of any of embodiments 1-105, wherein the GLP-1 peptide comprises Arg³⁴.
108. The derivative of any of embodiments 1-105, wherein the GLP-1 peptide comprises His³⁴.
109. The derivative of any of embodiments 1-105, wherein the GLP-1 peptide comprises Lys³⁴.
110. The derivative of any of embodiments 1-109, wherein the GLP-1 peptide comprises Gly³⁵.
111. The derivative of any of embodiments 1-110, wherein the GLP-1 peptide comprises Arg³⁶.
112. The derivative of any of embodiments 1-111, wherein the GLP-1 peptide comprises Gly³⁷.
113. The derivative of any of embodiments 1-111, wherein the GLP-1 peptide comprises Lys³⁷.
114. The derivative of any of embodiments 1-113, wherein the GLP-1 peptide comprises Lys³⁸.
115. The derivative of any of embodiments 1-113, wherein, in the GLP-1 peptide, Xaa³⁸ is absent.
116. The derivative of any of embodiments 1-113, wherein the GLP-1 peptide comprises Glu³⁸.
117. The derivative of any of embodiments 1-116, wherein the GLP-1 peptide has only two Lys residues.
118. The derivative of any of embodiments 1-117, wherein the two Lys residues are Lys²⁶ and Lys³⁷.
119. The derivative of any of embodiments 1-117, wherein the two Lys residues are Lys¹⁸ and Lys²⁶.
120. The derivative of any of embodiments 1-117, wherein the two Lys residues are Lys¹⁸ and Lys³¹.
121. The derivative of any of embodiments 1-117, wherein the two Lys residues are Lys²⁶ and Lys³⁸.
122. The derivative of any of embodiments 117-121, wherein the GLP-1 peptide comprises Gln³⁴, His³⁴, or Arg³⁴.
123. The derivative of any of embodiments 120 or 122, wherein the GLP-1 peptide comprises Arg²⁶.
124. The derivative of embodiment 123, wherein the GLP-1 peptide comprises Arg²⁶ and Arg³⁴.
125. The derivative of any of embodiments 1-124, wherein the GLP-1 peptide comprises the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K; (iv) 34R, 37K, 38E; (v) 18K, 22E, 34Q; (vi) 8Aib, 18K, 22E, 25V, 26R, 31K, 34R; (vii) 8Aib, 18K, 22E, 34Q; (iix) 8Aib, 18K, 34Q; (ix) 8Aib, 34Q, 37K; (x) 8Aib, 34H, 37K; (xi) 8Aib, 31H, 34Q, 38K; (xii) 7Imp, 8Aib, 34R, 37K; or (xiiv) 7Imp, 8Aib, 18K, 34Q.
126. The derivative of any of embodiments 1-125, wherein the GLP-1 peptide comprises the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K; (iv) 34R, 37K, 38E; (v) 18K, 22E, 34Q; (vi) 8Aib, 18K, 22E, 25V, 26R, 31K, 34R; (vii) 8Aib, 18K, 22E, 34Q; (ix) 8Aib, 34Q, 37K; (x) 8Aib, 34H, 37K; (xi) 8Aib, 31H, 34Q, 38K; (xii) 7Imp, 8Aib, 34R, 37K; or (xiiv) 7Imp, 8Aib, 18K, 34Q.
127. The derivative of any of embodiments 1-126, wherein the GLP-1 peptide has the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K;

(iv) 34R, 37K, 38E; (v) 18K, 22E, 34Q; (vi) 8Aib, 18K, 22E, 25V, 26R, 31K, 34R; (vii) 8Aib, 18K, 22E, 34Q; (iix) 8Aib, 18K, 34Q; (ix) 8Aib, 34Q, 37K; (x) 8Aib, 34H, 37K; (xi) 8Aib, 31H, 34Q, 38K; (xii) 7Imp, 8Aib, 34R, 37K; or (xiiv) 7Imp, 8Aib, 18K, 34Q.

128. The derivative of any of embodiments 1-127, wherein the GLP-1 peptide has the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K; (iv) 34R, 37K, 38E; (v) 18K, 22E, 34Q; (vi) 8Aib, 18K, 22E, 25V, 26R, 31K, 34R; (vii) 8Aib, 18K, 22E, 34Q; (ix) 8Aib, 34Q, 37K; (x) 8Aib, 34H, 37K; (xi) 8Aib, 31H, 34Q, 38K; (xii) 7Imp, 8Aib, 34R, 37K; or (xiiv) 7Imp, 8Aib, 18K, 34Q.

129. The derivative of any of embodiments 1-128, wherein the GLP-1 peptide does not have the following amino acid changes, as compared to GLP-1(7-37) (SEQ ID NO: 3): (iix) 8Aib, 18K, 34Q.

130. The derivative of any of embodiments 1-129, wherein the number of amino acid changes as compared to GLP-1(7-37) (SEQ ID NO: 3) are identified by handwriting and eyeballing.

131. The derivative of any of embodiments 1-130, wherein the art and position of amino acid changes are as compared to GLP-1(7-37) (SEQ ID NO: 3), and are identified by handwriting and eyeballing.

132. The derivative of any of embodiments 1-131, wherein the art and position of amino acid changes are as compared to GLP-1(7-37) (SEQ ID NO: 3), and are identified by use of a standard protein or peptide alignment program.

133. The derivative of embodiment 132, wherein the alignment program is a Needleman-Wunsch alignment.

134. The derivative of any of embodiments 132-133, wherein the default scoring matrix and the default identity matrix is used.

135. The derivative of any of embodiments 132-134, wherein the scoring matrix is BLOSUM62.

136. The derivative of any of embodiments 132-135, wherein the penalty for the first residue in a gap is −10 (minus ten).

137. The derivative of any of embodiments 132-136, wherein the penalties for additional residues in a gap is −0.5 (minus point five).

138. The derivative of any of embodiments 1-137, wherein x is an even number.

139. The derivative of any of embodiments 1-138, wherein x is 12 or 14.

140. The derivative of any of embodiments 1-139, wherein x is 12.

141. The derivative of any of embodiments 1-139, wherein x is 14.

142. The derivative of any of embodiments 1-141, wherein y is 9, 10, or 11.

143. The derivative of any of embodiments 1-142, wherein y is 9.

144. The derivative of any of embodiments 1-142, wherein y is 10.

145. The derivative of any of embodiments 1-142, wherein y is 11.

146. The derivative of any of embodiments 1-145, wherein the protracting moiety is Chem. 15.

147. The derivative of any of embodiments 1-145, wherein the protracting moiety is Chem. 16.

148. The derivative of any of embodiments 1-146, wherein Chem. 15 is represented by Chem. 15a:

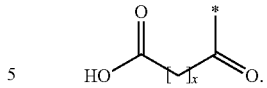

Chem. 15a

149. The derivative of any of embodiments 1-145 or 147, wherein Chem. 16 is represented by Chem. 16a:

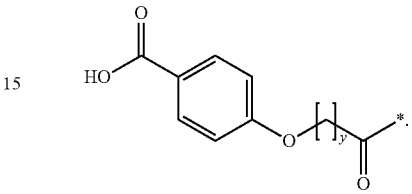

Chem. 16a

150. The derivative of any of embodiments 1-149, wherein the two protracting moieties are substantially identical.

151. The derivative of any of embodiments 1-150, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.

152. The derivative of any of embodiments 1-151, wherein the two linkers are substantially identical.

153. The derivative of any of embodiments 1-152, wherein the two linkers have a similarity of at least 0.5; preferably at least 0.6; more preferably at least 0.7, or at least 0.8; even more preferably at least 0.9; or most preferably at least 0.99, such as a similarity of 1.0.

154. The derivative of any of embodiments 1-153, wherein the two side chains consisting of protracting moiety and linker are substantially identical.

155. The derivative of any of embodiments 1-154, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.

156. The derivative of any of embodiments 151, 153, or 155, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.

157. The derivative of any of embodiments 1-156, wherein the linker is a peptide.

158. The derivative of any of embodiments 1-157, wherein the linker is a peptide comprising 5-20 amino acid residues.

159. The derivative of any of embodiments 1-158, wherein the linker is a peptide comprising 3-7 amino acid residues.

160. The derivative of any of embodiments 1-159, wherein the linker is a peptide consisting of 3-7 amino acid residues.

161. The derivative of any of embodiments 1-159, wherein the linker is a peptide consisting of 5-20 amino acid residues.

162. The derivative of any of embodiments 158 or 159, wherein the linker comprises 5, 7, 8, 13, 15, or 20 amino acid residues.

163. The derivative of embodiment 162, wherein the linker consists of 5, 7, 8, 13, 15, or 20 amino acid residues.
164. The derivative of any of embodiments 1-163, wherein the linker is attached to the epsilon-amino group of each Lys residue.
165. The derivative of any of embodiments 1-164, wherein the C-terminus of the linker is attached to the epsilon-amino group of each Lys residue.
166. The derivative of any of embodiments 1-165, wherein the protracting moiety and the linker are interconnected via an amide bond.
167. The derivative of any of embodiments 1-166, wherein the N-terminus of the linker is attached to the *—CO end of the protracting moiety.
168. A compound, preferably according to any of embodiments 1-167, selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, and Chem. 50; or a pharmaceutically acceptable salt, amide, or ester of any of Chem. 20-Chem. 50.
169. A compound characterised by its name, and selected from a listing of each of the names of the compounds of Examples 1-31 herein; or a pharmaceutically acceptable salt, amide, or ester of any of these compounds.
170. The compound of embodiment 168, which is a compound of embodiment 169.
171. A GLP-1 peptide comprising the following amino acid changes as compared to GLP-1(7-37) (SEQ ID NO: 3): (x) 8Aib, 34H, 37K; or (xii) 7Imp, 8Aib, 34R, 37K; or a pharmaceutically acceptable salt, amide, or ester of any of (x) or (xii).
172. A GLP-1 peptide which has the following amino acid changes as compared to GLP-1(7-37) (SEQ ID NO: 3): (x) 8Aib, 34H, 37K; (xii) 7Imp, 8Aib, 34R, 37K; or (xiiv) 7Imp, 8Aib, 18K, 34Q; or a pharmaceutically acceptable salt, amide, or ester of any of (x), (xii), or (xiiv).
173. The peptide of embodiment 172 which has no other amino acid modifications as compared to GLP-1(7-37) (SEQ ID NO: 3).
174. The peptide of any of embodiments 171-173, wherein the art and position of amino acid changes are as compared to GLP-1(7-37) (SEQ ID NO: 3), and are identified as described in any of embodiments 130-137.
175. The derivative of any of embodiments 1-174, which has GLP-1 activity.
176. The derivative of embodiment 175, wherein GLP-1 activity refers to the capability of activating the human GLP-1 receptor.
177. The derivative of embodiment 176, wherein activation of the human GLP-1 receptor is measured in an in vitro assay, as the potency of cAMP production.
178. The derivative of any of embodiments 1-177, which has a potency corresponding to an $EC_{50}$
a) below 3000 pM, preferably below 2600 pM, more preferably below 2400 pM, even more preferably below 2000 pM, or most preferably below 1500 pM;
b) below 1000 pM, preferably below 1600 pM, more preferably below 1400 pM, even more preferably below 1200 pM, or most preferably below 900 pM;
c) below 500 pM, preferably below 400 pM, more preferably below 300 pM, even more preferably below 250 pM, or most preferably below 200 pM; or
d) below 150 pM, preferably below 125 pM, more preferably below 100 pM, even more preferably below 60 pM, or most preferably below 50 pM.
179. The derivative of embodiment 178, wherein the potency is determined as $EC_{50}$ for stimulation of the formation of cAMP in a medium containing the human GLP-1 receptor.
180. The derivative of embodiment 179, wherein a stable transfected cell-line such as BHK467-12A (tk-ts13) is used.
181. The derivative of any of embodiments 179-180, wherein a functional receptor assay is used for the determination of cAMP.
182. The derivative of any of embodiments 179-181, wherein the assay is based on competition between endogenously formed cAMP and exogenously added biotin-cAMP.
183. The derivative of any of embodiments 179-182, wherein cAMP is captured using a specific antibody.
184. The derivative of any of embodiments 179-183, wherein the assay is the AlphaScreen cAMP assay, preferably the one described in Example 32 herein.
185. The derivative of any of embodiments 176, wherein activation of the human GLP-1 receptor is measured in a reporter gene assay.
186. The derivative of embodiment 186, wherein the reporter gene assay makes use of a stably transfected BHK cell line that expresses the human GLP-1 receptor and contains the DNA for the cAMP response element (CRE) coupled to a promoter and the gene for firefly luciferase (CRE luciferase).
187. The derivative of embodiment 186, wherein the lciferase is determined by adding luciferin, which is converted to oxyluciferin and produces bioluminescence, which is measured and is a measure of the in vitro potency.
188. The derivative of any of embodiments 185-187, wherein the assay is described in Example 33.
189. The derivative of any of embodiments 185-188, which has an in vitro potency corresponding to an $EC_{50}$ at or below 100 pM, preferably below 75 pM, more preferably below 50 pM, even more preferably below 25 pM, or most preferably below 10 pM.
190. The peptide of any of embodiments 171-174, which has GLP-1 activity as defined in any of embodiments 175-189.
191. The derivative of any of embodiments 1-189, for which the GLP-1 receptor binding affinity ($IC_{50}$) in the presence of 0.005%, preferably 0.001%, HSA (low albumin) is
a) below 50 nM, preferably below 25 nM, still more preferably below 20 nM, even more preferably below 10 nM, or most preferably below 5.0 nM; or
b) below 1.0 nM, or more preferably below 0.50 nM.
192. The derivative of embodiment 191, wherein the binding affinity to the GLP-1 receptor is measured by way of displacement of $^{125}$I-GLP-1 from the receptor, preferably using a SPA binding assay.
193. The derivative of embodiment 192, wherein the GLP-1 receptor is prepared using a stable, transfected cell line, preferably a hamster cell line, more preferably a baby hamster kidney cell line, such as BHK tk-ts13.
194. The derivative of any of embodiments 191-193, wherein the $IC_{50}$ value is determined as the concentration which displaces 50% of $^{125}$I-GLP-1 from the receptor.
195. The peptide of any of embodiments 171-174 or 190, which is capable of binding to the GLP-1 receptor as defined in any of embodiments 191-194.

196. A pharmaceutical composition comprising a peptide according to any of embodiments 171-174, 190, and/or 195, or a derivative according to any of embodiments 1-170, 175-189, and/or 191-194; and a pharmaceutically acceptable excipient.
197. A peptide according to any of embodiments 171-174, 190, and/or 195, or a derivative according to any of embodiments 1-170, 175-189, and/or 191-194; for use as a medicament.
198. A peptide according to any of embodiments 171-174, 190, and/or 195, or a derivative according to any of embodiments 1-170, 175-189, and/or 191-194; for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
199. Use of a peptide according to any of embodiments 171-174, 190, and/or 195, or a derivative according to any of embodiments 1-170, 175-189, and/or 191-194; in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
200. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a peptide according to any of embodiments 171-174, 190, and/or 195; or a derivative according to any of embodiments 1-170, 175-189, and/or 191-194.

Additional Particular Embodiments

The following are additional particular embodiments of the invention:

1. A derivative of a GLP-1 peptide which peptide comprises at least two Lys residues, wherein a protracting moiety is attached to the epsilon amino group of each Lys residue, via a linker which comprises Chem. 1:

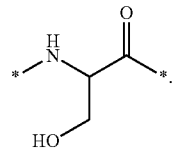

Chem. 1

2. The derivative of any of embodiments 1-2, wherein the linker further comprises Chem. 2:

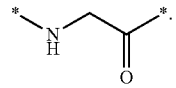

Chem. 2

3. The derivative of any of embodiments 1-2, wherein the linker comprises Chem. 3:

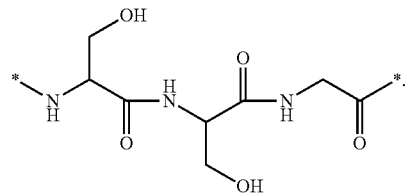

Chem. 3

4. The derivative of any of embodiments 1-3, wherein the linker comprises Chem. 4:

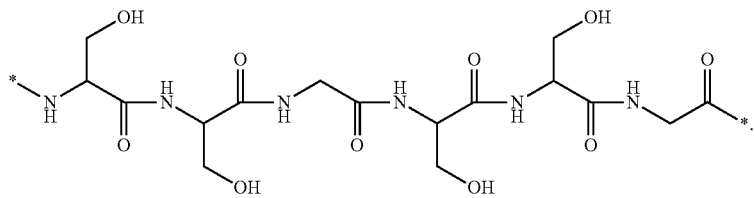

Chem. 4

5. The derivative of any of embodiments 1-4, wherein the linker further comprises Chem. 5:

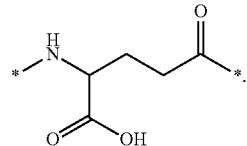

Chem. 5

6. The derivative of any of embodiments 1-5, wherein the linker comprises Chem. 6:

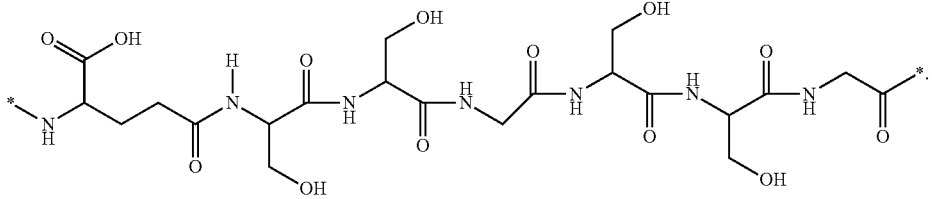

Chem. 6

7. The derivative of any of embodiments 1-6, wherein the linker consists of Chem. 6.
8. The derivative of any of embodiments 1-7 which comprises Ser.
9. The derivative of any of embodiments 1-8, wherein the linker further comprises Gly.
10. The derivative of any of embodiments 1-9, embodiment wherein the linker comprises Ser-Ser-Gly.
11. The derivative of any of embodiments 1-10, wherein the linker comprises Ser-Ser-Gly-Ser-Ser-Gly (SEQ ID NO: 1).
12. The derivative of any of embodiments 1-11, wherein the linker further comprises Glu.
13. The derivative of any of embodiments 1-12, wherein the linker comprises Glu-Ser-Ser-Gly-Ser-Ser-Gly (SEQ ID NO: 2).
14. The derivative of any of embodiments 1-3, wherein the linker consists of Glu-Ser-Ser-Gly-Ser-Ser-Gly (SEQ ID NO: 2).
15. The derivative of any of embodiments 12-14, wherein Glu is gGlu of Chem. 5.
16. The derivative of any of embodiments 1-15, wherein the GLP-1 peptide is GLP-1(7-37) (SEQ ID NO: 3) or an analogue thereof.
17. The derivative of embodiment 16, wherein the analogue has a maximum of 10 amino acid changes as compared to GLP-1(7-37) (SEQ ID NO: 3).
18. The derivative of any of embodiments 16-17, wherein the analogue has a maximum of 9 amino acid changes as compared to GLP-1(7-37) (SEQ ID NO: 3).
19. The derivative of any of embodiments 16-18, wherein the analogue has a maximum of 8 amino acid changes as compared to GLP-1(7-37) (SEQ ID NO: 3).
20. The derivative of any of embodiments 16-19, wherein the analogue has a maximum of 7 amino acid changes as compared to GLP-1(7-37) (SEQ ID NO: 3).
21. The derivative of any of embodiments 16-20, wherein the analogue has a maximum of 6 amino acid changes as compared to GLP-1(7-37) (SEQ ID NO: 3).
22. The derivative of any of embodiments 16-21, wherein the analogue has a maximum of 5 amino acid changes as compared to GLP-1(7-37) (SEQ ID NO: 3).
23. The derivative of any of embodiments 16-22, wherein the analogue has a maximum of 4 amino acid changes as compared to GLP-1(7-37) (SEQ ID NO: 3).
24. The derivative of any of embodiments 16-23, wherein the analogue has a maximum of 3 amino acid changes as compared to GLP-1(7-37) (SEQ ID NO: 3).
25. The derivative of any of embodiments 16-20, wherein the analogue has 7 amino acid changes as compared to GLP-1(7-37) (SEQ ID NO: 3).
26. The derivative of any of embodiments 16-23, wherein the analogue has 4 amino acid changes as compared to GLP-1(7-37) (SEQ ID NO: 3).
27. The derivative of any of embodiments 16-24, wherein the analogue has 3 amino acid changes as compared to GLP-1(7-37) (SEQ ID NO: 3).
28. The derivative of any of embodiments 17-27, wherein the changes are, independently, selected from substitutions, deletions, and additions.
29. The derivative of any of embodiments 17-28, wherein the changes are, independently, selected from substitutions and additions.
30. The derivative of any of embodiments 17-29, wherein the changes are substitutions.
31. The derivative of any of embodiments 1-30, wherein the GLP-1 peptide comprises a GLP-1 peptide of Formula I:

$Xaa_7$-$Xaa_8$-Glu-Gly-Thr-Phe-Thr-Ser-Asp-$Xaa_{16}$-Ser-Lys-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein    Formula I:

$Xaa_7$ is L-histidine, imidazopropionyl, α-hydroxy-histidine, D-histidine, desamino-histidine, 2-amino-histidine, β-hydroxy-histidine, homohistidine, $N^α$-acetyl-histidine, $N^α$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{16}$ is Val or Leu;
$Xaa_{18}$ is Ser or Lys;
$Xaa_{19}$ is Tyr or Gln;
$Xaa_{20}$ is Leu or Met;
$Xaa_{22}$ is Gly, Glu, Lys, or Aib; $Xaa_{23}$ is Gln, Glu, or Arg;
$Xaa_{25}$ is Ala or Val;
$Xaa_{26}$ is Val, His, Lys, or Arg;
$Xaa_{27}$ is Glu, Leu, or Lys;
$Xaa_{30}$ is Ala, Glu, Lys, or Arg;
$Xaa_{31}$ is Trp, Lys, or His;
$Xaa_{33}$ is Val or Lys;
$Xaa_{34}$ is Lys, Glu, Asn, Gly, Gln, Arg, or absent;
$Xaa_{35}$ is Gly, Aib, or absent;
$Xaa_{36}$ is Arg, Gly, Lys, or absent;
$Xaa_{37}$ is Gly, Ala, Glu, Pro, Lys, Arg, or absent; and
$Xaa_{38}$ is Ser, Gly, Ala, Glu, Pro, Lys, Arg, or absent.

32. The derivative of any of embodiments 1-31, wherein the GLP-1 peptide is a GLP-1 peptide of Formula I.
33. The derivative of any of embodiments 31-32, wherein the peptide of Formula I is an analogue of GLP-1(7-37) (SEQ ID NO: 3).
34. The derivative of any of embodiments 31-33, wherein if $Xaa_{37}$ is absent, then $Xaa_{38}$ is also absent.
35. The derivative of any of embodiments 31-34, wherein if $Xaa_{36}$ is absent, then $Xaa_{37}$, and $Xaa_{38}$ are also absent.

36. The derivative of any of embodiments 31-35, wherein if $Xaa_{35}$ is absent, then $Xaa_{36}$, $Xaa_{37}$, and $Xaa_{38}$ are also absent.
37. The derivative of any of embodiments 31-36, wherein if $Xaa_{34}$ is absent, then $Xaa_{35}$, $Xaa_{36}$, $Xaa_{37}$, and $Xaa_{38}$ are also absent.
38. The derivative of any of embodiments 31-37, wherein $Xaa_7$ is L-histidine; $Xaa_8$ is Ala or Aib; $Xaa_{16}$ is Val; $Xaa_{18}$ is Ser or Lys; $Xaa_{19}$ is Tyr; $Xaa_{20}$ is Leu; $Xaa_{22}$ is Gly or Glu; $Xaa_{23}$ is Gln; $Xaa_{25}$ is Ala or Val; $Xaa_{26}$ is Lys or Arg; $Xaa_{27}$ is Glu; $Xaa_{30}$ is Ala; $Xaa_{31}$ is Trp, Lys, or His; $Xaa_{33}$ is Val; $Xaa_{34}$ is Lys, Gln, or Arg; $Xaa_{35}$ is Gly; $Xaa_{36}$ is Arg; $Xaa_{37}$ is Gly or Lys; and $Xaa_{38}$ is Glu or absent.
39. The derivative of any of embodiments 1-38, wherein the GLP-1 peptide comprises $Aib^8$.
40. The derivative of any of embodiments 1-39, wherein the GLP-1 peptide comprises $Gln^{34}$.
41. The derivative of any of embodiments 1-40, wherein the GLP-1 peptide comprises $Arg^{34}$.
42. The derivative of any of embodiments 1-41, wherein the GLP-1 peptide comprises $Glu^{22}$.
43. The derivative of any of embodiments 1-42, wherein the GLP-1 peptide comprises two Lys residues.
44. The derivative of any of embodiments 1-43, wherein the GLP-1 peptide has only two Lys residues.
45. The derivative of any of embodiments 1-44, wherein the GLP-1 peptide comprises $Lys^{26}$ and $Lys^{37}$.
46. The derivative of any of embodiments 1-44, wherein the GLP-1 peptide comprises $Lys^{18}$ and $Lys^{26}$.
47. The derivative of any of embodiments 45 and 46, wherein the GLP-1 peptide comprises $Gln^{34}$ or $Arg^{34}$.
48. The derivative of any of embodiments 1-44, wherein the GLP-1 peptide comprises $Lys^{18}$ and $Lys^{31}$.
49. The derivative of embodiment 48, wherein the GLP-1 peptide comprises $Arg^{26}$ and $Arg^{34}$.
50. The derivative of any of embodiments 1-49, wherein the GLP-1 peptide comprises the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K; (iv) 34R, 37K, 38E; (v) 18K, 22E, 34Q; (vi) 8Aib, 18K, 22E, 25V, 26R, 31K, 34R; (vii) 8Aib, 18K, 22E, 34Q; (iix) 8Aib, 18K, 22E, 34Q; (ix) 8Aib, 18K, 34Q, 37K; or (x) 8Aib, 34Q, 37K.
51. The derivative of any of embodiments 1-50, wherein the GLP-1 peptide has the following amino acid changes, as compared to GLP-1(7-37) (SEQ ID NO: 3): (i) 8Aib, 34R, 37K; (ii) 8Aib, 31H, 34Q, 37K; (iii) 31H, 34Q, 37K; (iv) 34R, 37K, 38E; (v) 18K, 22E, 34Q; (vi) 8Aib, 18K, 22E, 25V, 26R, 31K, 34R; (vii) 8Aib, 18K, 22E, 34Q; (iix) 8Aib, 18K, 22E, 34Q; (ix) 8Aib, 18K, 34Q; or (x) 8Aib, 34Q, 37K.
52. The derivative of any of embodiments 1-51, wherein the number of amino acid changes as compared to GLP-1(7-37) (SEQ ID NO: 3) are identified by handwriting and eyeballing.
53. The derivative of any of embodiments 1-52, wherein the art and position of amino acid changes are as compared to GLP-1(7-37) (SEQ ID NO: 3), and are identified by handwriting and eyeballing.
54. The derivative of any of embodiments 1-53, wherein the art and position of amino acid changes are as compared to GLP-1(7-37) (SEQ ID NO: 3), and are identified by use of a standard protein or peptide alignment program.
55. The derivative of embodiment 54, wherein the alignment program is a Needleman-Wunsch alignment.
56. The derivative of any of embodiments 54-55, wherein the default scoring matrix and the default identity matrix is used.
57. The derivative of any of embodiments 54-56, wherein the scoring matrix is BLOSUM62.
58. The derivative of any of embodiments 54-57, wherein the penalty for the first residue in a gap is −10 (minus ten).
59. The derivative of any of embodiments 54-58, wherein the penalties for additional residues in a gap is −0.5 (minus point five).
60. The derivative of any of embodiments 1-59, wherein the protracting moiety is selected from Chem. 15 and Chem. 16:

$$HOOC-(CH_2)_x-CO-* \qquad \text{Chem. 15:}$$

$$HOOC-C_6H_4-O-(CH_2)_y-CO-*, \qquad \text{Chem. 16:}$$

in which x is an integer in the range of 6-18, and y is an integer in the range of 3-11.
61. The derivative of embodiment 60, wherein x is an even number.
62. The derivative of any of embodiments 60-61, wherein x is 12.
63. The derivative of any of embodiments 60-62, wherein y is an odd number.
64. The derivative of any of embodiments 60-63, wherein y is 7, 9, or 11.
65. The derivative of any of embodiments 60-64, wherein y is 9.
66. The derivative of any of embodiments 60-62, wherein y is an even number.
67. The derivative of embodiment 66, wherein y is 10.
68. The derivative of any of embodiments 60-67, wherein the protracting moiety is Chem. 15.
69. The derivative of any of embodiments 60-67, wherein the protracting moiety is Chem. 16.
70. The derivative of any of embodiments 60-68, wherein Chem. 15 is represented by Chem. 15a:

Chem. 15a

71. The derivative of embodiments 60-67 and 69, wherein Chem. 16 is represented by Chem. 16a:

Chem. 16a

72. The derivative of any of embodiments 1-71, wherein the at least two protracting moieties are substantially identical.
73. The derivative of any of embodiments 1-72, wherein the at least two protracting moieties have a similarity of at least 0.5; preferably at least 0.6; more preferably at least 0.7, or at least 0.8; even more preferably at least 0.9; or most preferably at least 0.99, such as a similarity of 1.0.

74. The derivative of any of embodiments 1-73, wherein the at least two linkers are substantially identical.
75. The derivative of any of embodiments 1-74, wherein the at least two linkers have a similarity of at least 0.5; preferably at least 0.6; more preferably at least 0.7, or at least 0.8; even more preferably at least 0.9; or most preferably at least 0.99, such as a similarity of 1.0.
76. The derivative of any of embodiments 1-75, wherein the at least two side chains consisting of protracting moiety and linker are substantially identical.
77. The derivative of any of embodiments 1-76, wherein the at least two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.
78. The derivative of any of embodiments 73, 75, and 77, wherein the at least two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
79. The derivative of any of embodiments 1-78, wherein the linker is a peptide.
80. The derivative of any of embodiments 1-79, wherein the linker is a peptide comprising 3-7 amino acid residues.
81. The derivative of any of embodiments 1-80, wherein the linker is a peptide consisting of 3-7 amino acid residues.
82. The derivative of any of embodiments 1-81, wherein the linker is attached to the epsilon-amino group of each Lys residue.
83. The derivative of any of embodiments 1-82, wherein the C-terminus of the linker is attached to the epsilon-amino group of each Lys residue.
84. The derivative of any of embodiments 1-83, wherein the protracting moiety and the linker are interconnected via an amide bond.
85. The derivative of any of embodiments 1-84, wherein the N-terminus of the linker is attached to the *—CO end of the protracting moiety.
86. A compound, preferably according to any of embodiments 1-85, selected from the following: Chem. 20, Chem. 21, Chem. 22, Chem. 23, Chem. 24, Chem. 25, Chem. 26, Chem. 27, Chem. 28, and Chem. 29; or a pharmaceutically acceptable salt, amide, or ester thereof.
87. A compound characterised by its name, and selected from a listing of each of the names of the compounds of Examples 1-10 herein; or a pharmaceutically acceptable salt, amide, or ester thereof.
88. The compound of embodiment 86, which is a compound of embodiment 87.
89. The derivative of any of embodiments 1-82, which has GLP-1 activity.
90. The derivative of embodiment 89, wherein GLP-1 activity refers to the capability of activating the human GLP-1 receptor.
91. The derivative of embodiment 90, wherein activation of the human GLP-1 receptor is measured in an in vitro assay, as the potency of cAMP production.
92. The derivative of any of embodiments 1-91, which has a potency corresponding to an $EC_{50}$
a) below 500 pM, preferably below 400 pM, more preferably below 300 pM, even more preferably below 250 pM, or most preferably below 200 pM; or
b) below 150 pM, preferably below 125 pM, more preferably below 100 pM, even more preferably below 60 pM, or most preferably below 50 pM.
93. The derivative of embodiment 92, wherein the potency is determined as $EC_{50}$ for stimulation of the formation of cAMP in a medium containing the human GLP-1 receptor.
94. The derivative of embodiment 93, wherein a stable transfected cell-line such as BHK467-12A (tk-ts13) is used.
95. The derivative of any of embodiments 93-94, wherein a functional receptor assay is used for the determination of cAMP.
96. The derivative of any of embodiments 93-95, wherein the assay is based on competition between endogenously formed cAMP and exogenously added biotin-labelled cAMP.
97. The derivative of any of embodiments 93-96, wherein cAMP is captured using a specific antibody.
98. The derivative of any of embodiments 93-97, wherein the assay is the AlphaScreen cAMP Assay, preferably the one described in Example 11 herein.
99. The derivative of any of embodiments 1-98, for which the GLP-1 receptor binding affinity ($IC_{50}$) in the presence of 0.005% HSA (low albumin) is
a) below 50 nM, preferably below 25 nM, still more preferably below 20 nM, even more preferably below 10 nM, or most preferably below 5.0 nM; or
b) below 1.0 nM, or more preferably below 0.50 nM.
100. The derivative of embodiment 99, wherein the binding affinity to the GLP-1 receptor is measured by way of displacement of $^{125}$I-GLP-1 from the receptor, preferably using a SPA binding assay.
101. The derivative of embodiment 100, wherein the GLP-1 receptor is prepared using a stable, transfected cell line, preferably a hamster cell line, more preferably a baby hamster kidney cell line, such as BHK tk-ts13.
102. The derivative of any of embodiments 99-101, wherein the $IC_{50}$ value is determined as the concentration which displaces 50% of $^{125}$I-GLP-1 from the receptor.
103. A pharmaceutical composition comprising a derivative according to any of embodiments 1-102, and a pharmaceutically acceptable excipient.
104. A derivative according to any of embodiments 1-102, for use as a medicament.
105. A derivative according to any of embodiments 1-102, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
106. Use of a derivative according to any of embodiments 1-92 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
107. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-102.

The following are still further particular embodiments of the invention:

i). A derivative of a GLP-1 peptide which peptide comprises at least two Lys residues, wherein a protracting moiety is attached to the epsilon amino group of each Lys residue, via a linker which comprises Chem. 1:

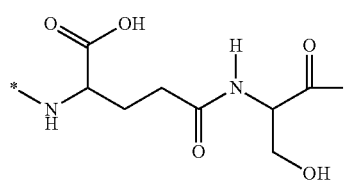

ii). The derivative of any of embodiments 1-2, wherein the linker further comprises Chem. 2:

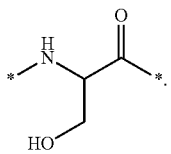

iii). The derivative of any of embodiments i)-ii), wherein the linker comprises Chem. 3:

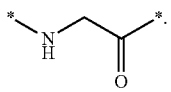

iv). The derivative of any of embodiments i)-iii) wherein the linker comprises Chem. 4:

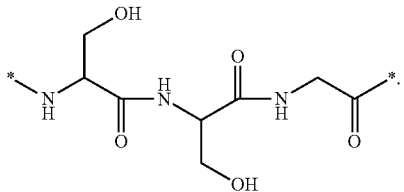

v). The derivative of any of embodiments i)-iv), wherein the linker further comprises Chem. 5:

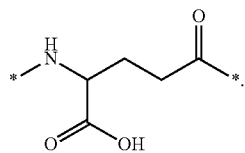

vi). The derivative of any of embodiments i)-v), wherein the linker comprises Chem. 6:

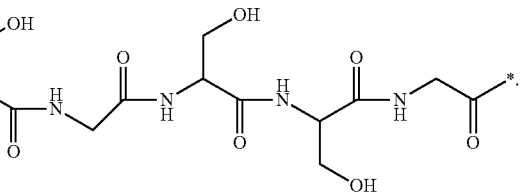

vii). The derivative of any of embodiments i)-vi), wherein the GLP-1 peptide is GLP-1(7-37) (SEQ ID NO: 3) or an analogue thereof having a maximum of 10 amino acid changes as compared to GLP-1(7-37) (SEQ ID NO: 3).

iix). The derivative of any of embodiments i)-vii), wherein the protracting moiety is selected from Chem. 15 and Chem. 16:

HOOC—(CH₂)$_x$—CO—*   Chem. 15:

HOOC—C₆H₄—O—(CH₂)$_y$—CO—*,   Chem. 16:

in which x is an integer in the range of 6-18, and y is an integer in the range of 3-11.

ix). A compound selected from the following: Chem. 20, Chem. 21, Chem. 22, Chem. 23, Chem. 24, Chem. 25, Chem. 26, Chem. 27, Chem. 28, and Chem. 29; or a pharmaceutically acceptable salt, amide, or ester thereof.

x). A pharmaceutical composition comprising a derivative according to any of embodiments i)-ix), and a pharmaceutically acceptable excipient.

xi). A derivative according to any of embodiments i)-ix), for use as a medicament.

xii). A derivative according to any of embodiments i)-ix), for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

xiii). Use of a derivative according to any of embodiments i)-ix) in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

xiv). A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments i)-ix).

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.
List Of Abbreviations
Aib: α-aminoisobutyric acid
API: Active Pharmaceutical Ingredient
AUC: Area Under the Curve
BHK Baby Hamster Kidney
Boc: t-butyloxycarbonyl
BSA: Bovine serum albumin
CAS: Chemical Abstracts Service
Clt: 2-chlorotrityl
collidine: 2,4,6-trimethylpyridine
DCM: dichloromethane
DesH: des-amino histidine (may also be referred to as imidazopropionic acid, Imp)
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HPLC: High Performance Liquid Chromatography
HSA: Human Serum Albumin
I BMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
LCMS: Liquid Chromatography Mass Spectroscopy
MALDI-MS: See MALDI-TOF MS
MALDI-TOF MS: Matrix-Assisted Laser Desorption/lonisation Time of Flight Mass Spectroscopy
MeOH: methanol
Mmt: 4-methoxytrityl
Mtt: 4-methyltrityl
NMP: N-methyl pyrrolidone
OEG: 8-amino-3,6-dioxaoctanic acid
OtBu: tert butyl ester
Pbf: 2,2,4,6,7-pentamethyldihydrobenzofuran-5-sulfonyl
PBS: Phosphate Buffered Saline
Pen/Strep: Pencillin/Streptomycin
RP: Reverse Phase
RP-HPLC: Reverse Phase High Performance Liquid Chromatography
RT: Room Temperature
Rt: Retention time
s.c.: Subcutaneously
SEC-HPLC: Size Exclusion High Performance Liquic Chromatography
SPA: Scintillation Proximity Assay
SPPS: Solid Phase Peptide Synthesis
tBu: tert. butyl
TFA: trifluoroacetic acid
TIS: triisopropylsilane
Tris: tris(hydroxymethyl)aminomethane or 2-amino-2-hydroxymethyl-propane-1,3-diol
UPLC: Ultra Performance Liquid Chromatography
Materials and Methods
Materials
N-α,N-β-Di-Fmoc-L-2,3-Diaminopropionic Acid (CAS 201473-90-7)
3,5-Di-tert-butyl-4-hydroxybenzoic acid (CAS 1421-49-4)
3,5-Di-tert-butylbenzoic Acid (CAS 16225-26-6)
Fmoc-8-amino-3,6-dioxaoctanoic acid (CAS 166108-71-0)
17-(9-Fluorenylmethyloxycarbonyl-amino)-9-aza-3,6,12,15-tetraoxa-10-on-heptadecanoic acid (IRIS Biotech GmbH)
Fmoc-L-Glutamic acid 1-tert-butyl ester (CAS 84793-07-7)
2-(2-Methoxyethoxy)acetic acid (CAS 16024-56-9)
N-α,N-ε-Bis(9-fluorenylmethyloxycarbonyl)-L-lysine (CAS 78081-87-5) 1-[(9H-fluoren-9-ylmethoxy)carbonyl]piperidine-4-carboxylic acid (CAS 148928-15-8)
FMOC-8-Aminocapryl acid (CAS 126631-93-4)
FMOC-6-Aminohexanoic acid (CAS 88574-06-5)
FMOC-12-Aminododecanoic acid (CAS 128917-74-8)
4-(9-carboxy-nonyloxy)-benzoic acid tert-butyl ester (prepared as described in Example 25, step 1 and 2 of WO 2006/082204)
4-(8-Carboxy-octyloxy)-benzoic acid tert-butyl ester (M.p.: 71-72° C.
$^1$H NMR (300 MHz, CDCl$_3$, δ$_H$): 7.93 (d, J=8.9 Hz, 2 H); 6.88 (d, J=8.9 Hz, 2 H); 4.00 (t, J=6.4 Hz, 2 H); 2.36 (t, J=7.4 Hz, 2 H); 1.80 (m, 2 H); 1.65 (m, 2 H); 1.59 (s, 9 H); 1.53-1.30 (m, 8 H) (prepared as described in Example 25, step 1 and 2 of WO 2006/082204, replacing methyl 10-bromodecanoate with ethyl 9-Bromononanoate (CAS 28598-81-4))
4-(7-Carboxy-heptyloxy)-benzoic acid tert-butyl ester ($^1$H NMR spectrum (300 MHz, CDCl$_3$, δ$_H$): 7.93 (d, J=9.0 Hz, 2 H); 6.88 (d, J=9.0 Hz, 2 H); 4.00 (t, J=6.5 Hz, 2 H); 2.37 (t, J=7.4 Hz, 2 H); 1.80 (m, 2 H); 1.64 (m, 2 H); 1.59 (s, 9 H); 1.53-1.33 (m, 6 H)) (prepared as described in Example 25, step 1 and 2 of WO 2006/082204, replacing methyl 10-bromodecanoate with ethyl 7-bromoheptanoate (CAS 29823-18-5))
Chemical Methods This section is divided in two: Section A relating to general methods (of preparation (A1); and of detection and characterisation (A2)), and section B, in which the preparation and characterisation of a number of specific example compounds is described.

A. General Methods
A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn (Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp (Boc)-OH, Fmoc-Tyr(tBu)-OH, or, Fmoc-Val-OH etc. supplied from e.g. Anaspec, Bachem, Iris Biotech, or Novabiochem. Were nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-μmol synthesis scale.

1. Synthesis of Resin Bound Protected Peptide Backbone

Method: SPPS_A

The protected peptidyl resin was synthesised according to the Fmoc strategy on an Applied Biosystems 433 peptide synthesiser in a 250-μmol or 1000 μmol scale with three or four fold excess of Fmoc-amino acids, using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP and UV monitoring of the deprotection of the Fmoc protection group, in some cases double couplings were used, meaning that after the first coupling, the resin is drained and more Fmoc-amino acids and reagents are added. The starting resin used for the synthesis of the peptide amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem) supplied in preweighed cartridges suitable for the ABI433A synthesiser with the exception of unnatural aminoacids such as Fmoc-Aib-OH (Fmoc-aminoisobutyric acid). The N terminal amino acid was Boc protected at the alpha amino group (e.g. Boc-His(Boc)-OH or Boc-His(Trt)-OH was used for peptides with His at the N-terminal). The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2009/2010 or newer version, or W. R. Sampson (1999), J. Pep. Sci. 5, 403).

Method: SPPS_P

SPPS_P was performed on a Prelude Solid Phase Peptide Synthesizer from Protein Technologies (Tucson, Ariz. 85714 U.S.A.) at 250-μmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_CS

The peptide backbone was synthesised according to standard Fmoc strategy on a custom-built CS Bio peptide synthesiser in a 250-μmol to 6000 μmol scale with four fold excess of preactivated Fmoc-amino acids, using protocols which employ ethyl 2-cyano-2-(hydroxyimino)acetate and diisopropylcarbodiimide mediated couplings in NMP. UV monitoring was employed to ensure complete Fmoc-deprotection by treatment with 20% piperidine in NMP. In some cases double couplings were used, meaning that after the first coupling, the resin is drained and more preactivated Fmoc-amino acid is added. The starting resin used for the synthesis of the peptide amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem). The N terminal amino acid was Boc protected at the alpha amino group (e.g. Boc-His(Boc)-OH or Boc-His(Trt)-OH were used for peptides with His at the N-terminal). The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such as but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2011/2012 or newer version, or W. R. Sampson (1999), J. Pep. Sci. 5, 403).

Method: SPPS_L

SPPS_L was performed on a microwave-based Liberty peptide synthesiser from CEM Corp. (Matthews, N.C. 28106, U.S.A.) at 250-μmol or 100-μmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Side Chains

Mono Esters of Fatty Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation.

3. Attachment of Side Chains to Resin Bound Protected Peptide Backbone

When an acylation is present on a lysine side chain, the epsilon amino group of lysine to be acylated was protected either with Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

If N-ε-lysine protection group was Mtt, the Mtt group was removed with neat HFIP (3×15 min) followed by washings with DCM and the acylation performed on a Prelude peptide synthesiser ((10 eq. Fmoc-AA, 10 eq. DIC and 10 eq. HOAt, 10 eq. collidine 30 min and 25% piperidine in NMP to remove the Fmoc-group). Fmoc-Glu-OtBu was double coupled for 4 hours. The terminal residue was attached using similar conditions.

Method: SC_A

If N-ε-lysine protection group was Mtt, the Mtt-deprotection was performed by treatment with hexafluoroisopropanol (5-10 ml×2, each 10 min, 0.12-0.25 mmol scale) followed by washings with DCM (8 ml×6). The Fmoc amino acids and the albumin binding moiety were attached to the peptide by acylation of the resin bound peptide using the Fmoc strategy on an Applied Biosystems 433 peptide synthesiser in a 125-μmol or 250 μmol scale with four fold excess of Fmoc-amino acids and the albumin binding moiety, using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone) and UV monitoring of the deprotection of the Fmoc protection group, in some cases double couplings were used.

Method: SC_CS

The N-ε-lysine protection group was removed as described above. The chemical modification of the lysine residue was synthesised according to standard Fmoc strategy on a custom-built CS Bio peptide synthesiser in a 250-μmol to 6000 μmol scale with four fold excess of preactivated Fmoc-amino acids, using protocols which employ ethyl 2-cyano-2-(hydroxyimino)acetate and diisopropylcarbodiimide mediated couplings in NMP. UV monitoring was employed to ensure complete Fmoc-deprotection by treatment with 20% piperidine in NMP. In some cases double couplings were used, meaning that after the first coupling, the resin is drained and more preactivated Fmoc-amino acid is added. The protected amino acid derivatives used were standard Fmoc-amino acids (supplied from e.g. Anaspec, or Novabiochem) or synthetic acids made by conventional organic synthesis.

4. Clevage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 μM column, using acetonitrile/water/TFA. The fractions were analysed by a combination of UPLC, MALDI and LCMS methods, and the appropriate fractions were pooled and lyophilised.

A2. General Methods for Detection and Characterisation

1. LC-MS Methods

Method: LCMS_4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 μl) onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES
Scan: 100-2000 amu (alternatively 500-2000 amu), step 0.1 amu.

Method: LCMS_AP

LCMS_AP was performed using a Micromass Quatro micro API mass spectrometer to identify the mass of the sample after elution from a HPLC system composed of Waters 2525 binary gradient modul, Waters 2767 sample manager, Waters 2996 Photodiode Array Detector and Waters 2420 ELS Detector. Eluents: A: 0.1% Trifluoro acetic acid in water; B: 0.1% Trifluoro acetic acid in acetonitrile. Column: Phenomenex Synergi MAXRP, 4 um, 75×4.6 mm. Gradient: 5%-95% B over 7 min at 1.0 ml/min.

2. UPLC methods

Method: B5_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40°

C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 60% A, 40% B to 30% A, 70% B over 8 minutes at a flow-rate of 0.40 ml/min.

Method: B7_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 80% A, 20% B to 40% A, 60% B over 8 minutes at a flow-rate of 0.40 ml/min.

Method: A3_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 75% A, 25% B to 45% A, 55% B over 16 minutes at a flow-rate of 0.40 ml/min.

Method: A6_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 10% A, 90% B over 16 minutes at a flow-rate of 0.35 ml/min.

Method: B2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.

Method: B14_1

The RP-analyses was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.

Method: B31_1

The RP-analysis was performed using a Waters UPLC system fitted with a dual band detector. UV detections at 215 nm and 254 nm were collected using an kinetex 1.7 u C18, 100A 2.1×150 mm column, 60° C. The UPLC system was connected to two eluent reservoirs containing: A: 90% water and 10% MeCN with 0.045M $(NH_4)_2HPO_4$, pH 3.6, B: 20% isopropanole, 20% water and 60% $CH_3CN$. The following step gradient was used: 25% B and 75% A over 2 minutes, then 25% B, 75% A to 55% B, 45% A over 15 minutes, then 55% B, 45% A to 80% B, 20% A over 3 minutes at a flowrate of 0.5 ml/min.

Method: AP_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 30° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.30 ml/min.

Method: B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.40 ml/min.

Method: B29_1

The RP-analysis was performed using a Waters UPLC system fitted with a dual band detector. UV detections at 215 nm and 254 nm were collected using a Kinetex 1.7 μm C18, 100 Å, 2.1×150 mm column, at 60° C. The UPLC system was connected to two eluent reservoirs containing: A: 90% water and 10% $CH_3CN$ with 0.09M $(NH_4)_2HPO_4$, pH 3.6; B: 20% isopropanol, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flowrate of 0.5 ml/min.

3. MALDI-MS Method

Method: MALDI_MS

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Specific Example Compounds

Example 1

$N^{\varepsilon 26}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\varepsilon 37}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Arg$^{34}$,Lys$^{37}$]-GLP-1-(7-37)-peptide Chem. 20:

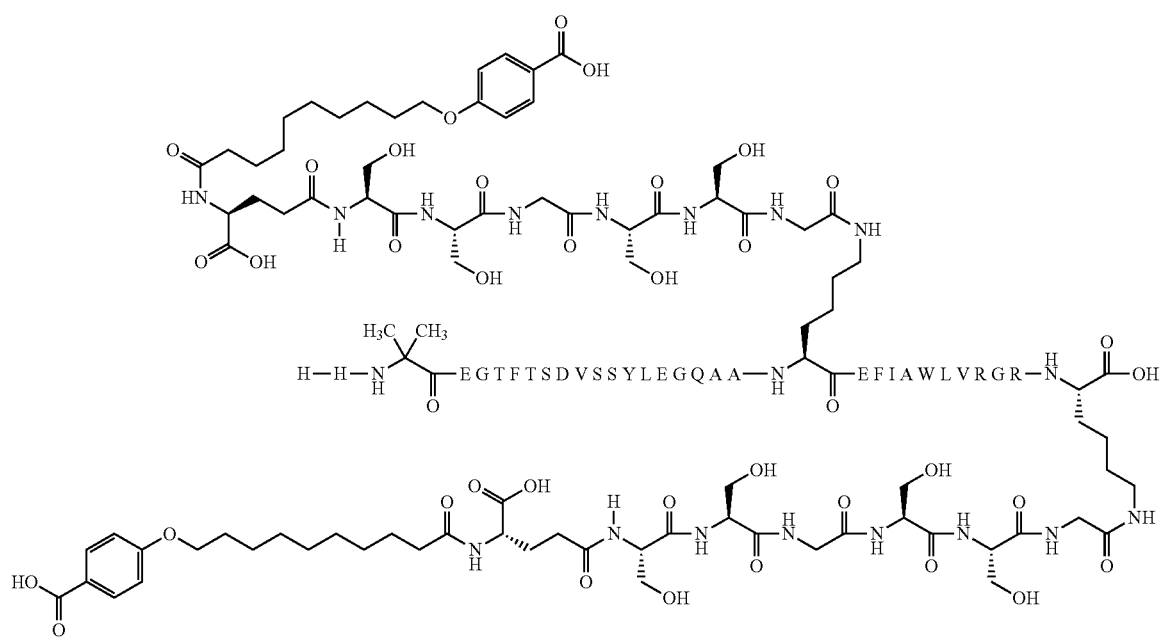

Preparation method: SPPS_A, SC_A, CP_M1
UPLC Method: B2_1: Rt=12.52 min
UPLC Method: B5_1: Rt=5.50 min
UPLC Method: A3_1: Rt=9.20 min
LCMS Method: LCMS_4: Rt=2.22 min; m/3:1744; m/4: 1308; m/5:1347

Example 2

$N^{\epsilon26}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\epsilon37}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,His$^{31}$,Gln$^{34}$,Lys$^{37}$]-GLP-1-(7-37)-peptide Chem. 21:

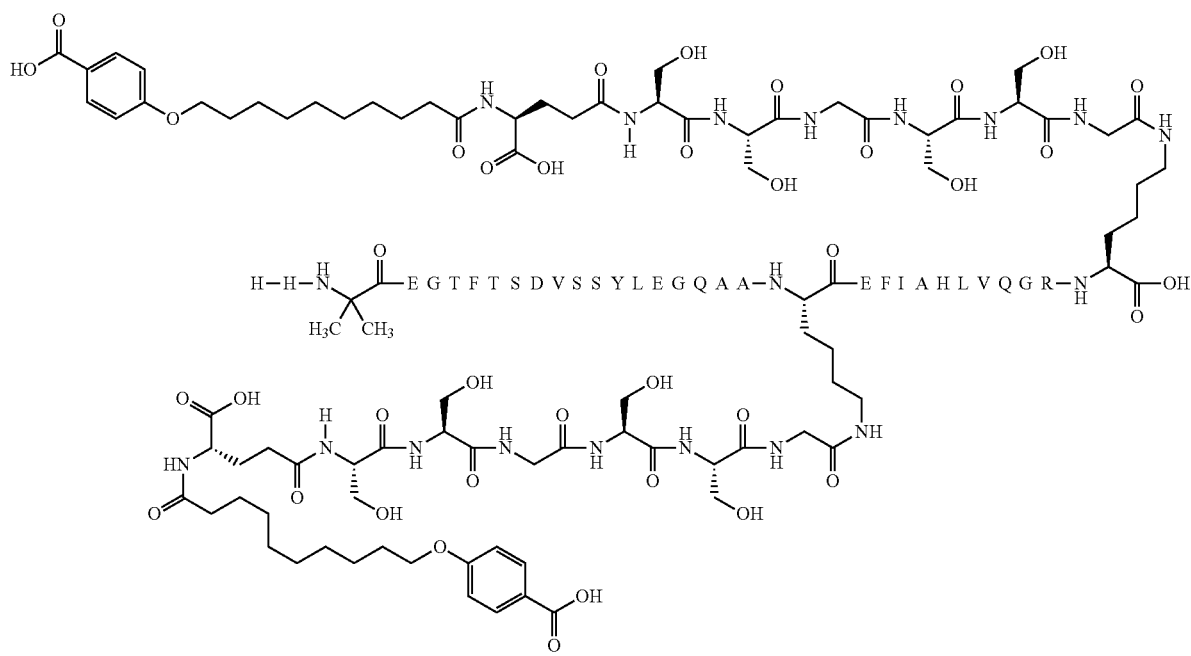

Preparation method: SPPS_A, SC_A, CP_M1
UPLC Method: B2_1: Rt=11.57 min
UPLC Method: B7_1: Rt=7.74 min
UPLC Method: A3_1: Rt=6.56 min
LCMS Method: LCMS_4: Rt=1.98 min; m/3:1718; m/4: 1289; m/5:1032

Example 3

N^ε26^-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],N^ε37^-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[His$^{31}$,Gln$^{34}$,Lys$^{37}$]-GLP-1-(7-37)-peptide Chem. 22:

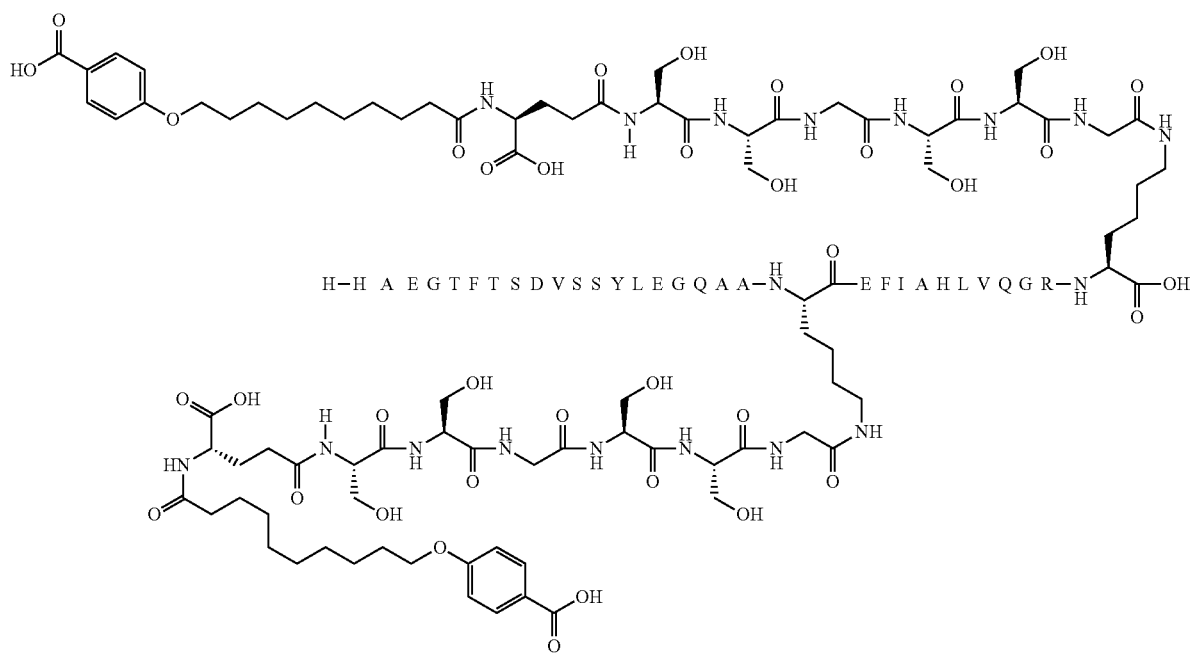

Preparation method: SPPS_A, SC_A, CP_M1
UPLC Method: B14_1: Rt=5.39 min
UPLC Method: A6_1: Rt=4.15 min
LCMS Method: LCMS_4: Rt=1.98 min; m/3:1713; m/4: 1285; m/5:1028

Example 4

N^ε26^-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],N^ε37^-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Arg$^{34}$,Lys$^{37}$]-GLP-1-(7-37)-peptidyl-Glu Chem. 23:

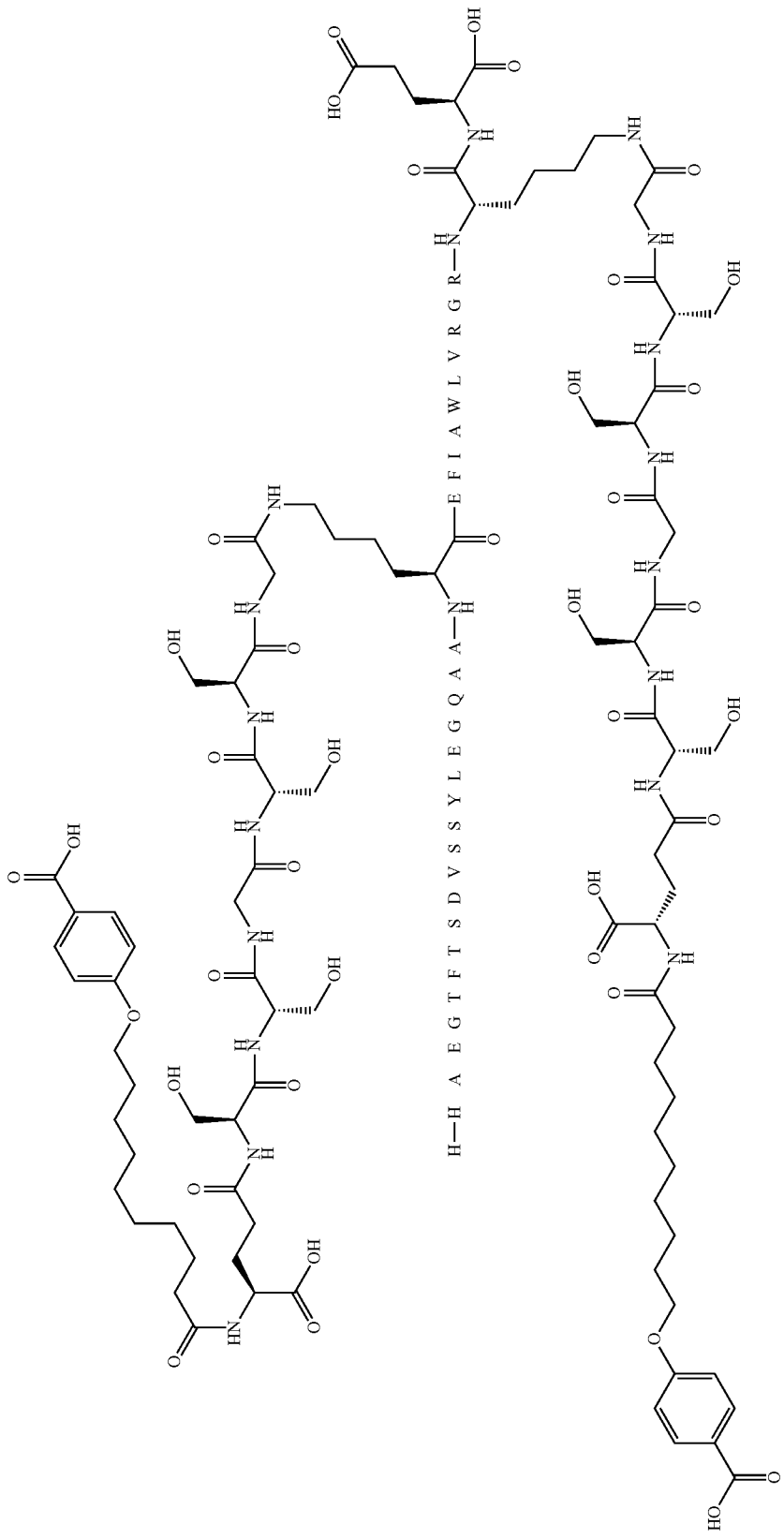

Preparation method: SPPS_A, SC_A, CP_M1
UPLC Method: B14_1: Rt=10.77 min
UPLC Method: A6_1: Rt=4.13 min
LCMS Method: LCMS_4: Rt=2.06 min; m/3:1783; m/4: 1337; m/5:1070

Example 5

$N^{\varepsilon 18}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\varepsilon 26}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[$Lys^{18}$,$Glu^{22}$,$Gln^{34}$]-GLP-1-(7-37)-peptide Chem. 24:

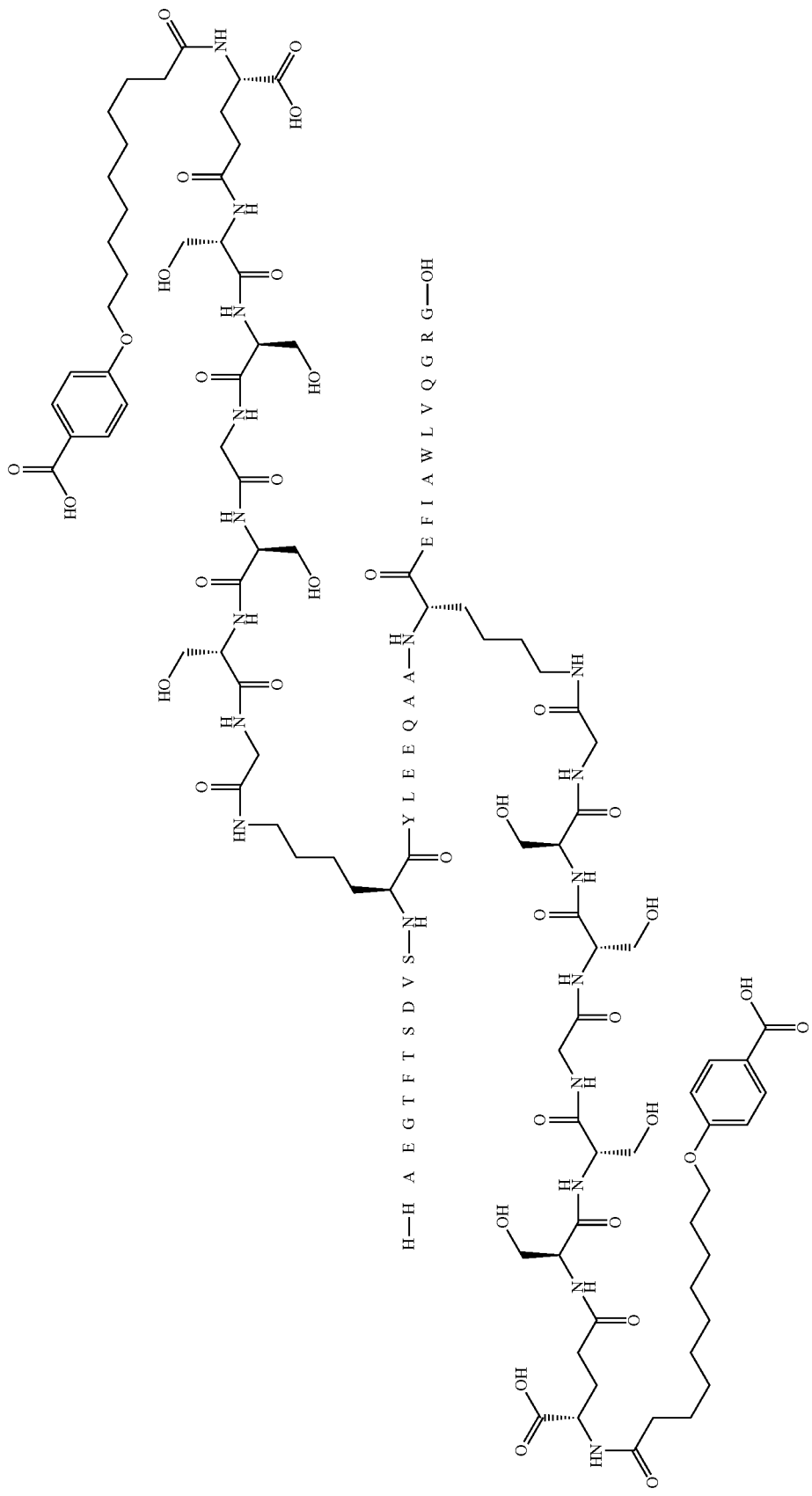

Preparation method: SPPS_A, SC_A, CP_M1
UPLC Method: B14_1: Rt=6.77 min
UPLC Method: A6_1: Rt=9.03 min
LCMS Method: LCMS_4: Rt=2.06 min; m/3:1744; m/4: 1308; m/5:1047

Example 6

$N^{\varepsilon 18}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\varepsilon 31}$-[2-[[(2S)-2-[[(2S)-2-[[2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide Chem. 25:

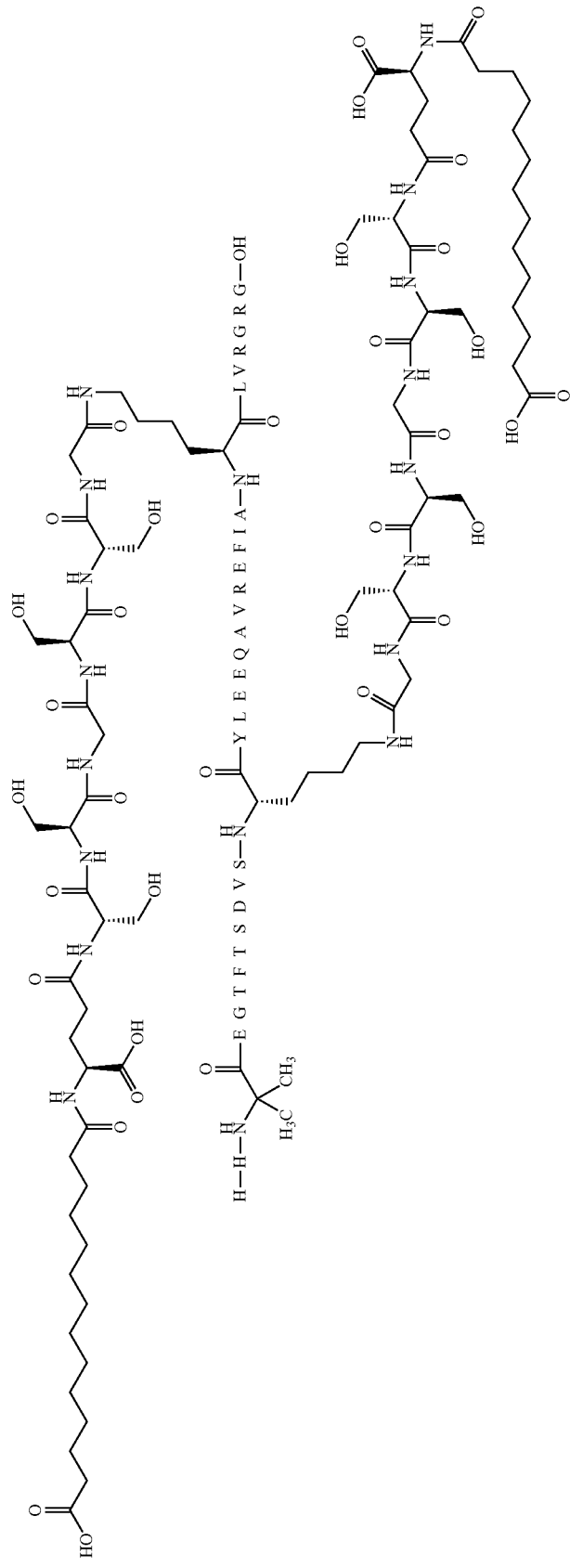

Preparation method: SPPS_A, SC_A, CP_M1
UPLC Method: B14_1: Rt=4.83 min
UPLC Method: A6_1: Rt=5.45 min
LCMS Method: LCMS_4: Rt=1.94 min; m/3:1725; m/4: 1294; m/5:1035

Example 7

$N^{\epsilon18}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\epsilon26}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Glu$^{22}$,Gln$^{34}$]-GLP-1-(7-37)-peptide Chem. 26:

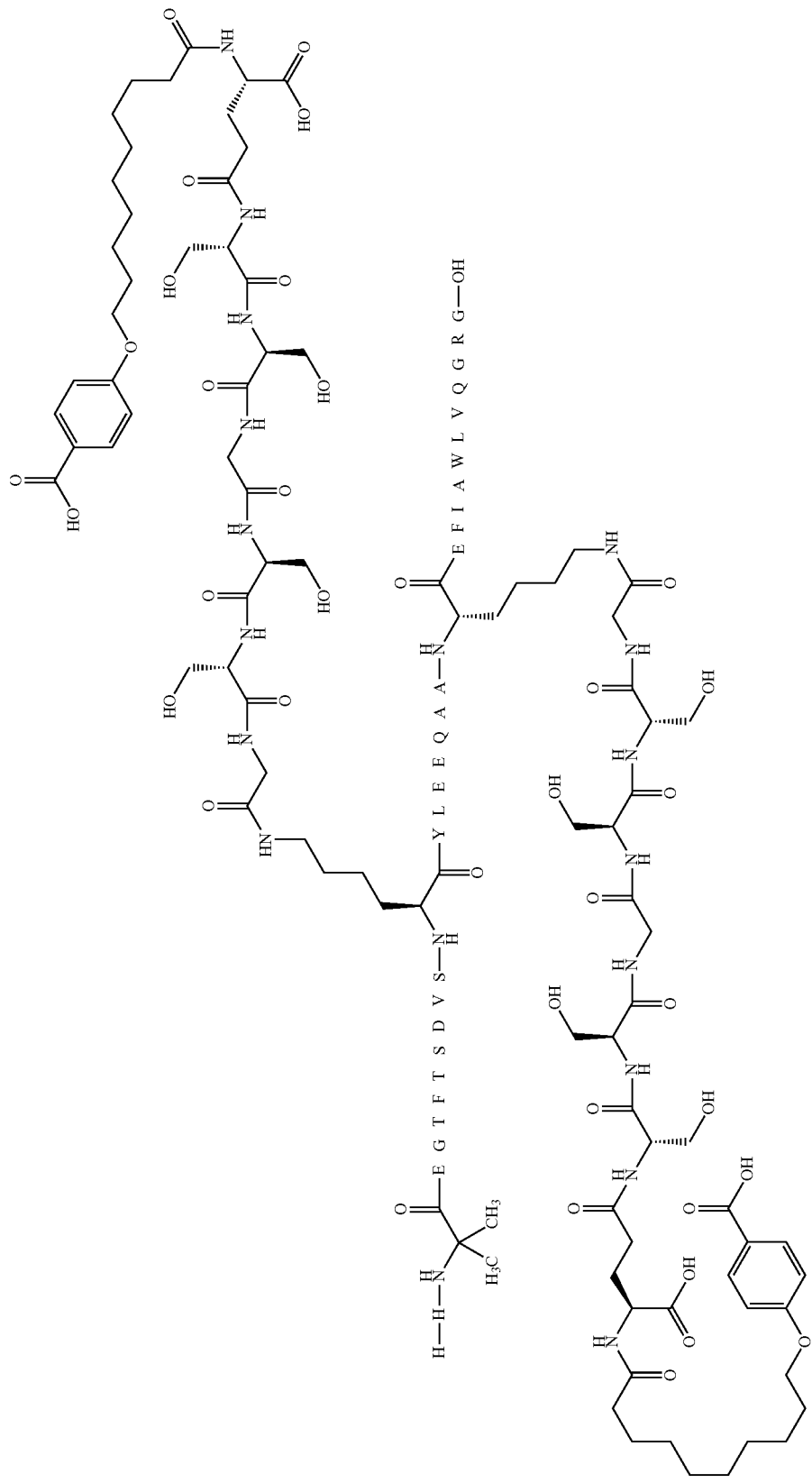

Preparation method: SPPS_A, SC_A, CP_M1
UPLC Method: B14_1: Rt=6.69 min,
LCMS Method: LCMS_4: Rt=2.27 min; m/3:1749; m/4: 1312; m/5:1050

Example 8

$N^{\varepsilon 18}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\varepsilon 26}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Glu$^{22}$,Gln$^{34}$]-GLP-1-(7-37)-peptide Chem. 27:

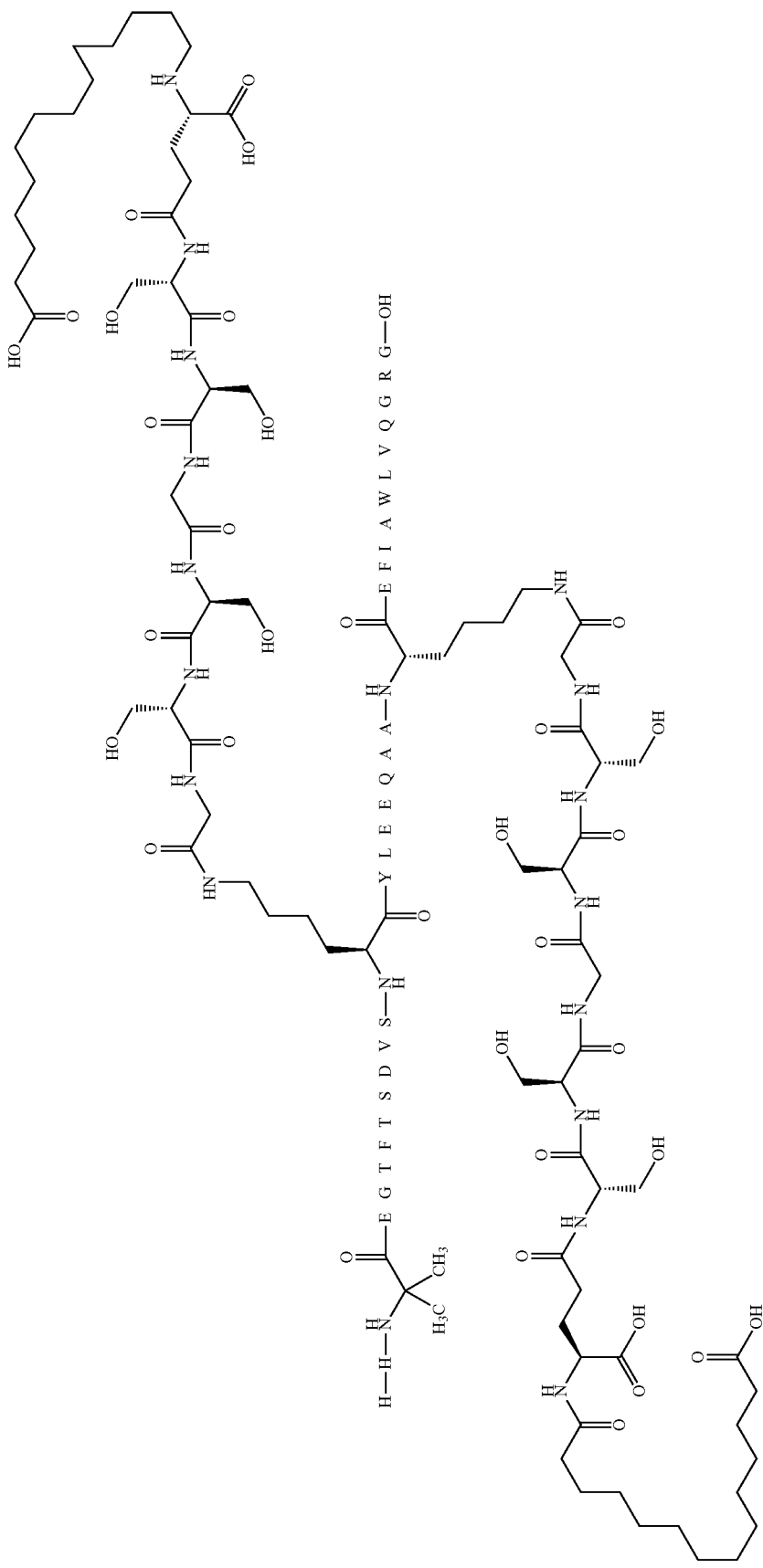

Preparation method: SPPS_A, SC_A, CP_M1
UPLC Method: B14_1: Rt=6.46 min
LCMS Method: LCMS_4: Rt=2.29 min; m/3:1716; m/4: 1287; m/5:1030

Example 9

$N^{\varepsilon 18}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\varepsilon 26}$-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Gln$^{34}$]-GLP-1-(7-37)-peptide Chem. 28:

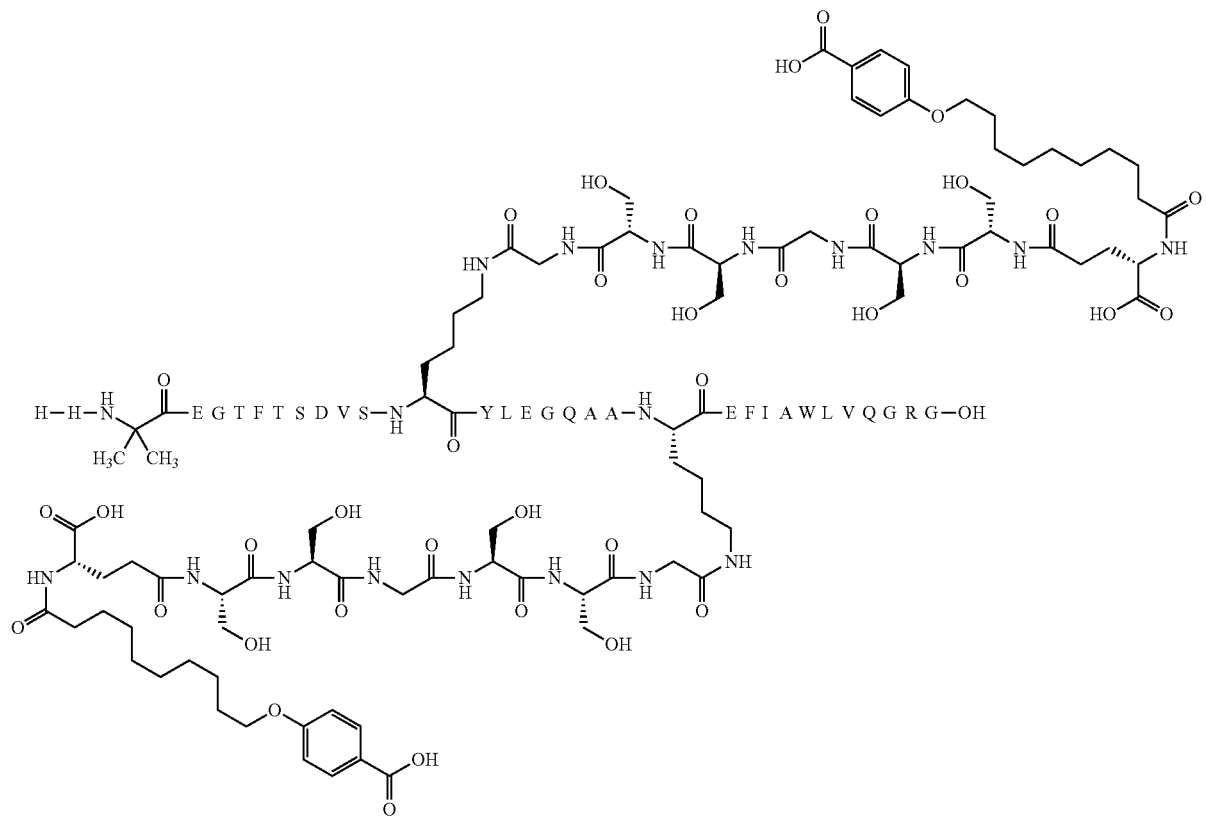

Preparation method: SPPS_P, SC_P, CP_M1
UPLC Method: B31_1: Rt=14.9 min
UPLC Method: A6_1: Rt=4.9 min
The theoretical molecular mass of Mw 5174 was confirmed by:
Method: Maldi_MS: 5173

Example 10

$N^{\epsilon 26}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl],$N^{\epsilon 37}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Gln$^{34}$,Lys$^{37}$]-GLP-1-(7-37)-peptide Chem. 29:

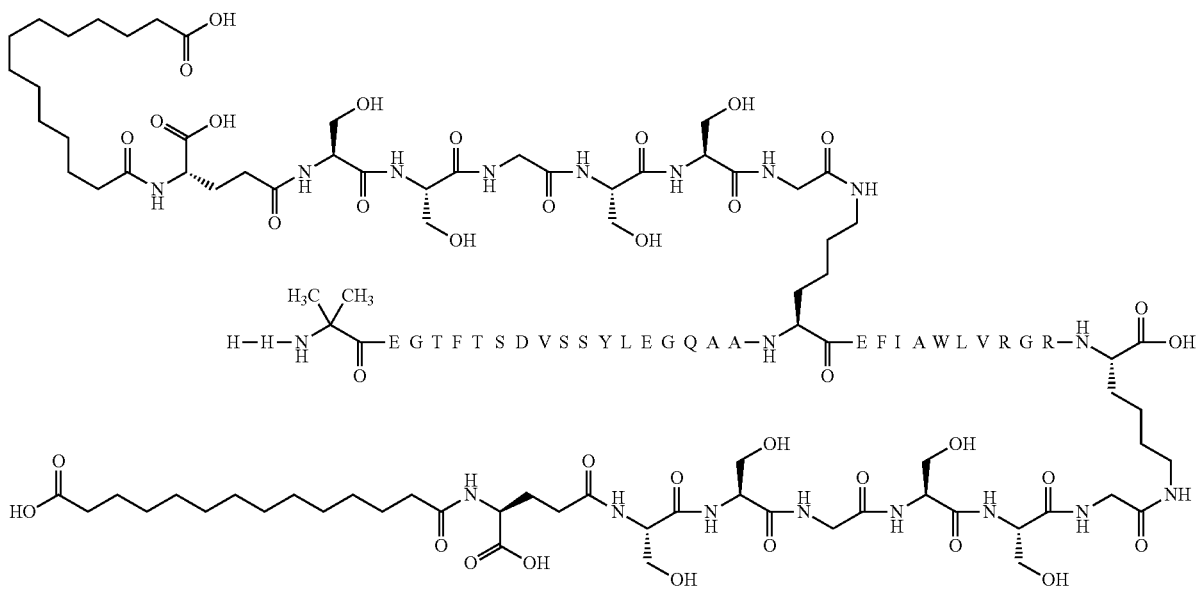

Preparation method: SPPS_A, SC_A, CP_M1
UPLC Method: B4_1: Rt=8.51 min,
UPLC Method: A6_1: Rt=6.36 min,
LCMS Method: LCMS_4: Rt=2.27 min; m/3:1703; m/4: 1277; m/5:1030

Example 11

N^α (N^{ε26}-[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib^8,His^{31},Gln^{34}]-GLP-1-(7-37)-peptidyl)-N^ε[2-[[(2S)-2-[[(2S)-2-[[2-[[(2S)-2-[[(2S)-2-[[(4S)-4-carboxy-4-[10-(4-carboxyphenoxy)decanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]Lys Chem. 30:

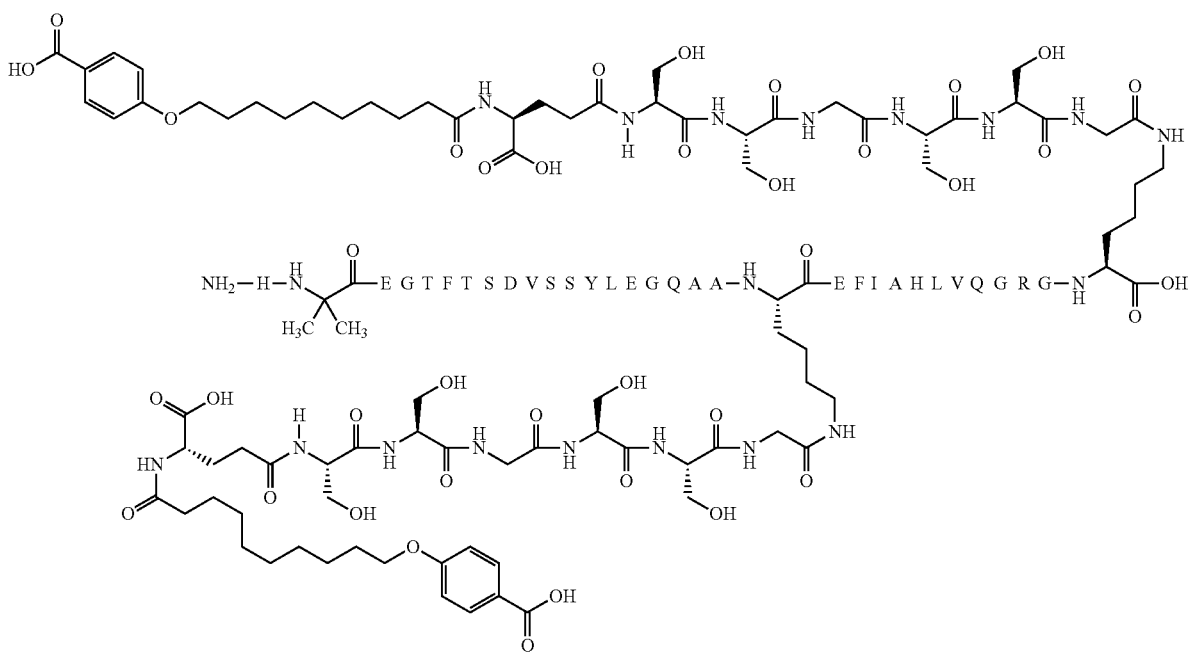

Preparation method: SPPS_A, SC_A, CP_M1
UPLC Method: B2_1: Rt=11.72 min
UPLC Method: A3_1: Rt=6.46 min
LCMS Method: LCMS_4: Rt=2.20 min; m/3:1738; m/4:1304; m/5:1043

Example 12

$N^{\epsilon 26}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\epsilon 37}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,His$^{34}$,Lys$^{37}$]-GLP-1-(7-37)-peptide Chem. 31:

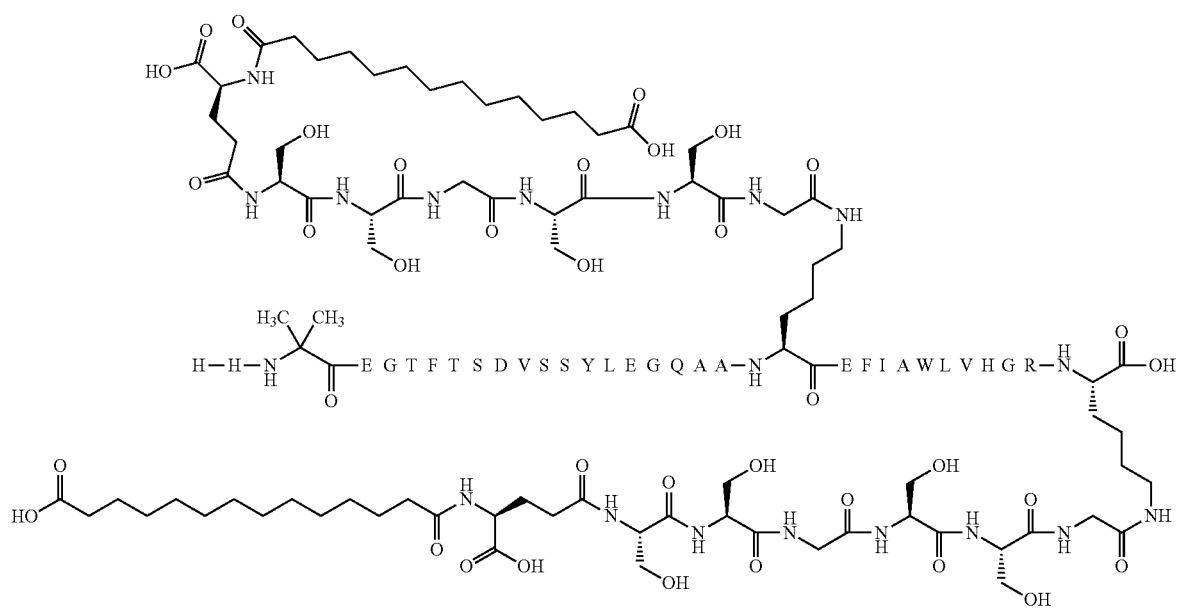

Preparation method: SPPS_A, SC_A, CP_M1
UPLC Method: B4_1: Rt=8.33 min
LCMS Method: LCMS_4: Rt=2.13 min; m/3:1705; m/4: 1279; m/5:1023

Example 13

N^ε18-[2-[[(2S)-2-[[(2S)-2-[[2-[[(2S)-2-[[(2S)-2-[[(4S)-4-carboxy-4-[12-(4-carboxyphenoxy)dode-canoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], N^ε26-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib^8,Lys^18,Gln^34]-GLP-1-(7-37)-peptide Chem. 32:

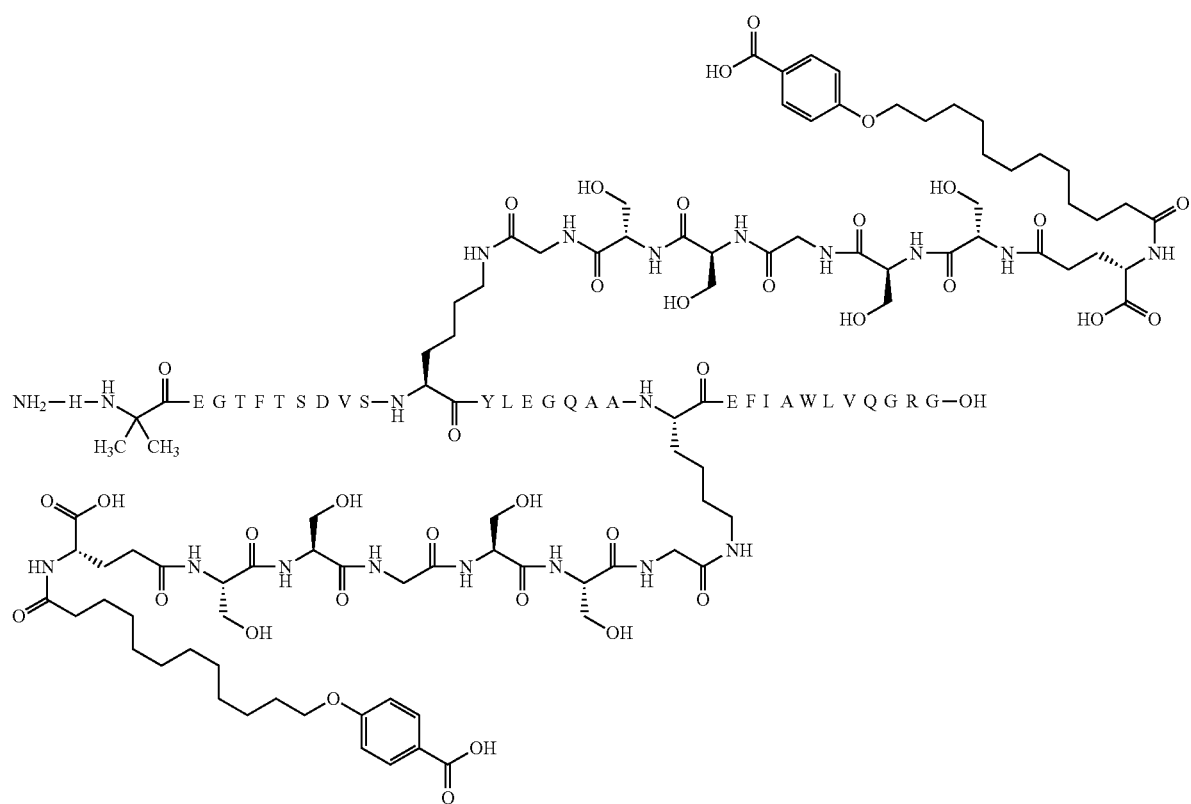

Preparation method: SPPS_P; SC_P; CP_M1
UPLC Method: AP_B4_1: Rt=9.17 min
LCMS Method: LCMS_AP: m/3=1745

Example 14

$N^{\epsilon 18}$-[2-[[(2S)-2-[[(2S)-2-[[2-[[(2S)-2-[[(2S)-2-[[(4S)-4-carboxy-4-[11-(4-carboxyphenoxy)unde-canoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\epsilon 26}$-[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Gln$^{34}$]-GLP-1-(7-37)-peptide Chem. 33:

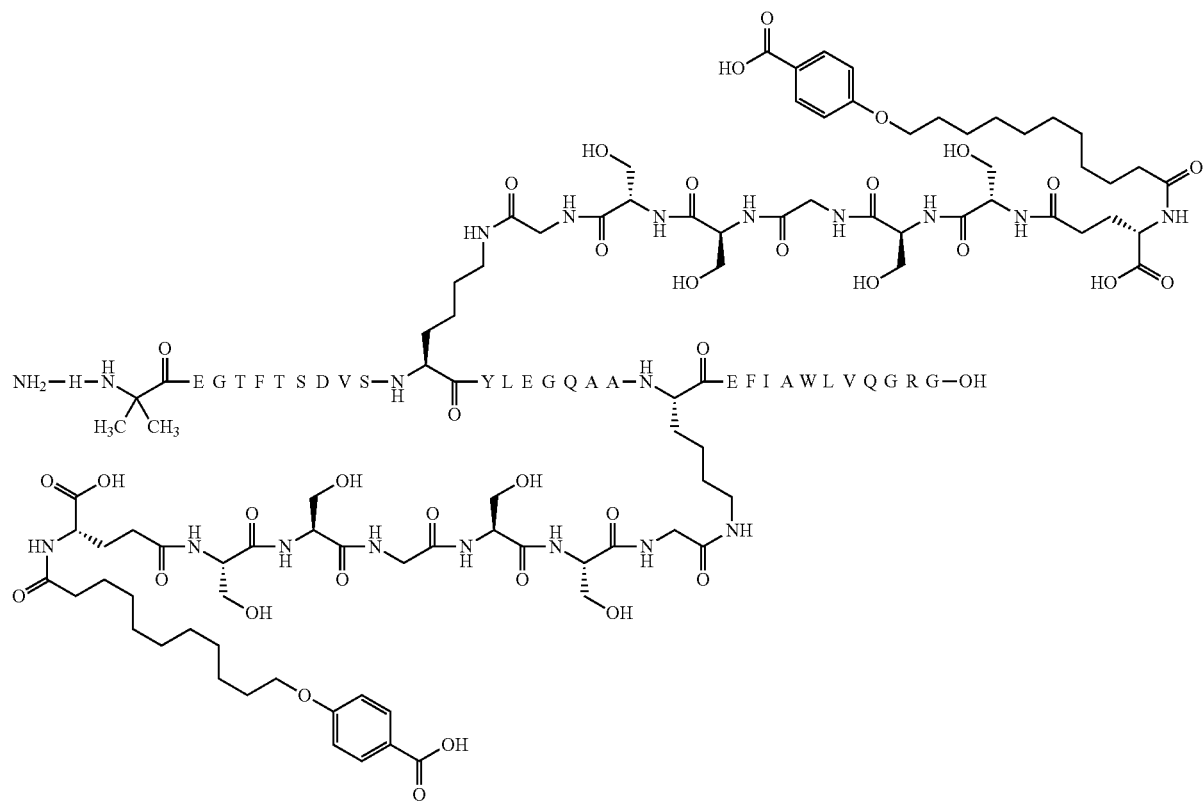

Preparation method: SPPS_P, SC_P, CP_M1
UPLC Method: B4_1: Rt=8.65 min
LCMS Method: LCMS_4: Rt=2.33 min; m/3:1735; m/4: 1302

Example 15

$N^{\varepsilon 18}$-[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]propanoyl]amino]-3-hydroxypropanoyl]amino]-3-hydroxypropanoyl]amino]propanoyl], $N^{\varepsilon 26}$-[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]propanoyl]amino]-3-hydroxypropanoyl]amino]-3-hydroxypropanoyl]amino]propanoyl]-[Aib$^8$,Lys$^{18}$,Gln$^{34}$]-GLP-1-(7-37)-peptide Chem. 34:

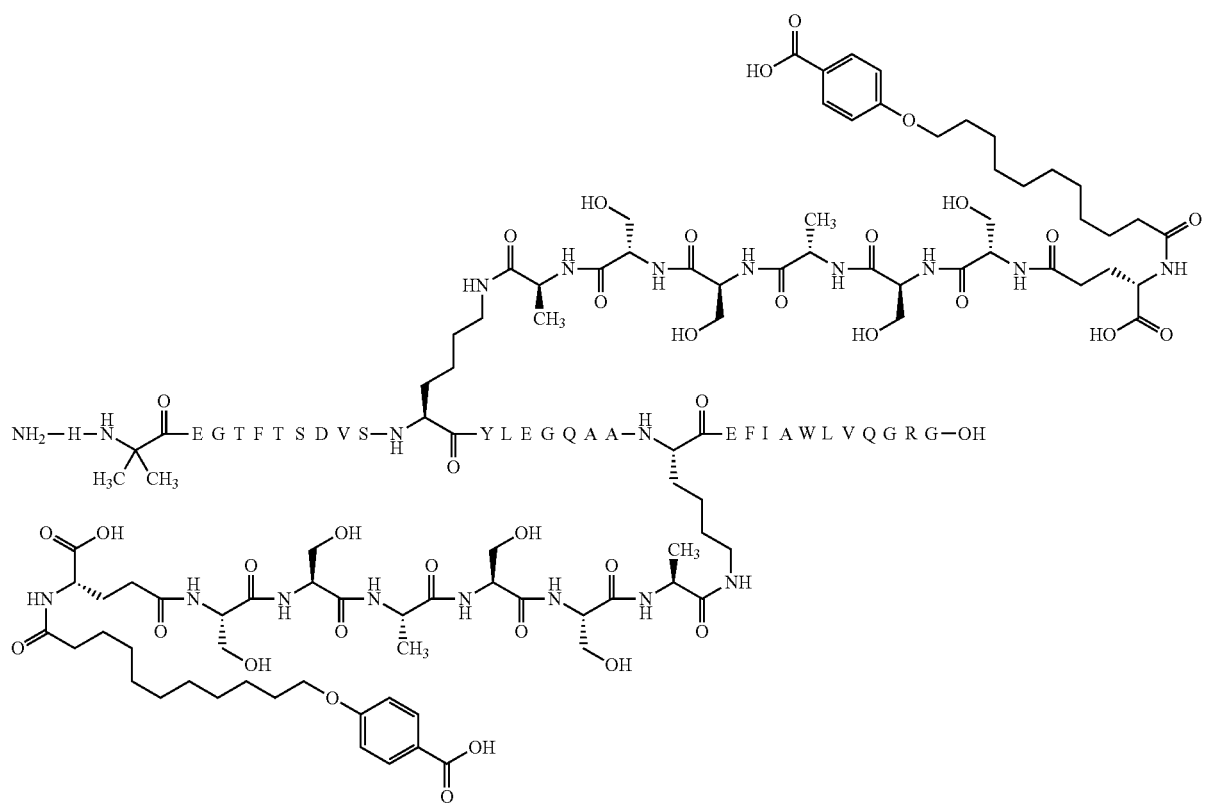

Preparation method: SPPS_P, SC_P, CP_M1
UPLC Method: B4_1: Rt=8.70 min
LCMS Method: LCMS_4: Rt=2.33 min; m/3:1753; m/4: 1315

Example 16

$N^{\varepsilon 18}$-[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]-3-hydroxypropanoyl], $N^{\varepsilon 26}$-[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]-[Aib$^8$,Lys$^{18}$,Gln$^{34}$]-GLP-1-(7-37)-peptide Chem. 35:

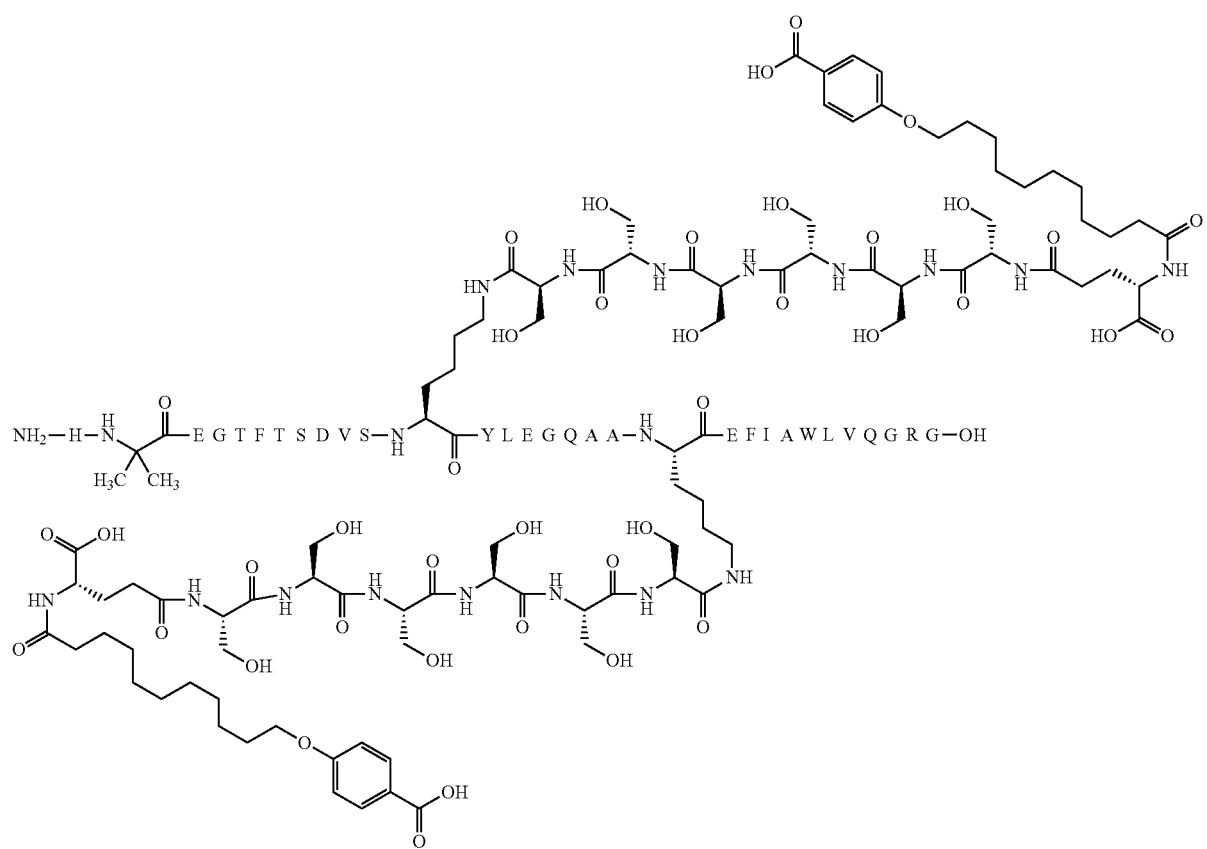

Preparation method: SPPS_P, SC_P, CP_M1
UPLC Method: B4_1: Rt=8.61 min
LCMS Method: LCMS_4: Rt=2.33 min; m/3:1775; m/4: 1331

Example 17

$N^{\epsilon 18}$-[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\epsilon 26}$-[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib8,Lys18,Gln34]-GLP-1-(7-37)-peptide Chem. 36:

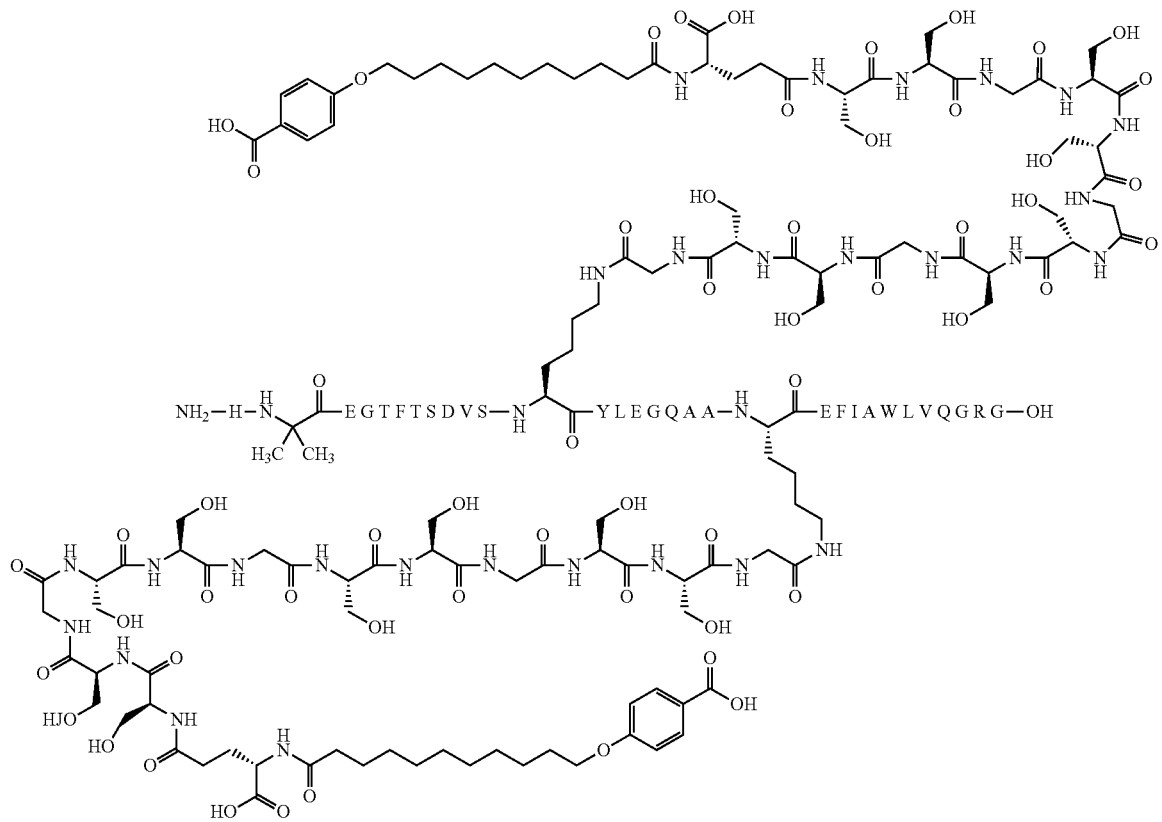

Preparation method: SPPS_P, SC_P, CP_M1
UPLC Method: B4_1: Rt=8.28 min
LCMS Method: LCMS_4: Rt=2.50 min; m/4:1533; m/5: 1226

Example 18

$N^{\varepsilon 18}$-[(2S)-2-amino-6-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl], $N^{\varepsilon 26}$-[(2S)-2-amino-6-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl]-[Aib$^8$,Lys$^{18}$,Gln$^{34}$]-GLP-1-(7-37)-peptide Chem. 37:

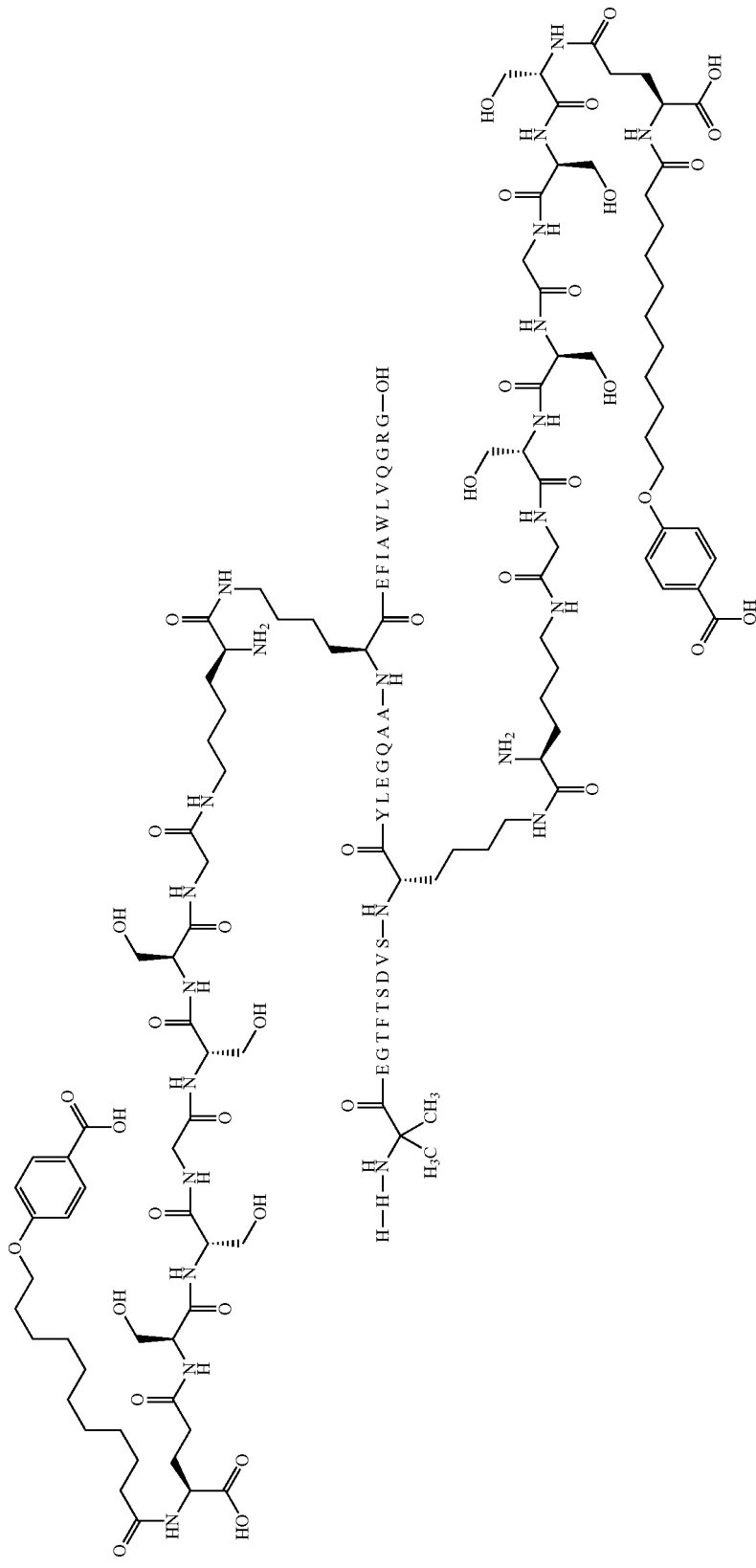

Preparation method: SPPS_P, SC_P, CP_M1
UPLC Method: B4_1: Rt=8.11 min
LCMS Method: LCMS_AP: Rt=4.79 min; m/3:1820; m/4: 1365

Example 19

$N^{\epsilon 18}$-[(2S)-2-amino-6-[[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]hexanoyl], $N^{\epsilon 26}$-[(2S)-2-amino-6-[[(2S)-2-[[(2S)-2-[[(2S)-2-[[(2S)-2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]hexanoyl]-[Aib$^8$,Lys$^{18}$,Gln$^{34}$]-GLP-1-(7-37)-peptide Chem. 38:

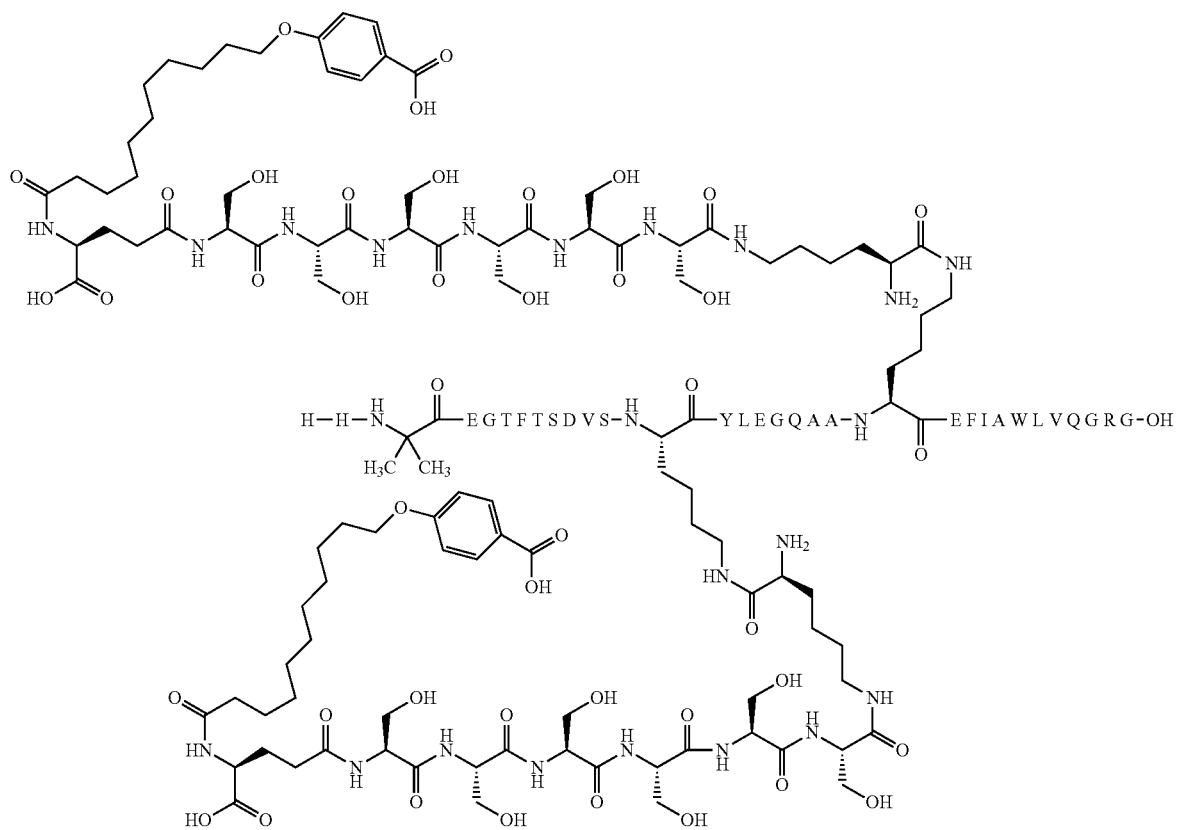

Preparation method: SPPS_P, SC_P, CP_M1
UPLC Method: B4_1: Rt=8.61 min
LCMS Method: LCMS_4: Rt=2.20 min; m/3:1860; m/4: 1395; m/5:1117

Example 20

N^ε18-[(2S)-2-amino-6-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl],
N^ε26-[(2S)-2-amino-6-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl]-[Aib8,Lys18,Gln34]-GLP-1-(7-37)-peptide Chem. 39:

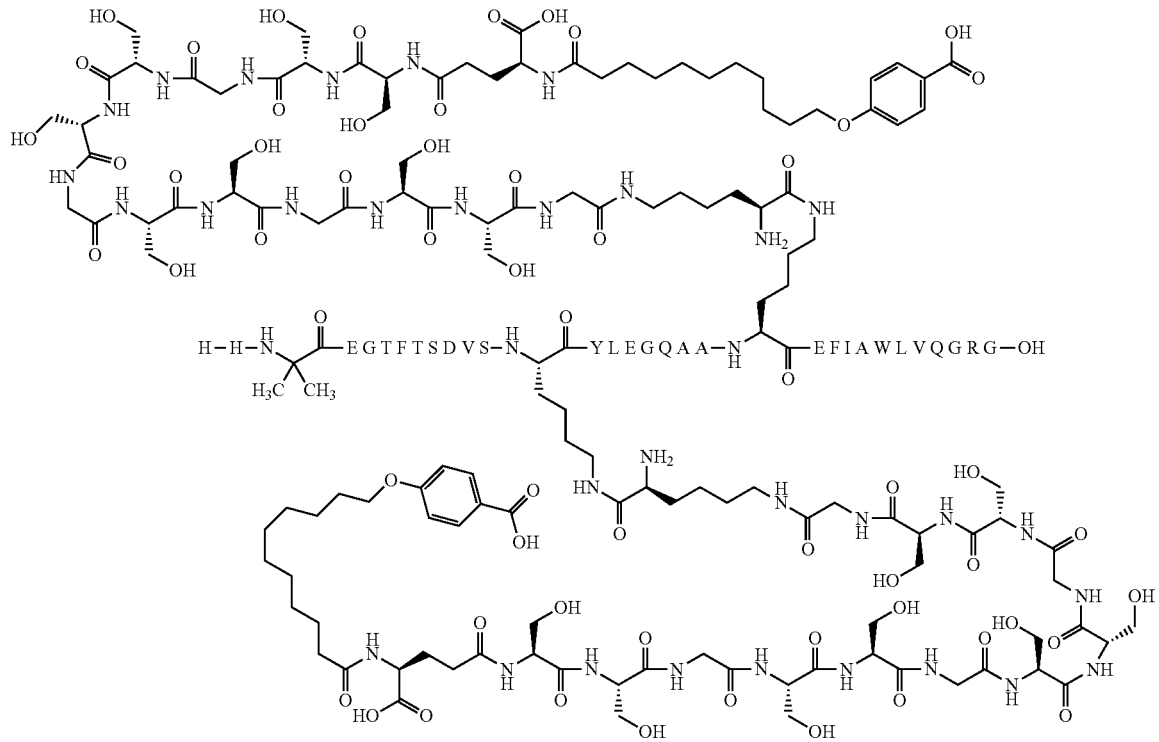

Preparation method: SPPS_P, SC_P, CP_M1
UPLC Method: B4_1: Rt=7.85 min
LCMS Method: LCMS_4: Rt=2.58 min; m/4:1597; m/5: 1277

Example 21

N$^{\epsilon 18}$-[(2S)-2-amino-6-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl], N$^{\epsilon 26}$-[(2S)-2-amino-6-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl]-[Aib$^8$,Lys$^{18}$,Gln$^{34}$]-GLP-1-(7-37)-peptide Chem. 40:

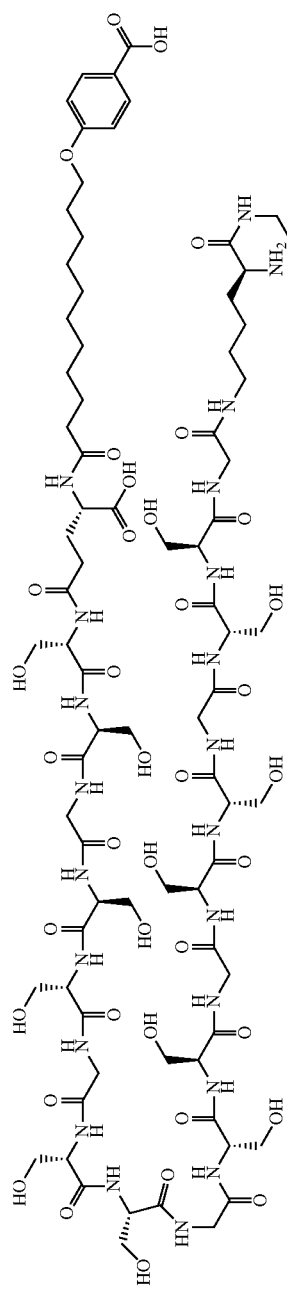
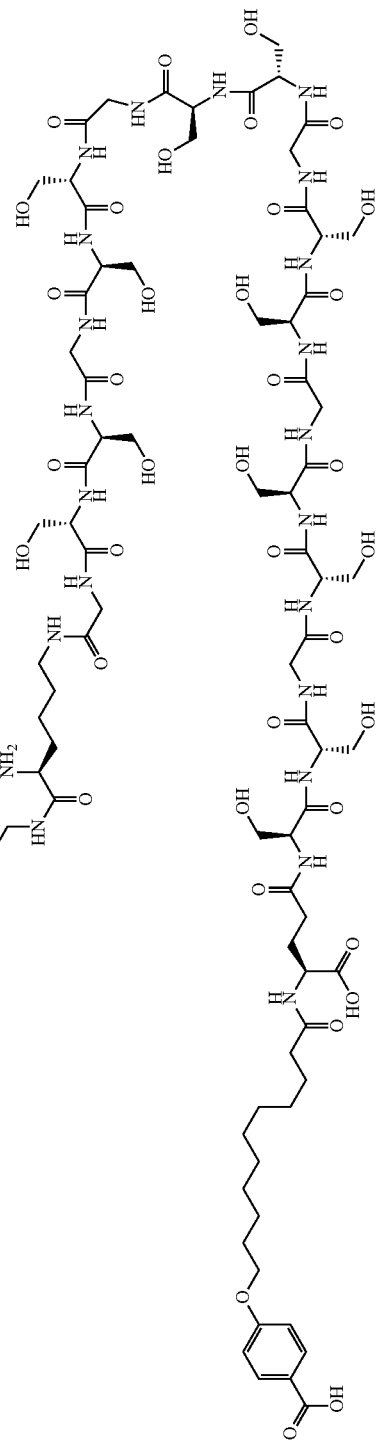

Preparation method: SPPS_P, SC_P, CP_M1
UPLC Method: B29_1: Rt=8.42 min
LCMS Method: LCMS_4: Rt=2.52 min; m/4:1828; m/5: 1463

Example 22

$N^{\epsilon 18}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\epsilon 26}$-[2-[[(2S)-2-[[(2S)-2-[[2-[[(2S)-2-[[(2S)-2-[[(4S)-4-carboxy-4-(13-carboxytridecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Lys$^{18}$,Gln$^{34}$]-GLP-1-(7-37)-peptide Chem. 41:

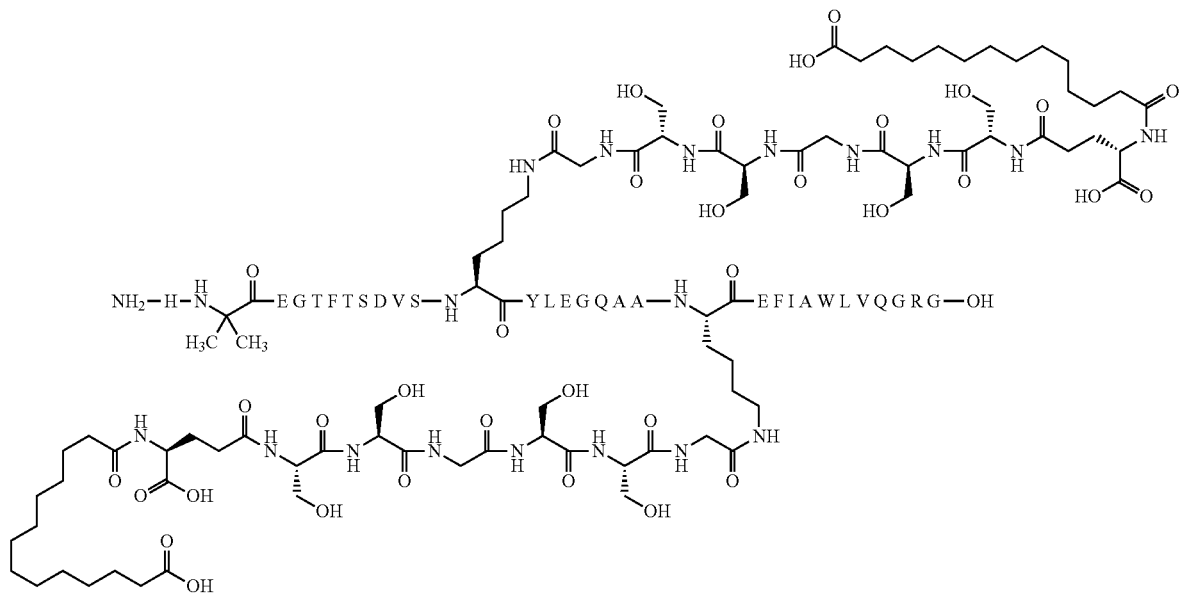

Preparation method: SPPS_P, SC_P, CP_M1
UPLC Method: B2_1: Rt=8.27 min
UPLC Method: A6_1: Rt=4.85 min
LCMS Method: LCMS_4: Rt=2.4 min; m/4:1269

Example 23

$N^{\varepsilon 26}$-[2-[[(2S)-2-[[(2S)-2-[[2-[[(2S)-2-[[(2S)-2-[[(4S)-4-carboxy-4-(15-carboxypentadecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\varepsilon 37}$-[2-[[(2S)-2-[[(2S)-2-[[2-[[(2S)-2-[[(2S)-2-[[(4S)-4-carboxy-4-(15-carboxypentadecanoylamino)butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Arg$^{34}$,Lys$^{37}$]-GLP-1-(7-37)-peptide Chem. 42:

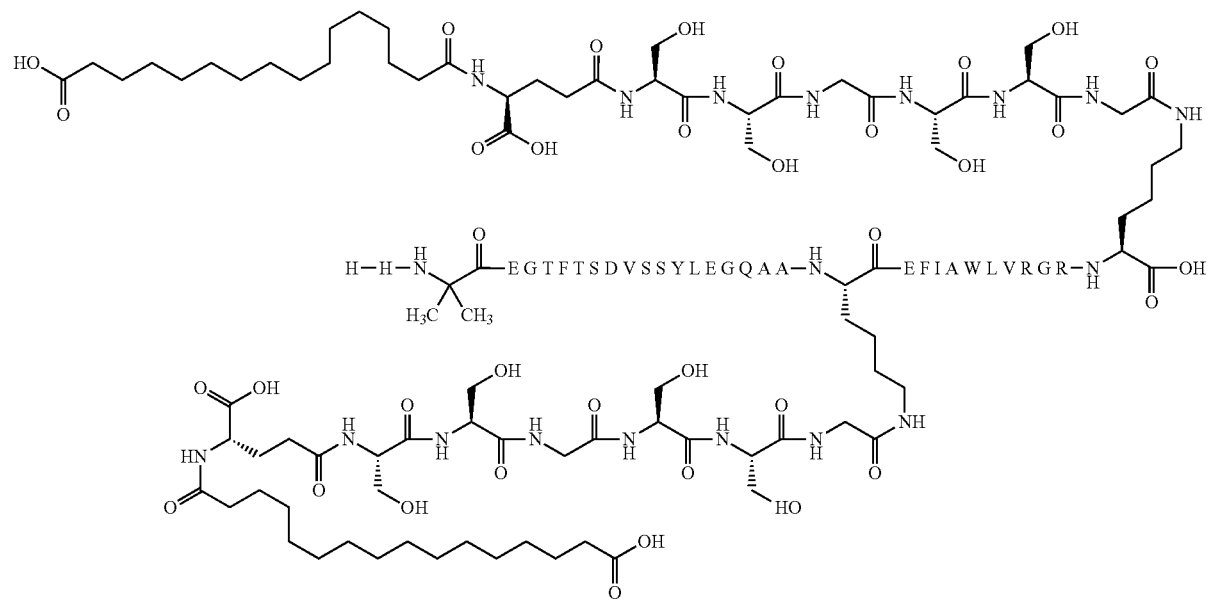

Preparation method: SPPS_P, SC_A, CP_M1
UPLC Method: B4_1: Rt=8.76 min
LCMS Method: LCMS_4: Rt=2.27 min; m/3:1731; m/4: 1298; m/5:1039

Example 24

$N^{\varepsilon 26}$-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], $N^{\varepsilon 37}$-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib$^8$,Arg$^{34}$,Lys$^{37}$]-GLP-1-(7-37)-peptide Chem. 43:

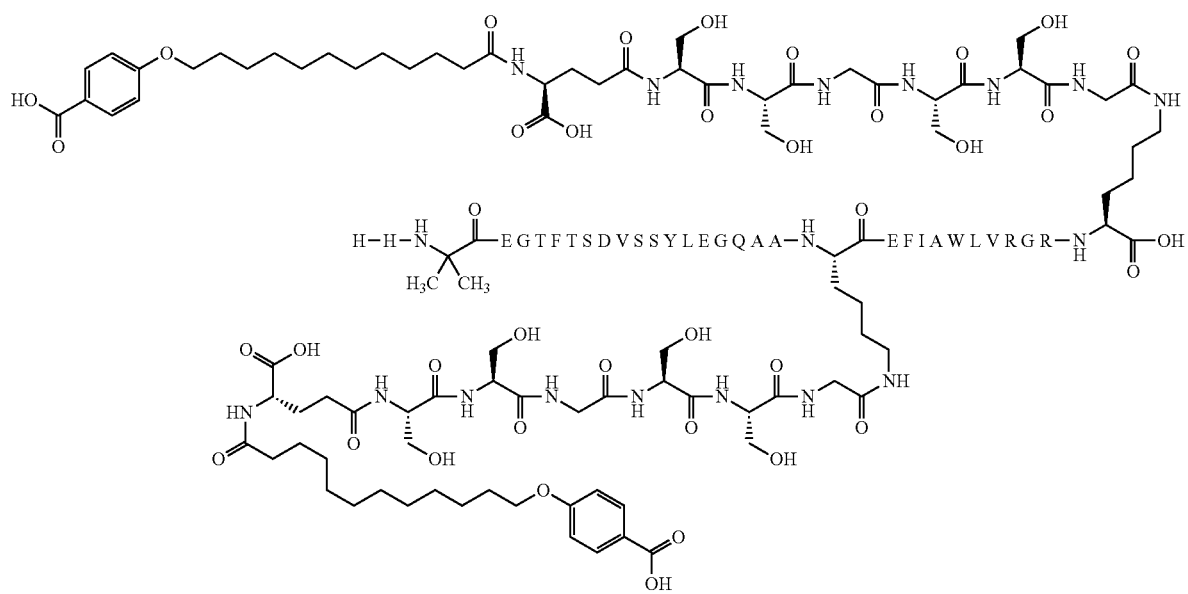

Preparation method: SPPS_P, SC_A, CP_M1
UPLC Method: B4_1: Rt=8.67 min
LCMS Method: LCMS_4: Rt=2.40 min; m/3:1763; m/4: 1322

Example 25

N$^{\epsilon26}$-[(2S)-2-amino-6-[[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl], N$^{\epsilon37}$-[(2S)-2-amino-6-[[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]amino]hexanoyl]-[Aib$^8$,Arg$^{34}$,Lys$^{37}$]-GLP-1-(7-37)-peptide Chem. 44:

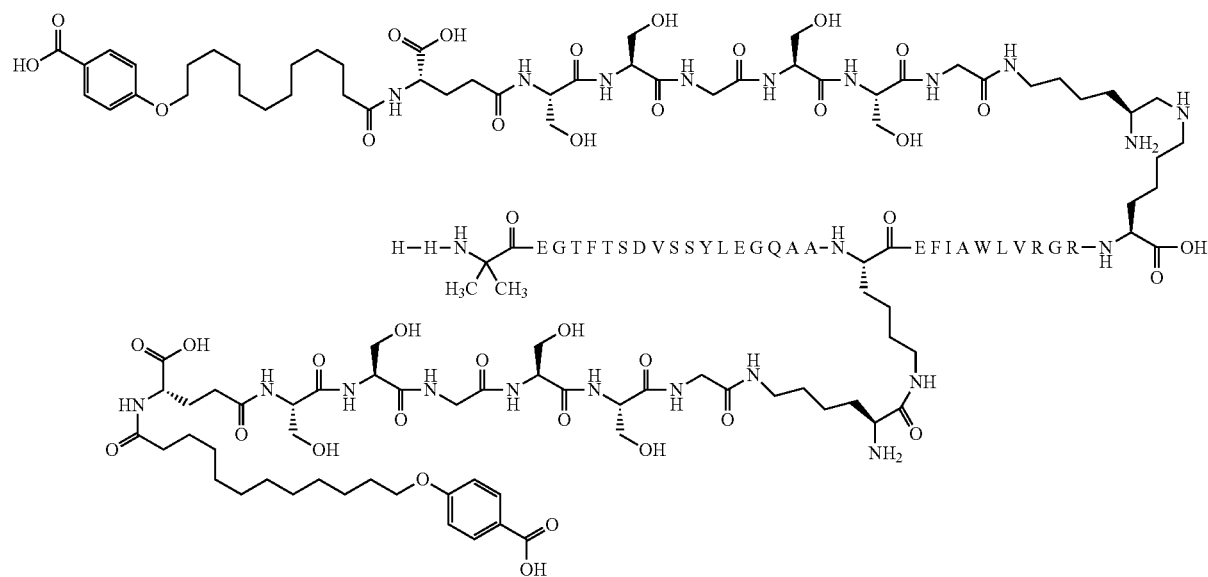

Preparation method: SPPS_L, SC_A, CP_M1
UPLC Method: B4_1: Rt=8.70 min
LCMS Method: LCMS_4: Rt=2.10 min; m/3:1849; m/4: 1387; m/5:1110

Example 26

N^ε26-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], N^ε37-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Imp^7,Aib^8,Arg^34,Lys^37]-GLP-1-(7-37)-peptide Chem. 45:

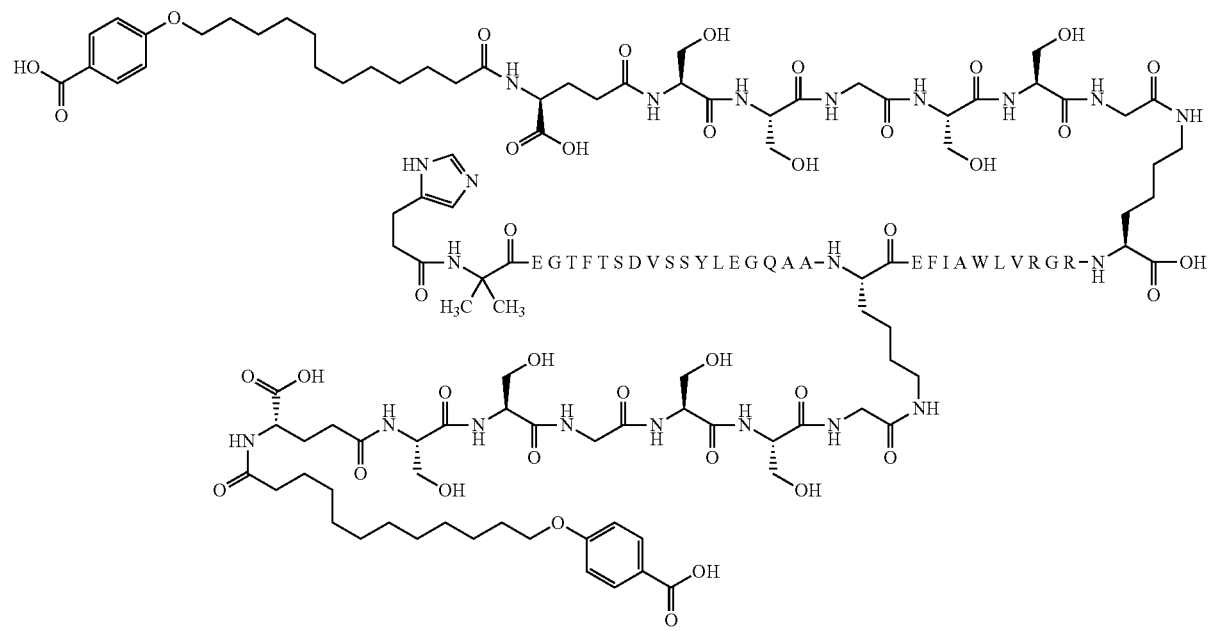

Preparation method: SPPS_P; SC_P; CP_M1
UPLC method: B4_1: Rt=8.9 min
LCMS method: LCMS_4: Rt=2.35 min; m/3=1758; m/4=1319; m/5=1055

Example 27

N$^{\varepsilon 26}$-[2-[[(2S)-2-[[(2S)-2-[[2-[[(2S)-2-[[(2S)-2-[[(4S)-4-carboxy-4-[11-(4-carboxyphenoxy)unde-canoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], N$^{\varepsilon 37}$-[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Imp$^7$,Aib$^8$,Arg$^{34}$,Lys$^{37}$]-GLP-1-(7-37)-peptide Chem. 46:

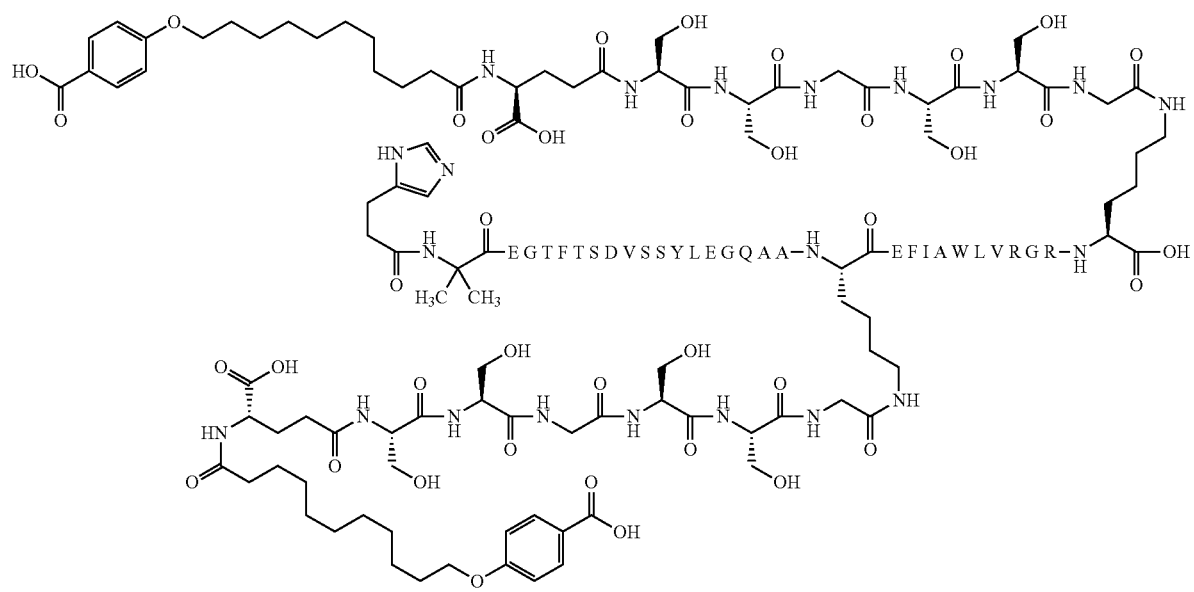

Preparation method: SPPS_P; SC_P; CP_M1
UPLC Method: AP_B4_1: Rt=8.5 min
LCMS Method: LCMS_4: Rt=2.28 min, m/3=1749; m/4=1312

Example 28

N$^{\epsilon 18}$-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], N$^{\epsilon 26}$-[2-[[(2S)-2-[[(2S)-2-[[2-[[(2S)-2-[[(2S)-2-[[(4S)-4-carboxy-4-[12-(4-carboxyphenoxy)dodecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Imp$^7$,Aib$^8$,Lys$^{18}$,Gln$^{34}$]-GLP-1-(7-37)-peptide Chem. 47:

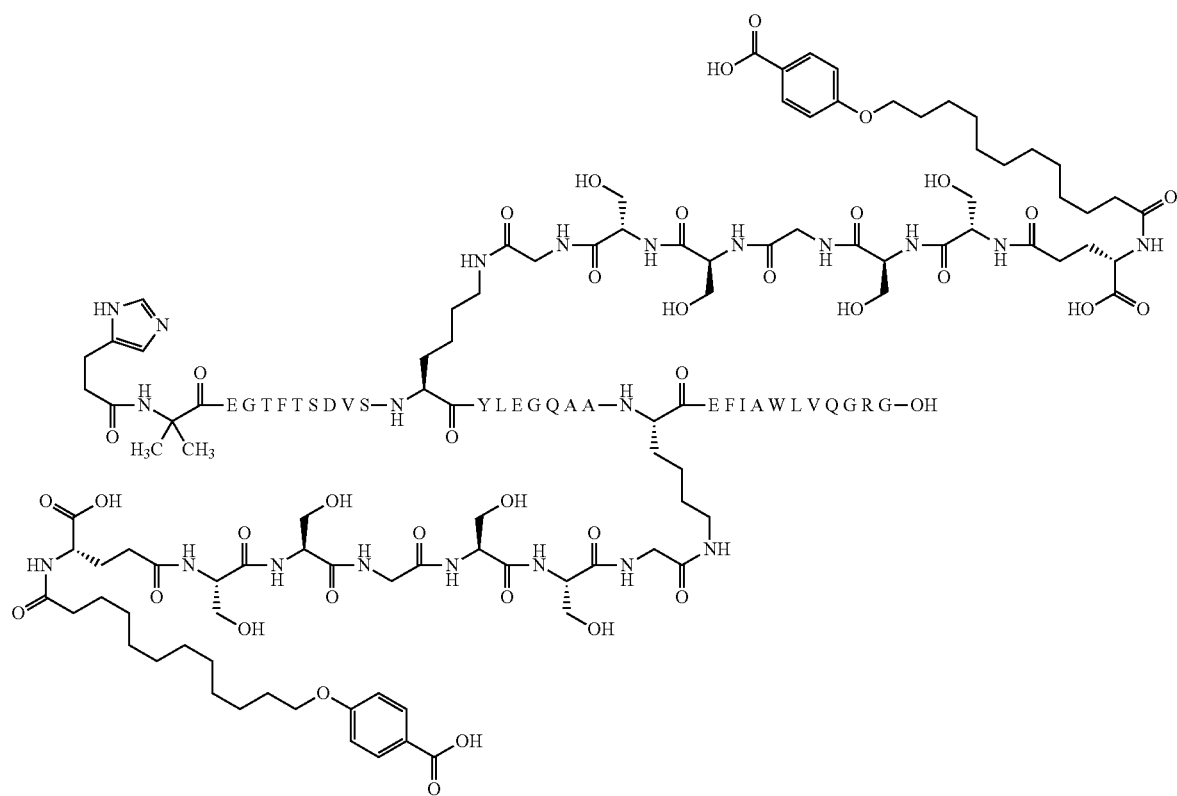

Preparation method: SPPS_P; SC_P; CP_M1
UPLC Method: AP_B4_1: Rt=9.3 min
LCMS Method: LCMS_4: Rt=2.45 min, m/3=1739; m/4=1305

Example 29

$N^{\epsilon 26}$-[(2S)-2-amino-6-[[(2S)-2-[[2-[[(2S)-2-[[(4S)-4-carboxy-4-[12-(4-carboxyphenoxy)dodecanoylamino]butanoyl]amino]-3-hydroxypropanoyl]amino]acetyl]amino]-3-hydroxypropanoyl]amino]hexanoyl], $N^{\epsilon 37}$-[(2S)-2-amino-6-[[(2S)-2-[[2-[[(2S)-2-[[(4S)-4-carboxy-4-[12-(4-carboxyphenoxy)dodecanoylamino]butanoyl]amino]-3-hydroxypropanoyl]amino]acetyl]amino]-3-hydroxypropanoyl]amino]hexanoyl]-[Aib$^8$,Arg$^{34}$,Lys$^{37}$]-GLP-1-(7-37)-peptide Chem. 48:

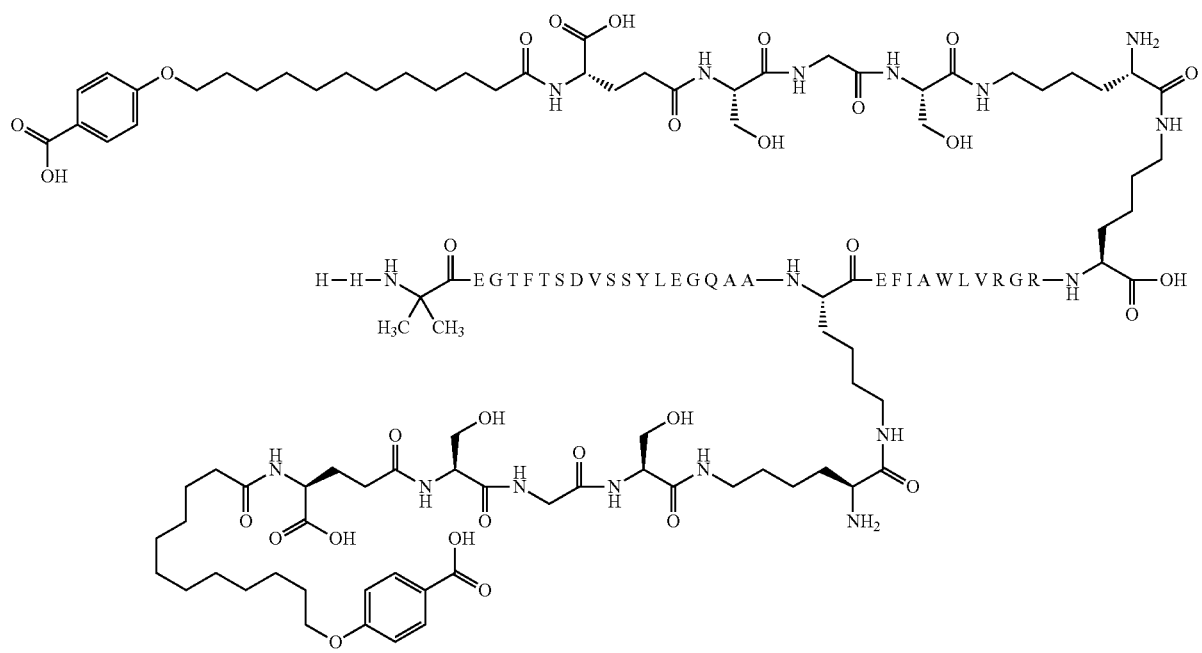

Preparation method: SPPS_P; SC_P; CP_M1
UPLC Method: AP_B4_1: Rt=8.4 min
LCMS Method: LCMS_4: Rt=2.15 min, m/3=1695; m/4=1271

Example 30

$N^{\epsilon 26}$-[(2S)-2-amino-6-[[(2S)-2-[[2-[[(2S)-2-[[(4S)-4-carboxy-4-[12-(4-carboxyphenoxy)dodecanoylamino]butanoyl]amino]-3-hydroxypropanoyl]amino]acetyl]amino]-3-hydroxypropanoyl]amino]hexanoyl], $N^{\epsilon 37}$-[(2S)-2-amino-6-[[(2S)-2-[[2-[[(2S)-2-[[(4S)-4-carboxy-4-[12-(4-carboxyphenoxy)dodecanoylamino]butanoyl]amino]-3-hydroxypropanoyl]amino]acetyl]amino]-3-hydroxypropanoyl]amino]hexanoyl]-[Imp$^7$,Aib$^8$,Arg$^{34}$,Lys$^{37}$]-GLP-1-(7-37)-peptide Chem. 49:

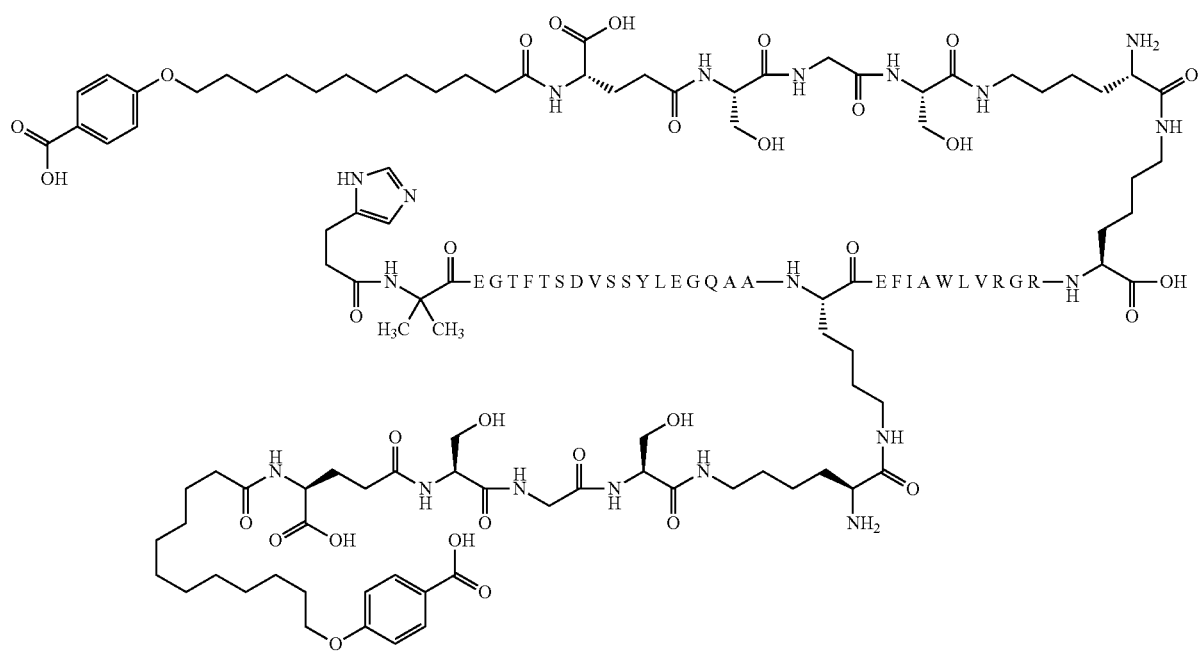

Preparation method: SPPS_P; SC_P; CP_M1
UPLC Method: AP_B4_1: Rt=8.5 min
LCMS Method: LCMS_4: Rt=2.2 min, m/3=1690; m/4=1268

Example 31

N^ε26-[2-[[(2S)-2-[[(2S)-2-[[2-[[(2S)-2-[[(2S)-2-[[(4S)-4-carboxy-4-[11-(4-carboxyphenoxy)unde-canoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl], N^ε37-[2-[[(2S)-2-[[(2S)-2-[[2-[[(2S)-2-[[(2S)-2-[[(4S)-4-carboxy-4-[11-(4-carboxyphenoxy)undecanoylamino]butanoyl]amino]-3-hydroxypropanoyl]amino]-3-hydroxypropanoyl]amino]acetyl]amino]-3-hydroxypropanoyl]amino]-3-hydroxypropanoyl]amino]acetyl]-[Aib^8,Arg^34,Lys^37]-GLP-1-(7-37)-peptide Chem. 50:

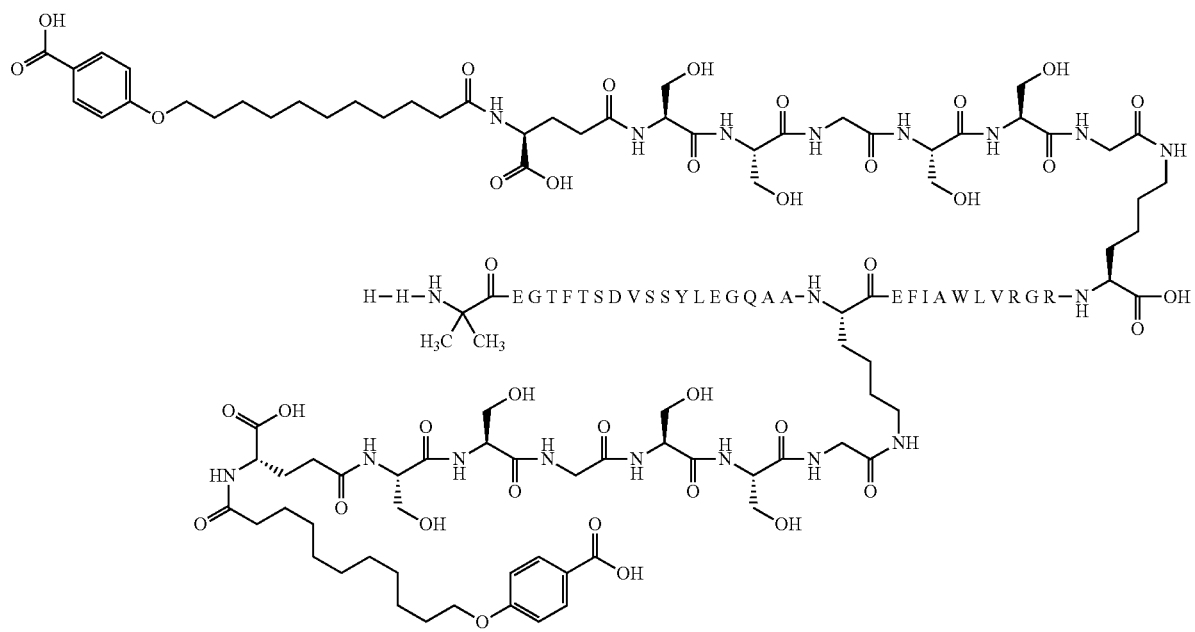

Preparation method: SPPS_CS; SPPS_L; SC_CS; CP_M1
UPLC Method: B4_1: Rt=8.47 min
LCMS Method: LCMS_4: Rt=2.20 min; m/3:1754; m/4:1316; m/5:1053

Comparative Compounds

A number of comparative compounds are referred to in this application.

Liraglutide, a mono-acylated GLP-1 derivative for once daily administration which is marketed by Novo Nordisk A/S (tradename VICTOZA®), is disclosed in WO 98/08871 A1 (Example 37).

Semaglutide, a mono-acylated GLP-1 derivative for once weekly administration which is under development by Novo Nordisk A/S, is disclosed in WO 06/097537 A2 (Example 4).

The comparative compounds referred to below are disclosed in WO 2011/080103, WO 2011/080102, or WO 2012/062803. They are direct comparative compounds in the sense that they differ from the compounds of the invention only in the linker. The linker of the comparative compounds may be referred to as the "gGlu-2×OEG" linker. This linker has been used very frequently in the past and has proven to be a very good linker. The gGlu-2×OEG linker is described in several prior publications, e.g. in WO 2011/080103, see Chem. 5, 5a (OEG) and 6 (gGlu).

As regards the nomenclature used herein, we have added an "a" to the number of the comparative examples. For example, the direct comparator to the compound of Example 1 is the compound of Example 1a; the direct comparator to the compound of Example 2 is the compound of Example 2a, and so forth (emphasis added). Ten of the example compounds herein have a direct comparator as described above which is known in the art. This is not the case for the remaining example compounds. Accordingly, for the remaining compounds there are no known corresponding direct comparator compounds.

Example 1a

Compound of Example 2, Chem. 21, in WO 2011/080103.

Example 2a

Compound of Example 17, Chem. 36, in WO 2011/080103.

Example 3a

Compound of Example 33, Chem. 52, in WO 2011/080103.

Example 4a

Compound of Example 46, Chem. 65, in WO 2011/080103.

Example 5a

Compound of Example 38, Chem. 57, in WO 2012/062803.

Example 6a

Compound of Example 74, Chem. 93, in WO 2012/062803.

Example 7a

Compound of Example 2, Chem. 21, in WO 2012/062803.

Example 9a

Compound of Example 92, Chem. 111, in WO 2012/062803.

Example 22a

Compound of Example 141, Chem. 189, in WO 2012/062803.

Example 23a

Compound of Example 3, Chem. 22, in WO 2011/080103.

Pharmacological Methods

Example 32

In vitro Potency (AlphaScreen; Membranes)

The purpose of this example is to test the activity, or potency, of the GLP-1 derivatives in vitro.

The potencies of the GLP-1 derivatives of Examples 1-31 and comparative Examples 1a-7a, 9a, 22a, and 23a were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 analogue or derivative in question, and the potency of cAMP production was measured using the AlphaScreen™ cAMP assay kit from Perkin Elmer Life Sciences. The basic principle of the AlphaScreen assay is a competition between endogenous cAMP and exogenously added biotin-cAMP. The capture of cAMP is achieved by using a specific antibody conjugated to acceptor beads.

Cell Culture and Preparation of Membranes

A stably transfected cell line and a high expressing clone were selected for screening. The cells were grown at 5% $CO_2$ in DMEM, 5% FCS, 1% Pen/Strep (Penicillin/Streptomycin) and 0.5 mg/ml of the selection marker G418.

Cells at approximate 80% confluence were washed twice with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 s in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 s and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in flat-bottom 96-well plates (Costar cat. no:3693). The final volume per well was 50 µl.

Solutions and Reagents

AlphaScreen cAMP assay kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM Tris-HCl (Sigma, cat.no: T3253); 5 mM HEPES (Sigma, cat.no: H3375); 10 mM $MgCl_2$, $6H_2O$ (Merck, cat.no: 5833); 150 mM NaCl (Sigma, cat.no: S9625); 0.01% Tween (Merck, cat.no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 µM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 analogue or derivative to be tested, e.g. the following eight concentrations of the GLP-1 compound: $10^{-7}$, $10^{-8}$, $10^{-9}$, $10^{-10}$, $10^{-11}$, $10^{12}$, $10^{-13}$ and $10^{-14}$M, and a series from, e.g., $10^{-6}$ to $3\times10^{-11}$ of cAMP.

Membrane/Acceptor Beads

Membranes were prepared from hGLP-1/BHK 467-12A cells with a concentration of 6 µg/well, corresponding to 0.6 mg/ml (the amount of membranes used pr. well may vary)

"No membranes": Acceptor Beads (15 µg/ml final) in AlphaScreen buffer

"6 µg/well membranes": membranes+Acceptor Beads (15 µg/ml final) in AlphaScreen buffer An aliquot (10 µl) of "No membranes" was added to the cAMP standard (per well in duplicates) and the positive and negative controls An aliquot (10 µl) of "6 µg/well membranes" to GLP-1 and analogues (per well in duplicate or triplicate wells)

Pos. Control: 10 µl "No membranes"+10 µl AlphaScreen Buffer

Neg. Control: 10 µl "No membranes"+10 µl cAMP Stock Solution (50 µM)

As the beads are sensitive to direct light, all handling was performed in the dark (as dark as possible), or in green light. All dilutions were made on ice.

Procedure

1. Make the AlphaScreen Buffer.
2. Dissolve and dilute the GLP-1/Analogues/cAMP standard in AlphaScreen Buffer.
3. Make the Donor Beads solution by mixing streptavidin donor beads (2 units/well) and biotinylated cAMP (1.2 units/well) and incubate 20-30 min in the dark at room temperature.
4. Add the cAMP/GLP-1/Analogues to the plate: 10 µl per well.
5. Prepare membrane/Acceptor Beads solution and add this to the plates: 10 µl per well.
6. Add the Donor Beads: 30 µl per well.
7. Wrap the plate in aluminum foil and incubate on the shaker for 3 hours (very slowly) at room temperature.
8. Count on AlphaScreen—each plate pre incubates in the AlphaScreen for 3 minutes before counting.

Results

The $EC_{50}$ [pM] values were calculated using the Graph-Pad Prism software (version 5) and are shown in Table 1 below. The $EC_{50}$ [pM] value for each compound of the invention may be related to the respective comparative compound by calculating N: N=100×($EC_{50}$ (comparative compound)/$EC_{50}$ (compound of the invention)). The figure N thus shows the percentage of improvement of the in vitro potency of the compounds of the invention, relative to the respective comparative compound.

TABLE 1

| Example no. | In vitro potency (AlphaScreen cAMP; membranes) $EC_{50}$ [pM] |
|---|---|
| 1 | 32 |
| 1a | 112 |
| 2 | 116 |
| 2a | 582 |
| 3 | 137 |
| 3a | 506 |
| 4 | 48 |
| 4a | 101 |
| 5 | 95 |
| 5a | 224 |
| 6 | 34 |
| 6a | 62 |
| 7 | 110 |
| 7a | 395 |
| 8 | 230 |
| 9 | 276 |
| 9a | 1589 |
| 10 | 31 |
| 11 | 381 |
| 12 | 145 |
| 13 | 314 |
| 14 | 261 |
| 15 | 183 |
| 16 | 146 |
| 17 | 171 |
| 18 | 89 |
| 19 | 181 |
| 20 | 350 |
| 21 | 486 |
| 22 | 307 |
| 22a | 1139 |
| 23 | 2500 |
| 23a | 1683 |
| 24 | 166 |
| 25 | 252 |
| 26 | 446 |
| 27 | 138 |
| 28 | 460 |
| 29 | 238 |
| 30 | 276 |
| 31 | 27 |

The potency of all tested derivatives was confirmed in vitro.

With a lone exception (compound of Example 23) the derivatives had a surprisingly good in vitro potency corresponding to an $EC_{50}$ of 500 pM or below. Seventeen derivatives were even more potent having an $EC_{50}$ at 200 pM or below; and seven derivatives had a very good potency corresponding to an $EC_{50}$ at 100 pM or below.

With the same lone exception the in vitro potency of the compounds of the invention was generally 2-5 times improved, as compared to the comparative compounds.

Example 33

In vitro Potency (CRE Luciferase; Whole Cells)

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-31 and comparative Examples 1a-7a, 9a, 22a, and 23a were determined as described below.

Principle

In vitro potency was determined by measuring the response of human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor was activated it results in the production of cAMP, which in turn results in the luciferase protein being expressed. When assay incubation was completed the luciferase substrate (luciferin) was added and the enzyme converts luciferin to oxyluciferin and produces bioluminescence. The luminescence was measured and was the readout for the assay.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in cell culture medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Cell culture medium consisted of 10% FBS (Fetal Bovine Serum), 1 mg/ml G418, 240 nM MTX (methotrexate) and 1% pen/strep (penicillin/streptomycin. Assay medium consisted of DMEM w/o phenol red, 10 mM Hepes and 1× Glutamax. The 1% assay buffer consisted of 2% ovalbumin, 0.2% Pluronic F-68 and 2% HSA in assay medium. The 0% assay buffer consisted of 2% ovalbumin and 0.2% Pluronic F-68 in assay medium.

Procedure

1) Cell stocks were thawed in a 37° C. water bath.
2) Cells were washed three times in PBS.
3) The cells were counted and adjusted to $5 \times 10^3$ cells/50 µl ($1 \times 10^5$ cells/ml) in assay medium. A 50 µl aliquot of cells was transferred to each well in the assay plate.
4) Stocks of the test compounds and reference compounds were diluted to a concentration of 0.2 µM in 0% assay buffer for the 0% HSA CRE luciferase assay and 1% assay buffer for the HSA CRE luciferase assay. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M and $2 \times 10^{-13}$ M. For each compound a blank assay buffer control was also included.
5) A 50 µl aliquot of compound or blank was transferred in triplicate from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M and $1 \times 10^{-13}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate (reagent was light sensitive).
9) Each assay plate was covered with aluminum foil to protect it from light and shaken for 30 min at room temperature.

10) Each assay plate was read in a Packard TopCount NXT instrument.

Calculations and Results

The data from the TopCount instrument were transferred to GraphPad Prism 5 software. The software averages the values for each triplicate and performs a non-linear regression (log(agonist) vs response-Variable slope (four parameter)). $EC_{50}$ values were calculated by the software and are shown in Table 2 below (in pM).

TABLE 2

| Example no. | In vitro potency (CRE-luciferase) low albumin $EC_{50}$ [pM] |
|---|---|
| 1 | 4.3 |
| 1a | 6.7 |
| 2 | 23 |
| 2a | 132 |
| 3 | 31 |
| 3a | 124 |
| 4 | 8.0 |
| 4a | 40 |
| 5 | 5.3 |
| 5a | 25 |
| 6 | 7.5 |
| 6a | 62 |
| 7 | 6.8 |
| 7a | 17 |
| 8 | 34 |
| 9 | 12 |
| 9a | 60 |
| 10 | 22 |
| 11 | n.d.* |
| 12 | 9.8 |
| 13 | 9.6 |
| 14 | 5.6 |
| 15 | 15 |
| 16 | 8.3 |
| 17 | 29 |
| 18 | 6.8 |
| 19 | 11 |
| 20 | 22 |
| 21 | 47 |
| 22 | 60 |
| 22a | 174 |
| 23 | 6.1 |
| 23a | 41 |
| 24 | 5.2 |
| 25 | 4.6 |
| 26 | 5.8 |
| 27 | 4.3 |
| 28 | 5.0 |
| 29 | 5.0 |
| 30 | 9.4 |
| 31 | 2.8 |

*not available for testing

The potency of all tested derivatives was confirmed in vitro.

All tested derivatives had a surprisingly good in vitro potency corresponding to an $EC_{50}$ of 100 pM or below. Twenty-two derivatives were even more potent having an $EC_{50}$ at 20 pM or below; and nineteen derivatives had a very good potency corresponding to an $EC_{50}$ at 10 pM or below.

The in vitro potency of the compounds of the invention was generally 2-8 times improved, as compared to the comparative compounds.

Example 34

GLP-1 Receptor Binding

The purpose of this experiment is to investigate the binding to the GLP-1 receptor of the GLP-1 derivatives. This is done in an in vitro experiment as described below.

The binding affinity of the GLP-1 derivatives of Examples 1-31 and comparative Examples 1a-7a, 9a, 22a, and 23a to the human GLP-1 receptor was measured by way of their ability to displace of $^{125}$I-GLP-1 from the receptor. The assay was performed with a low concentration of albumin (0.001%—corresponding to the residual amount thereof in the tracer).

Conditions

Species (in vitro): Hamster

Biological End Point: Receptor Binding

Assay Method: SPA

Receptor: GLP-1 receptor

Cell Line: BHK tk-ts13

Cell Culture and Membrane Purification

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

The cells (approx. 80% confluence) were washed twice in PBS and harvested with Versene (aqueous solution of the tetrasodium salt of ethylenediaminetetraacetic acid), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate was centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at minus 80° C.

Buffer 1: 20 mM Na-HEPES+10 mM EDTA, pH 7.4

Buffer 2: 20 mM Na-HEPES+0.1 mM EDTA, pH 7.4

Binding Assay:

SPA:

Test compounds, membranes, SPA-particles and [$^{125}$I]-GLP-1(7-36)NH$_2$ were diluted in assay buffer. 50 ul (micro liter) buffer ("low albumin" experiment containing 0.001% HSA) was added to Optiplate, and 25 ul of test compounds were added. 5-10 μg membrane protein/sample was added (50 μl) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 µl). The incubation was started with [$^{125}$I]-GLP-1]-(7-36)NH$_2$ (final concentration 0.06 nM corresponding to 49.880 DPM, 25 µl). The plates were sealed with PlateSealer and incubated for 120 minutes at 30° C. while shaking. The plates were centrifuged (1500 rpm, 10 min) and counted in Topcounter.

Assay Buffer:

50 mM HEPES 5 mM EGTA 5 mM MgCl$_2$ 0.005% Tween 20 pH 7.4

HSA was SIGMA A1653

Calculations

The IC$_{50}$ value was read from the curve as the concentration which displaces 50% of $^{125}$I-GLP-1 from the receptor.

Generally, the binding to the GLP-1 receptor at low albumin concentration should be as good as possible, corresponding to a low IC$_{50}$ value.

Results

The IC$_{50}$ [nM] value for each compound of the invention is shown in Table 3 below, together with that of the respective comparative compound. It may be related to that of the respective comparative compound by calculating N: N=100×(IC$_{50}$ (comparative compound)/IC$_{50}$ (compound of the invention)). The figure N thus shows the percentage of improvement of the receptor binding of the compounds of the invention, relative to the respective comparative compound.

TABLE 3

| Example no. | IC$_{50}$ [nM] (low albumin) |
|---|---|
| 1 | 0.34 |
| 1a | 2.27 |
| 2 | 8.99 |
| 2a | 44.50 |

TABLE 3-continued

| Example no. | IC$_{50}$ [nM] (low albumin) |
|---|---|
| 3 | 11.60 |
| 3a | 51.50 |
| 4 | 0.58 |
| 4a | 2.77 |
| 5 | 1.63 |
| 5a | 5.80 |
| 6 | 0.43 |
| 6a | 0.80 |
| 7 | 0.91 |
| 7a | 7.03 |
| 8 | 8.50 |
| 9 | 1.55 |
| 9a | 8.09 |
| 10 | 1.72 |
| 11 | 12.80 |
| 12 | 4.61 |
| 13 | 0.84 |
| 14 | 0.37 |
| 15 | 0.50 |
| 16 | 0.54 |
| 17 | 1.34 |
| 18 | 0.48 |
| 19 | 0.42 |
| 20 | 2.27 |
| 21 | 4.87 |
| 22 | 10.50 |
| 22a | 48.40 |
| 23 | 0.43 |
| 23a | 3.55 |
| 24 | 0.19 |
| 25 | 0.27 |
| 26 | 0.53 |
| 27 | 0.69 |
| 28 | 0.96 |
| 29 | 0.27 |
| 30 | 0.18 |
| 31 | 0.17 |

All tested derivatives were able to bind to the GLP-1 receptor at low concentration of albumin.

All derivatives of the invention bound tightly to the receptor with IC$_{50}$ (low albumin) values below 13 nM; twenty-six were below 5.0 nM; and nineteen were below 1.0 nM.

As can be inferred from Table 3, the receptor binding of the compounds of the invention was generally 3-8 times improved, as compared to the comparative compounds.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 peptide, wherein the GLP-1 peptide has a sequence according to Formula I:

$Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein $Xaa_7$ is L-histidine, imidazopropionyl, α-hydroxy-histidine, D-histidine, desamino-histidine, 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{16}$ is Val or Leu;
$Xaa_{18}$ is Ser or Lys;
$Xaa_{19}$ is Tyr or Gln;
$Xaa_{20}$ is Leu or Met;
$Xaa_{22}$ is Gly, Glu, Lys, or Aib;
$Xaa_{23}$ is Gln, Glu, or Arg;
$Xaa_{25}$ is Ala or Val;
$Xaa_{26}$ is Val, His, Lys, or Arg;
$Xaa_{27}$ is Glu, Leu, or Lys;
$Xaa_{30}$ is Ala, Glu, Lys, or Arg;
$Xaa_{31}$ is Trp, Lys, or His;
$Xaa_{33}$ is Val or Lys;
$Xaa_{34}$ is Lys, Glu, Asn, Gly, Gln, His, Arg, or absent;
$Xaa_{35}$ is Gly, Aib, or absent;

Xaa₃₆ is Arg, Gly, Lys, or absent;
Xaa₃₇ is Gly, Ala, Glu, Pro, Lys, Arg, or absent; and
Xaa₃₈ is Ser, Gly, Ala, Glu, Pro, Lys, Arg, or absent;
which peptide has only two Lys residues designated a first and a second Lys residue, and a maximum of eight amino acid changes as compared to GLP-1(7-37) (SEQ ID NO: 3),
which derivative comprises two protracting moieties where one protracting group is attached to the epsilon amino group of said first Lys residue, respectively, via a linker, and the other protracting group is attached to the epsilon amino group of said second Lys residue, respectively, via a linker, wherein
the protracting moiety is selected from Chem. 15, and Chem. 16:

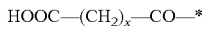 Chem. 15:

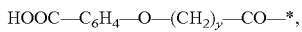 Chem. 16:

in which x is an integer in the range of 10-16, and y is an integer in the range of 8-12; and
the linker comprises gGlu-Ser, wherein gGlu has the structure of Chem. 5:

Chem. 5

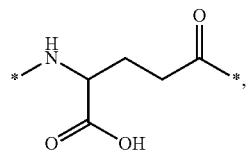

and Ser has the structure of Chem. 1:

Chem. 1

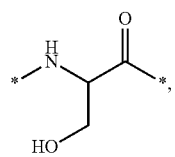

wherein the gamma carboxy group of gGlu is connected to the N-terminus of Ser in the first linker element;

or a pharmaceutically acceptable salt, amide, or ester of said derivative.

2. The derivative of claim 1, wherein the linker further comprises Chem. 2:

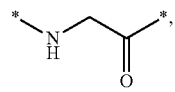

or Chem. 7:

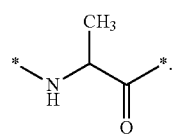

3. The derivative of claim 2, wherein the linker comprises Chem. 3:

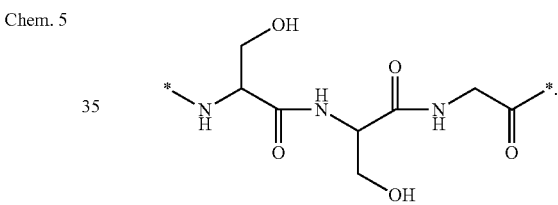

4. The derivative of claim 2, wherein the linker comprises a Chem. 4:

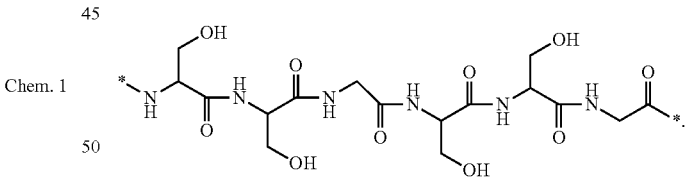

5. The derivative of claim 1, wherein the linker comprises Chem. 6:

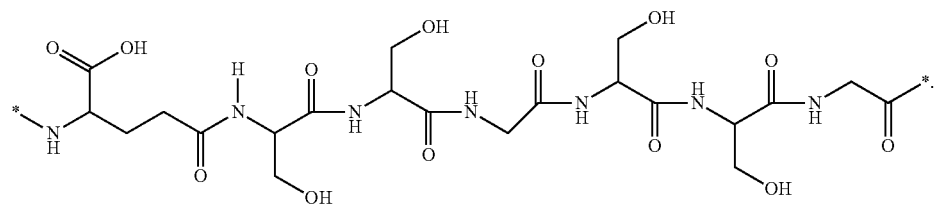

6. The derivative of claim 5, wherein the linker further comprises Chem. 12:

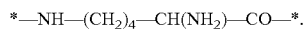

7. A pharmaceutical composition comprising a compound according to claim 1 and a pharmaceutically acceptable excipient.

8. A method for treating diabetes, obesity, binge eating, bulimia nervosa, cardiovascular diseases, gastrointestinal diseases, diabetic complications, critical illness poly-nephropathy (CIPNP), systemic inflammatory response syndrome (SIRS), bacteraemia, septicaemia, septic shock and/or polycystic ovary syndrome; and/or for improving lipid parameters, improving β-cell function, and/or for delaying or preventing diabetic disease progression in a subject in need of such treatment, said method comprising administering to said subject a pharmaceutically active amount of a compound according to claim 7.

9. The derivative according to claim 1, wherein in the sequence of Formula I, $Xaa_{18}$ and $Xaa_{26}$ are each Lys.

10. The derivative according to claim 9, wherein the GLP-1 peptide of Formula I has a maximum of four amino acid changes as compared to GLP-1(7-37) (SEQ ID NO: 3).

11. The derivative according to claim 10, wherein in the sequence of Formula I, $Xaa_{34}$ is selected from Gln or Arg.

12. The derivative according to claim 11, wherein in the sequence of Formula I, $Xaa_8$ is Aib.

13. The derivative according to claim 1, wherein in the sequence of Formula I, $Xaa_{26}$ and $Xaa_{37}$ are each Lys.

14. The derivative according to claim 13, wherein the GLP-1 peptide of Formula I has a maximum of four amino acid changes as compared to GLP-1(7-37) (SEQ ID NO: 3).

15. The derivative according to claim 14, wherein in the sequence of Formula I, $Xaa_{34}$ is selected from Gln or Arg.

16. The derivative according to claim 15, wherein in the sequence of Formula I, $Xaa_8$ is Aib.

* * * * *

UNITED STATES PATENT AND TRADEMARK OFFICE
CERTIFICATE OF CORRECTION

PATENT NO. : 10,308,700 B2  
APPLICATION NO. : 15/404808  
DATED : June 4, 2019  
INVENTOR(S) : Lau et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this  
Tenth Day of January, 2023

Katherine Kelly Vidal  
*Director of the United States Patent and Trademark Office*